US008895004B2

(12) United States Patent
Nimmrich et al.

(10) Patent No.: US 8,895,004 B2
(45) Date of Patent: Nov. 25, 2014

(54) METHOD FOR THE TREATMENT OF AMYLOIDOSES

(75) Inventors: Volker Nimmrich, Heidelberg (DE); Stefan Barghorn, Mannheim (DE); Ulrich Ebert, Mannheim (DE); Heinz Hillen, Hassloch (DE); Gerhard Gross, Speyer (DE); Andreas Draguhn, Heidelberg (DE); Claus Bruhl, Schonau (DE); Christine Grimm, Leimen (DE); Carsten Krantz, Allschwil (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 223 days.

(21) Appl. No.: 12/529,467

(22) PCT Filed: Feb. 27, 2008

(86) PCT No.: PCT/EP2008/001548
§ 371 (c)(1),
(2), (4) Date: Jul. 27, 2010

(87) PCT Pub. No.: WO2008/104385
PCT Pub. Date: Sep. 4, 2008

(65) Prior Publication Data
US 2011/0130549 A1  Jun. 2, 2011

Related U.S. Application Data

(60) Provisional application No. 60/903,695, filed on Feb. 27, 2007.

(30) Foreign Application Priority Data

Oct. 16, 2007 (EP) .................................... 07020258
Jan. 9, 2008 (EP) .................................... 08000324

(51) Int. Cl.
*A61K 39/395* (2006.01)
*A61K 31/015* (2006.01)
*A61K 31/05* (2006.01)
*A61K 31/519* (2006.01)

(52) U.S. Cl.
CPC ........... *A61K 31/015* (2013.01); *A61K 39/3955* (2013.01); *A61K 31/05* (2013.01); *A61K 31/519* (2013.01)
USPC .................... 424/139.1; 424/130.1

(58) Field of Classification Search
CPC ........... A61K 39/395; A61K 39/39558; A61K 39/0005; C07K 16/18; C07K 16/28; C07K 2317/21; C07K 2316/95; C07K 2316/96; C07K 2317/76
See application file for complete search history.

(56) References Cited

U.S. PATENT DOCUMENTS

| 4,399,216 | A | 8/1983 | Axel et al. |
| 4,510,245 | A | 4/1985 | Cousens et al. |
| 4,526,039 | A | 7/1985 | Ceccon et al. |
| 4,582,788 | A | 4/1986 | Erlich |
| 4,634,665 | A | 1/1987 | Axel et al. |
| 4,666,829 | A | 5/1987 | Glenner et al. |
| 4,683,194 | A | 7/1987 | Saike et al. |
| 4,683,202 | A | 7/1987 | Mullis |
| 4,816,397 | A | 3/1989 | Boss et al. |
| 4,816,567 | A | 3/1989 | Cabilly et al. |
| 4,880,078 | A | 11/1989 | Inoue et al. |
| 4,946,778 | A | 8/1990 | Ladner et al. |
| 4,968,615 | A | 11/1990 | Koszinowski et al. |
| 4,980,286 | A | 12/1990 | Morgan et al. |
| 5,107,065 | A | 4/1992 | Shewmaker et al. |
| 5,128,326 | A | 7/1992 | Balazs et al. |
| 5,134,062 | A | 7/1992 | Blass |
| 5,168,062 | A | 12/1992 | Stinski |
| 5,179,017 | A | 1/1993 | Axel et al. |
| 5,218,100 | A | 6/1993 | Muller-Hill et al. |
| 5,223,409 | A | 6/1993 | Ladner et al. |
| 5,225,539 | A | 7/1993 | Winter |
| 5,231,000 | A | 7/1993 | Majocha et al. |
| 5,231,020 | A | 7/1993 | Jorgensen et al. |
| 5,231,170 | A | 7/1993 | Averback |
| 5,234,814 | A | 8/1993 | Card et al. |
| 5,258,498 | A | 11/1993 | Huston et al. |
| 5,262,332 | A | 11/1993 | Selkoe |
| 5,290,540 | A | 3/1994 | Prince et al. |
| 5,403,484 | A | 4/1995 | Ladner et al. |
| 5,427,908 | A | 6/1995 | Dower et al. |
| 5,441,870 | A | 8/1995 | Seubert et al. |
| 5,455,169 | A | 10/1995 | Mullan |

(Continued)

FOREIGN PATENT DOCUMENTS

AU 2007200047 1/2007
CA 2541522 9/2007

(Continued)

OTHER PUBLICATIONS

Nimmrich V et al. J Neurosci. Jan. 2008; 28(4):788-797.*

(Continued)

*Primary Examiner* — Kimberly A Ballard
(74) *Attorney, Agent, or Firm* — Lisa V. Mueller; Michael Best & Friedrich LLP

(57) ABSTRACT

The present invention relates to a method for the treatment of an amyloidosis such as Alzheimer's disease in a subject in need thereof, characterized in that it comprises administering an inhibitor of the interaction between Aβ globulomer and the P/Q type voltage-gated presynaptic calcium channel to said subject.

3 Claims, 29 Drawing Sheets

(56) References Cited

U.S. PATENT DOCUMENTS

| | | |
|---|---|---|
| 5,516,637 A | 5/1996 | Huang et al. |
| 5,530,101 A | 6/1996 | Queen et al. |
| 5,538,845 A | 7/1996 | Knops et al. |
| 5,545,806 A | 8/1996 | Lonberg et al. |
| 5,565,332 A | 10/1996 | Hoogenboom et al. |
| 5,565,352 A | 10/1996 | Hochstrasser et al. |
| 5,567,720 A | 10/1996 | Averback |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,593,846 A | 1/1997 | Schenk et al. |
| 5,605,811 A | 2/1997 | Seubert et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |
| 5,665,355 A | 9/1997 | Primi |
| 5,679,377 A | 10/1997 | Bernstein et al. |
| 5,679,531 A | 10/1997 | Koenig |
| 5,693,753 A | 12/1997 | Koenig |
| 5,693,762 A | 12/1997 | Queen et al. |
| 5,698,426 A | 12/1997 | Huse |
| 5,705,330 A | 1/1998 | Shah et al. |
| 5,705,401 A | 1/1998 | Masters et al. |
| 5,714,350 A | 2/1998 | Co et al. |
| 5,714,352 A | 2/1998 | Jakobovits |
| 5,721,130 A | 2/1998 | Seubert et al. |
| 5,723,323 A | 3/1998 | Kauffman et al. |
| 5,733,743 A | 3/1998 | Johnson et al. |
| 5,750,349 A | 5/1998 | Suzuki et al. |
| 5,750,753 A | 5/1998 | Kimae et al. |
| 5,763,192 A | 6/1998 | Kauffman et al. |
| 5,766,846 A | 6/1998 | Schlossmacher et al. |
| 5,766,886 A | 6/1998 | Studnicka et al. |
| 5,770,429 A | 6/1998 | Lonberg et al. |
| 5,780,225 A | 7/1998 | Wigler et al. |
| 5,786,180 A | 7/1998 | Konig |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,837,500 A | 11/1998 | Ladner et al. |
| 5,855,913 A | 1/1999 | Hanes et al. |
| 5,874,064 A | 2/1999 | Edwards et al. |
| 5,877,397 A | 3/1999 | Lonberg et al. |
| 5,879,909 A | 3/1999 | Perl |
| 5,882,644 A | 3/1999 | Chang et al. |
| 5,885,793 A | 3/1999 | Griffiths et al. |
| 5,912,015 A | 6/1999 | Bernstein et al. |
| 5,912,120 A | 6/1999 | Goldstein et al. |
| 5,916,597 A | 6/1999 | Lee et al. |
| 5,916,771 A | 6/1999 | Horr et al. |
| 5,934,272 A | 8/1999 | Lloyd et al. |
| 5,939,598 A | 8/1999 | Kucherlapati et al. |
| 5,955,285 A | 9/1999 | Averback |
| 5,955,317 A | 9/1999 | Suzuki et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jokobovits et al. |
| 6,010,913 A | 1/2000 | Vandermeeren et al. |
| 6,018,024 A | 1/2000 | Seubert et al. |
| 6,019,968 A | 2/2000 | Platz et al. |
| 6,075,181 A | 6/2000 | Kucherlapati et al. |
| 6,091,001 A | 7/2000 | Jakobovits et al. |
| 6,114,133 A | 9/2000 | Seubert et al. |
| 6,114,598 A | 9/2000 | Kucherlapati et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,218,506 B1 | 4/2001 | Krafft et al. |
| 6,284,221 B1 | 9/2001 | Schenk et al. |
| 6,287,793 B1 | 9/2001 | Schenk et al. |
| 6,294,171 B2 | 9/2001 | Mcmichael |
| 6,309,892 B1 | 10/2001 | Averback |
| 6,323,218 B1 | 11/2001 | Bush et al. |
| 6,333,034 B1 | 12/2001 | Gupta-bansal et al. |
| 6,350,861 B1 | 2/2002 | Co et al. |
| 6,387,674 B1 | 5/2002 | Trasciatti et al. |
| 6,582,945 B1 | 6/2003 | Raso |
| 6,610,493 B1 | 8/2003 | Citron et al. |
| 6,660,843 B1 | 12/2003 | Feige et al. |
| 6,664,442 B2 | 12/2003 | McConlogue et al. |
| 6,699,658 B1 | 3/2004 | Wittrup et al. |
| 6,710,226 B1 | 3/2004 | Schenk |
| 6,713,450 B2 | 3/2004 | Frangione et al. |
| 6,743,427 B1 | 6/2004 | Schenk |
| 6,750,324 B1 | 6/2004 | Schenk |
| 6,761,888 B1 | 7/2004 | Schenk |
| 6,785,434 B2 | 8/2004 | Castoldi et al. |
| 6,787,138 B1 | 9/2004 | Schenk |
| 6,787,139 B1 | 9/2004 | Schenk |
| 6,787,140 B1 | 9/2004 | Schenk |
| 6,787,143 B1 | 9/2004 | Schenk |
| 6,787,144 B1 | 9/2004 | Schenk |
| 6,787,523 B1 | 9/2004 | Schenk |
| 6,787,637 B1 | 9/2004 | Schenk |
| 6,815,175 B2 | 11/2004 | Weksler |
| 6,849,416 B2 | 2/2005 | Wiltfang et al. |
| 6,866,849 B2 | 3/2005 | Schenk |
| 6,866,850 B2 | 3/2005 | Schenk |
| 6,872,554 B2 | 3/2005 | Raso |
| 6,875,434 B1 | 4/2005 | Schenk |
| 6,905,686 B1 | 6/2005 | Schenk |
| 6,913,745 B1 | 7/2005 | Schenk |
| 6,919,075 B1 | 7/2005 | Solomon et al. |
| 6,972,127 B2 | 12/2005 | Schenk |
| 6,982,084 B2 | 1/2006 | Schenk |
| 7,014,855 B2 | 3/2006 | Schenk |
| 7,022,500 B1 | 4/2006 | Queen et al. |
| 7,045,531 B1 | 5/2006 | Bush et al. |
| 7,060,270 B2 | 6/2006 | Nicolau et al. |
| 7,067,133 B2 | 6/2006 | Nicolau |
| 7,094,884 B2 | 8/2006 | Scholz et al. |
| 7,122,374 B1 | 10/2006 | Saido et al. |
| 7,135,181 B2 | 11/2006 | Jensen et al. |
| 7,169,389 B2 | 1/2007 | Di Padova et al. |
| 7,179,463 B2 | 2/2007 | Lannfelt et al. |
| 7,179,606 B2 | 2/2007 | Jackowski et al. |
| 7,179,892 B2 | 2/2007 | Basi et al. |
| 7,186,881 B2 | 3/2007 | Games et al. |
| 7,189,703 B2 | 3/2007 | Balin et al. |
| 7,189,819 B2 | 3/2007 | Basi et al. |
| 7,195,761 B2 | 3/2007 | Holtzman et al. |
| 7,195,881 B2 | 3/2007 | Geffard |
| 7,196,163 B2 | 3/2007 | Hazuda et al. |
| 7,226,730 B1 | 6/2007 | De La Monte et al. |
| 7,238,488 B2 | 7/2007 | Maresh et al. |
| 7,238,788 B2 | 7/2007 | Lee |
| 7,247,301 B2 | 7/2007 | van de Winkel et al. |
| 7,256,273 B2 | 8/2007 | Basi et al. |
| 7,270,818 B2 | 9/2007 | Averback |
| 7,279,165 B2 | 10/2007 | Bachmann et al. |
| 7,318,923 B2 | 1/2008 | Tsurushita et al. |
| 7,320,790 B2 | 1/2008 | Hinton et al. |
| 7,320,793 B2 | 1/2008 | Renner et al. |
| 7,335,491 B2 | 2/2008 | Drapeau et al. |
| 7,339,035 B2 | 3/2008 | Yanagisawa et al. |
| 7,342,091 B2 | 3/2008 | Kapurniotu et al. |
| 7,371,365 B2 | 5/2008 | Poduslo et al. |
| 7,375,190 B2 | 5/2008 | Cheng et al. |
| 7,413,884 B2 | 8/2008 | Raso |
| 7,427,342 B2 | 9/2008 | Barber |
| 7,625,560 B2 | 12/2009 | Basi et al. |
| 7,772,375 B2 | 8/2010 | Greferath et al. |

(56) References Cited

U.S. PATENT DOCUMENTS

| | | |
|---|---|---|
| 7,892,544 B2 | 2/2011 | Pfeifer et al. |
| 7,902,328 B2 | 3/2011 | Hillen et al. |
| 2001/0029293 A1 | 10/2001 | Gallatin et al. |
| 2002/0009445 A1 | 1/2002 | Du et al. |
| 2002/0015941 A1 | 2/2002 | Kim et al. |
| 2002/0086014 A1 | 7/2002 | Korman et al. |
| 2002/0086847 A1 | 7/2002 | Chain |
| 2002/0094335 A1 | 7/2002 | Chalifour et al. |
| 2002/0132758 A1 | 9/2002 | Shell et al. |
| 2002/0137134 A1 | 9/2002 | Gemgross |
| 2002/0162129 A1 | 10/2002 | Lannfelt et al. |
| 2002/0182644 A1 | 12/2002 | Diamandis |
| 2002/0182660 A1 | 12/2002 | Fong |
| 2002/0188106 A1 | 12/2002 | Mandelkow et al. |
| 2002/0197258 A1 | 12/2002 | Ghanbari et al. |
| 2003/0065141 A1 | 4/2003 | Carter et al. |
| 2003/0068316 A1 | 4/2003 | Klein et al. |
| 2003/0073655 A1 | 4/2003 | Chain |
| 2003/0077278 A1 | 4/2003 | Gallatin et al. |
| 2003/0077757 A1 | 4/2003 | Andrews |
| 2003/0086938 A1 | 5/2003 | Jensen et al. |
| 2003/0100011 A1 | 5/2003 | Jackowski et al. |
| 2003/0100058 A1 | 5/2003 | Roschke et al. |
| 2003/0108551 A1 | 6/2003 | Nicolau et al. |
| 2003/0114510 A1 | 6/2003 | Ingram et al. |
| 2003/0147882 A1 | 8/2003 | Solomon et al. |
| 2003/0148356 A1 | 8/2003 | Cruts et al. |
| 2003/0157117 A1 | 8/2003 | Rasmussen et al. |
| 2003/0180722 A1 | 9/2003 | Godbole et al. |
| 2003/0185826 A1 | 10/2003 | Tobinick |
| 2003/0185827 A1 | 10/2003 | Rodriguez et al. |
| 2003/0186333 A1 | 10/2003 | Loring et al. |
| 2003/0186374 A1 | 10/2003 | Hufton et al. |
| 2003/0190689 A1 | 10/2003 | Crosby et al. |
| 2003/0194403 A1 | 10/2003 | van de Winkel et al. |
| 2003/0195347 A1 | 10/2003 | Baker et al. |
| 2003/0228307 A1 | 12/2003 | Ramakrishnan et al. |
| 2003/0229907 A1 | 12/2003 | Hsiao et al. |
| 2003/0232758 A1 | 12/2003 | St. George-Hyslop et al. |
| 2004/0013647 A1 | 1/2004 | Solomon et al. |
| 2004/0013680 A1 | 1/2004 | Bush et al. |
| 2004/0018590 A1 | 1/2004 | Gemgross et al. |
| 2004/0043418 A1 | 3/2004 | Holtzman et al. |
| 2004/0053371 A1 | 3/2004 | Maresh et al. |
| 2004/0058414 A1 | 3/2004 | Queen et al. |
| 2004/0081657 A1 | 4/2004 | Schenk |
| 2004/0116337 A1 | 6/2004 | Kapurniotu et al. |
| 2004/0127471 A1* | 7/2004 | Reisberg ............... 514/165 |
| 2004/0138296 A1 | 7/2004 | Robertson et al. |
| 2004/0142872 A1 | 7/2004 | Podusio et al. |
| 2004/0146512 A1 | 7/2004 | Rosenthal et al. |
| 2004/0157267 A1 | 8/2004 | Huang |
| 2004/0157779 A1 | 8/2004 | Schenk |
| 2004/0166119 A1 | 8/2004 | Schenk |
| 2004/0170641 A1 | 9/2004 | Schenk |
| 2004/0175394 A1 | 9/2004 | Schenk |
| 2004/0185039 A1 | 9/2004 | Kohler et al. |
| 2004/0191264 A1 | 9/2004 | Nielsen et al. |
| 2004/0192898 A1 | 9/2004 | Jia et al. |
| 2004/0213800 A1 | 10/2004 | Seubert et al. |
| 2004/0223912 A1 | 11/2004 | Montalto et al. |
| 2004/0223970 A1 | 11/2004 | Afar et al. |
| 2004/0228865 A1 | 11/2004 | Schenk |
| 2004/0241164 A1 | 12/2004 | Bales et al. |
| 2004/0242845 A1 | 12/2004 | Nicolau et al. |
| 2004/0248197 A1 | 12/2004 | Holtzman et al. |
| 2004/0265308 A1 | 12/2004 | Schenk |
| 2004/0265919 A1 | 12/2004 | Vanderstichele et al. |
| 2005/0009110 A1 | 1/2005 | Chang |
| 2005/0014821 A1* | 1/2005 | Tsai et al. ............... 514/473 |
| 2005/0019330 A1 | 1/2005 | Schenk |
| 2005/0019343 A1 | 1/2005 | Schenk |
| 2005/0031651 A1 | 2/2005 | Gervais et al. |
| 2005/0037026 A1 | 2/2005 | Schenk |
| 2005/0042664 A1 | 2/2005 | Wu et al. |
| 2005/0048584 A1 | 3/2005 | Lamping et al. |
| 2005/0053614 A1 | 3/2005 | Schenk |
| 2005/0057813 A1 | 3/2005 | Hasei et al. |
| 2005/0059591 A1 | 3/2005 | Schenk et al. |
| 2005/0059802 A1 | 3/2005 | Schenk et al. |
| 2005/0090439 A1 | 4/2005 | Chalifour et al. |
| 2005/0112543 A1 | 5/2005 | Bush et al. |
| 2005/0118651 A1 | 6/2005 | Basi et al. |
| 2005/0123544 A1 | 6/2005 | Schenk et al. |
| 2005/0124016 A1 | 6/2005 | LaDu et al. |
| 2005/0129691 A1 | 6/2005 | Gerlai |
| 2005/0129695 A1 | 6/2005 | Mercken et al. |
| 2005/0142131 A1 | 6/2005 | Hinton et al. |
| 2005/0142132 A1 | 6/2005 | Schenk et al. |
| 2005/0147613 A1 | 7/2005 | Raso |
| 2005/0153381 A1 | 7/2005 | Marusich et al. |
| 2005/0163744 A1 | 7/2005 | Rasmussen et al. |
| 2005/0163788 A1 | 7/2005 | Schenk |
| 2005/0169925 A1 | 8/2005 | Bardroff et al. |
| 2005/0175626 A1 | 8/2005 | Delacourte et al. |
| 2005/0249725 A1 | 11/2005 | Schenk et al. |
| 2005/0249727 A1 | 11/2005 | Schenk |
| 2005/0255122 A1 | 11/2005 | Schenk |
| 2005/0272025 A1 | 12/2005 | Suo et al. |
| 2006/0008458 A1 | 1/2006 | Solomon |
| 2006/0029603 A1 | 2/2006 | Ellis et al. |
| 2006/0029611 A1 | 2/2006 | Schenk |
| 2006/0034858 A1 | 2/2006 | Schenk |
| 2006/0039906 A1 | 2/2006 | Holtzman et al. |
| 2006/0057646 A1 | 3/2006 | Wiltfang et al. |
| 2006/0057701 A1 | 3/2006 | Rosenthal et al. |
| 2006/0057702 A1 | 3/2006 | Rosenthal et al. |
| 2006/0062786 A1 | 3/2006 | Salcedo et al. |
| 2006/0073149 A1 | 4/2006 | Bales et al. |
| 2006/0099211 A1 | 5/2006 | Monthe et al. |
| 2006/0104968 A1 | 5/2006 | Bookbinder et al. |
| 2006/0105394 A1 | 5/2006 | Pomara |
| 2006/0110388 A1 | 5/2006 | Davies et al. |
| 2006/0111301 A1 | 5/2006 | Mattner |
| 2006/0127954 A1 | 6/2006 | Mercken et al. |
| 2006/0141541 A1 | 6/2006 | McIntyre |
| 2006/0160161 A1 | 7/2006 | Pavliakova et al. |
| 2006/0165682 A1 | 7/2006 | Basi et al. |
| 2006/0166275 A1 | 7/2006 | Krafft et al. |
| 2006/0166311 A1 | 7/2006 | Okochi et al. |
| 2006/0188505 A1 | 8/2006 | Skurkovich et al. |
| 2006/0193850 A1 | 8/2006 | Warne et al. |
| 2006/0198851 A1 | 9/2006 | Basi et al. |
| 2006/0228349 A1 | 10/2006 | Acton et al. |
| 2006/0234947 A1 | 10/2006 | Gazit |
| 2006/0240007 A1 | 10/2006 | Sanders |
| 2006/0241038 A1 | 10/2006 | Watanabe et al. |
| 2006/0246075 A1 | 11/2006 | Mercken et al. |
| 2006/0257420 A1 | 11/2006 | Zimmerman |
| 2006/0257882 A1 | 11/2006 | Shimkets |
| 2006/0280733 A1 | 12/2006 | Kayed et al. |
| 2006/0292152 A1 | 12/2006 | Rosenthal et al. |
| 2007/0009931 A1 | 1/2007 | Kirsch |
| 2007/0010435 A1 | 1/2007 | Frangione et al. |
| 2007/0010657 A1 | 1/2007 | Klocke et al. |
| 2007/0015217 A1 | 1/2007 | Durham et al. |
| 2007/0015218 A1 | 1/2007 | Cao et al. |
| 2007/0021345 A1 | 1/2007 | Gazit |
| 2007/0031416 A1 | 2/2007 | Shoji et al. |
| 2007/0036789 A1 | 2/2007 | Chung |
| 2007/0036794 A1 | 2/2007 | Devaux |
| 2007/0042424 A1 | 2/2007 | Ebinuma et al. |
| 2007/0048312 A1 | 3/2007 | Klein et al. |
| 2007/0071675 A1 | 3/2007 | Wu et al. |
| 2007/0072307 A1 | 3/2007 | Godavarti et al. |
| 2007/0081998 A1 | 4/2007 | Kinney et al. |
| 2007/0082350 A1 | 4/2007 | Landfield et al. |
| 2007/0086994 A1 | 4/2007 | Wallach et al. |
| 2007/0098721 A1 | 5/2007 | Hillen et al. |
| 2007/0105092 A1 | 5/2007 | Paul et al. |
| 2007/0110750 A1 | 5/2007 | Glabe et al. |
| 2007/0111252 A1 | 5/2007 | Suzuki et al. |
| 2007/0122405 A1 | 5/2007 | Roschke et al. |
| 2007/0128191 A1 | 6/2007 | Barrio |

(56) References Cited

U.S. PATENT DOCUMENTS

| | | | |
|---|---|---|---|
| 2007/0134247 | A9 | 6/2007 | Solomon |
| 2007/0135337 | A2 | 6/2007 | Chalifour et al. |
| 2007/0140966 | A1 | 6/2007 | Chang et al. |
| 2007/0148167 | A1 | 6/2007 | Strohl |
| 2007/0160616 | A1 | 7/2007 | Rosenthal et al. |
| 2007/0167522 | A1 | 7/2007 | Imawaka et al. |
| 2007/0190046 | A1 | 8/2007 | DeMaattos et al. |
| 2007/0196367 | A1 | 8/2007 | Dinu |
| 2007/0213512 | A1 | 9/2007 | Krafft et al. |
| 2007/0218069 | A1 | 9/2007 | Gordon et al. |
| 2007/0218499 | A1 | 9/2007 | Lambert et al. |
| 2007/0231331 | A1 | 10/2007 | Dewji et al. |
| 2007/0248606 | A1 | 10/2007 | Lannfelt et al. |
| 2007/0264276 | A1 | 11/2007 | Chalifour et al. |
| 2007/0280953 | A1 | 12/2007 | Rosenberg et al. |
| 2007/0292410 | A1 | 12/2007 | Cashman et al. |
| 2007/0292895 | A1 | 12/2007 | Shi et al. |
| 2008/0009467 | A1 | 1/2008 | Henderson |
| 2008/0014194 | A1 | 1/2008 | Schenk et al. |
| 2008/0025988 | A1 | 1/2008 | Yamaguchi et al. |
| 2008/0029911 | A1 | 2/2008 | Jeon et al. |
| 2008/0044356 | A1 | 2/2008 | Lesne et al. |
| 2008/0044406 | A1 | 2/2008 | Johnson-Wood et al. |
| 2008/0051690 | A1 | 2/2008 | Mattner et al. |
| 2008/0057053 | A1 | 3/2008 | Stolen |
| 2008/0057593 | A1 | 3/2008 | Vanderstichele et al. |
| 2008/0058276 | A1 | 3/2008 | Lu et al. |
| 2008/0058330 | A1 | 3/2008 | Paris et al. |
| 2008/0089885 | A1 | 4/2008 | Smith et al. |
| 2008/0096818 | A1 | 4/2008 | Schenk et al. |
| 2008/0107601 | A1 | 5/2008 | Lauwereys et al. |
| 2008/0107649 | A1 | 5/2008 | Zurbriggen |
| 2008/0113444 | A1 | 5/2008 | Pray |
| 2008/0131422 | A1 | 6/2008 | Sugimura et al. |
| 2008/0199879 | A1 | 8/2008 | Takayama et al. |
| 2008/0220449 | A1 | 9/2008 | Vasan et al. |
| 2008/0292639 | A1 | 11/2008 | Shen et al. |
| 2008/0299111 | A1 | 12/2008 | Delacourte et al. |
| 2009/0018084 | A1 | 1/2009 | Krafft et al. |
| 2009/0023159 | A1 | 1/2009 | Mendez |
| 2009/0035295 | A1 | 2/2009 | Hillen et al. |
| 2009/0035307 | A1 | 2/2009 | Barghorn et al. |
| 2009/0074775 | A1 | 3/2009 | Holtzman et al. |
| 2009/0155246 | A1 | 6/2009 | Gellerfors et al. |
| 2009/0156471 | A1 | 6/2009 | Gazit et al. |
| 2009/0162362 | A1 | 6/2009 | Sarasa |
| 2009/0162878 | A1 | 6/2009 | Kim et al. |
| 2009/0175847 | A1 | 7/2009 | Hillen |
| 2009/0191190 | A1 | 7/2009 | Barghorn |
| 2009/0214515 | A1 | 8/2009 | Holzman et al. |
| 2009/0232801 | A1 | 9/2009 | Hillen |
| 2009/0238831 | A1 | 9/2009 | Hillen et al. |
| 2010/0173828 | A1 | 7/2010 | Hillen |
| 2010/0209346 | A1 | 8/2010 | Hillen et al. |
| 2011/0092445 | A1 | 4/2011 | Barghorn |
| 2011/0212109 | A1 | 9/2011 | Barghorn |
| 2011/0256138 | A1 | 10/2011 | Barghorn |
| 2011/0287005 | A1 | 11/2011 | Hillen |
| 2012/0034166 | A1 | 2/2012 | Hillen |

FOREIGN PATENT DOCUMENTS

| | | |
|---|---|---|
| CN | 1396183 | 2/2003 |
| CN | 1446581 | 10/2003 |
| CN | 1673369 | 9/2005 |
| CN | 1721437 | 1/2006 |
| CN | 1803842 | 7/2006 |
| CN | 101058608 | 10/2007 |
| CN | 101084909 | 12/2007 |
| CN | 101152576 | 4/2008 |
| DE | 19902550 | 7/2000 |
| DE | 10055703 | 5/2002 |
| DE | 10303974 | 8/2004 |
| DE | 102004039326 | 2/2006 |
| EP | 0045665 | 2/1982 |
| EP | 0050424 | 9/1985 |
| EP | 0285159 | 10/1988 |
| EP | 0341491 | 11/1989 |
| EP | 0084796 | 5/1990 |
| EP | 0391714 | 10/1990 |
| EP | 0411974 | 2/1991 |
| EP | 0415801 | 3/1991 |
| EP | 0237362 | 3/1992 |
| EP | 0201184 | 12/1992 |
| EP | 0229246 | 8/1993 |
| EP | 0368684 | 3/1994 |
| EP | 0239400 | 8/1994 |
| EP | 0613007 | 8/1994 |
| EP | 0623675 | 11/1994 |
| EP | 0557270 | 5/1995 |
| EP | 0519598 | 6/1995 |
| EP | 0440619 | 1/1996 |
| EP | 0304013 | 6/1996 |
| EP | 0589877 | 11/1996 |
| EP | 0436597 | 4/1997 |
| EP | 0258017 | 6/1997 |
| EP | 0783104 | 7/1997 |
| EP | 0444856 | 9/1997 |
| EP | 0816492 | 1/1998 |
| EP | 0592127 | 4/1998 |
| EP | 0274826 | 8/1998 |
| EP | 0527839 | 12/1998 |
| EP | 1038958 | 9/2000 |
| EP | 1094080 | 4/2001 |
| EP | 1130032 | 11/2001 |
| EP | 1172378 | 1/2002 |
| EP | 1176195 | 1/2002 |
| EP | 0877939 | 6/2002 |
| EP | 0683234 | 5/2003 |
| EP | 1308461 | 5/2003 |
| EP | 1408333 | 4/2004 |
| EP | 1420032 | 5/2004 |
| EP | 1270592 | 9/2004 |
| EP | 1467212 | 10/2004 |
| EP | 0592106 | 11/2004 |
| EP | 1200470 | 11/2004 |
| EP | 0519596 | 2/2005 |
| EP | 1538163 | 6/2005 |
| EP | 1632242 | 3/2006 |
| EP | 1092767 | 10/2006 |
| EP | 1717250 | 11/2006 |
| EP | 0998495 | 12/2006 |
| EP | 1731913 | 12/2006 |
| EP | 1049712 | 1/2007 |
| EP | 1741783 | 1/2007 |
| EP | 1346041 | 2/2007 |
| EP | 1752472 | 2/2007 |
| EP | 1592476 | 4/2007 |
| EP | 0970203 | 5/2007 |
| EP | 1787998 | 5/2007 |
| EP | 0948536 | 6/2007 |
| EP | 1160256 | 6/2007 |
| EP | 1379546 | 6/2007 |
| EP | 1792991 | 6/2007 |
| EP | 1842859 | 10/2007 |
| EP | 1861422 | 12/2007 |
| EP | 1878751 | 1/2008 |
| EP | 1434053 | 3/2008 |
| EP | 1521831 | 4/2008 |
| EP | 1778837 | 4/2008 |
| EP | 1911765 | 4/2008 |
| EP | 1781644 | 5/2008 |
| EP | 0911398 | 6/2008 |
| EP | 1976877 | 10/2008 |
| EP | 2009445 | 12/2008 |
| EP | 1623719 | 1/2009 |
| EP | 1681566 | 8/2009 |
| EP | 1766396 | 8/2010 |
| EP | 1720909 | 11/2011 |
| FR | 2740454 | 4/1997 |
| FR | 2741881 | 6/1997 |
| GB | 1495159 | 12/1977 |
| GB | 2371303 | 7/2002 |

(56) References Cited

FOREIGN PATENT DOCUMENTS

| | | |
|---|---|---|
| GR | 1005016 | 10/2005 |
| JP | 63240797 | 10/1988 |
| JP | 4252195 | 9/1992 |
| JP | 4320694 | 11/1992 |
| JP | 7209295 | 8/1995 |
| JP | 7209296 | 8/1995 |
| JP | 07238096 | 9/1995 |
| JP | 7309900 | 11/1995 |
| JP | 8245700 | 9/1996 |
| JP | 9067397 | 3/1997 |
| JP | 10075781 | 3/1998 |
| JP | 10210982 | 8/1998 |
| JP | 2000050885 | 2/2000 |
| JP | 2000354487 | 12/2000 |
| JP | 2001231578 | 8/2001 |
| JP | 2002040023 | 2/2002 |
| JP | 2002253252 | 9/2002 |
| JP | 2004107260 | 4/2004 |
| JP | 2005185281 | 7/2005 |
| JP | 2006166879 | 6/2006 |
| JP | 2006213621 | 8/2006 |
| JP | 2006265189 | 10/2006 |
| JP | 2007077103 | 3/2007 |
| JP | 2007300856 | 11/2007 |
| JP | 2007319127 | 12/2007 |
| JP | 2008096311 | 4/2008 |
| KR | 100806914 | 2/2008 |
| WO | WO 88/03951 | 6/1988 |
| WO | WO 89/06689 | 7/1989 |
| WO | WO 89/07657 | 8/1989 |
| WO | WO 90/02809 | 3/1990 |
| WO | WO 90/05144 | 5/1990 |
| WO | WO 90/12870 | 11/1990 |
| WO | WO 90/14424 | 11/1990 |
| WO | WO 90/14430 | 11/1990 |
| WO | WO 90/14443 | 11/1990 |
| WO | WO 91/05548 | 5/1991 |
| WO | WO 91/09967 | 7/1991 |
| WO | WO 91/10737 | 7/1991 |
| WO | WO 91/10741 | 7/1991 |
| WO | WO 91/17271 | 11/1991 |
| WO | WO 92/01047 | 1/1992 |
| WO | WO 92/02551 | 2/1992 |
| WO | WO 92/00969 | 6/1992 |
| WO | WO 92/09690 | 6/1992 |
| WO | WO 92/11018 | 7/1992 |
| WO | WO 92/15679 | 9/1992 |
| WO | WO 92/18619 | 10/1992 |
| WO | WO 92/19244 | 11/1992 |
| WO | WO 92/20791 | 11/1992 |
| WO | WO 92/22324 | 12/1992 |
| WO | WO 93/01288 | 1/1993 |
| WO | WO 93/08302 | 4/1993 |
| WO | WO 93/11236 | 10/1993 |
| WO | WO 94/02602 | 3/1994 |
| WO | WO 94/17197 | 8/1994 |
| WO | WO 95/07707 | 3/1995 |
| WO | WO 95/11311 | 4/1995 |
| WO | WO 95/11994 | 5/1995 |
| WO | WO 95/15982 | 6/1995 |
| WO | WO 95/16787 | 6/1995 |
| WO | WO 95/20401 | 8/1995 |
| WO | WO 96/20218 | 7/1996 |
| WO | WO 96/20698 | 7/1996 |
| WO | WO 96/28187 | 9/1996 |
| WO | WO 96/33735 | 10/1996 |
| WO | WO 96/34096 | 10/1996 |
| WO | 96/39512 | 12/1996 |
| WO | WO 96/39512 | 12/1996 |
| WO | WO 96/40731 | 12/1996 |
| WO | WO 97/08320 | 3/1997 |
| WO | WO 97/10505 | 3/1997 |
| WO | WO 97/18476 | 5/1997 |
| WO | WO 97/29131 | 8/1997 |
| WO | WO 97/32572 | 9/1997 |
| WO | WO 97/44013 | 11/1997 |
| WO | WO 97/46678 | 12/1997 |
| WO | WO 98/05350 | 2/1998 |
| WO | WO 98/07850 | 2/1998 |
| WO | WO 98/13490 | 4/1998 |
| WO | WO 98/16654 | 4/1998 |
| WO | WO 98/22120 | 5/1998 |
| WO | WO 98/24893 | 6/1998 |
| WO | 98/13490 | 7/1998 |
| WO | WO 98/28445 | 7/1998 |
| WO | WO 98/31346 | 7/1998 |
| WO | WO 98/31700 | 7/1998 |
| WO | WO 98/33815 | 8/1998 |
| WO | WO 98/41201 | 9/1998 |
| WO | WO 98/47343 | 10/1998 |
| WO | WO 98/49286 | 11/1998 |
| WO | WO 98/50433 | 11/1998 |
| WO | WO 98/51793 | 11/1998 |
| WO | WO 99/05175 | 2/1999 |
| WO | WO 99/09150 | 2/1999 |
| WO | WO 99/12870 | 3/1999 |
| WO | WO 99/13908 | 3/1999 |
| WO | WO 99/15154 | 4/1999 |
| WO | WO 99/20253 | 4/1999 |
| WO | WO 99/22024 | 5/1999 |
| WO | WO 99/25044 | 5/1999 |
| WO | WO 99/27944 | 6/1999 |
| WO | WO 99/27949 | 6/1999 |
| WO | WO 99/33815 | 7/1999 |
| WO | WO 99/36569 | 7/1999 |
| WO | WO 99/40909 | 8/1999 |
| WO | WO 99/45031 | 9/1999 |
| WO | WO 99/45962 | 9/1999 |
| WO | WO 99/53049 | 10/1999 |
| WO | WO 99/58157 | 11/1999 |
| WO | WO 99/58564 | 11/1999 |
| WO | WO 99/59571 | 11/1999 |
| WO | WO 99/62505 | 12/1999 |
| WO | WO 99/66903 | 12/1999 |
| WO | WO 00/09560 | 2/2000 |
| WO | WO 00/17345 | 3/2000 |
| WO | WO 00/18805 | 4/2000 |
| WO | WO 00/29446 | 5/2000 |
| WO | WO 00/32805 | 6/2000 |
| WO | WO 00/35939 | 6/2000 |
| WO | WO 00/37504 | 6/2000 |
| WO | WO 00/56772 | 9/2000 |
| WO | WO 00/58344 | 10/2000 |
| WO | WO 00/72870 | 12/2000 |
| WO | WO 00/72876 | 12/2000 |
| WO | WO 00/72880 | 12/2000 |
| WO | WO 00/75328 | 12/2000 |
| WO | WO 00/77178 | 12/2000 |
| WO | WO 00/78807 | 12/2000 |
| WO | WO 01/10900 | 2/2001 |
| WO | WO 01/16364 | 3/2001 |
| WO | WO 01/18169 | 3/2001 |
| WO | WO 01/32712 | 5/2001 |
| WO | WO 01/39796 | 6/2001 |
| WO | WO 01/42306 | 6/2001 |
| WO | WO 01/62284 | 8/2001 |
| WO | WO 01/62801 | 8/2001 |
| WO | WO 01/68860 | 9/2001 |
| WO | WO 01/83519 | 11/2001 |
| WO | WO 01/83525 | 11/2001 |
| WO | WO 01/85093 | 11/2001 |
| WO | WO 01/90182 | 11/2001 |
| WO | WO 01/98361 | 12/2001 |
| WO | WO 02/00245 | 1/2002 |
| WO | WO 02/03911 | 1/2002 |
| WO | WO 02/21141 | 3/2002 |
| WO | WO 02/30980 | 4/2002 |
| WO | WO 02/34777 | 5/2002 |
| WO | WO 02/36614 | 5/2002 |
| WO | WO 02/46237 | 6/2002 |
| WO | WO 02/055552 | 7/2002 |
| WO | WO 02/059155 | 8/2002 |
| WO | WO 02/062851 | 8/2002 |
| WO | WO 02/074240 | 9/2002 |

(56) References Cited

FOREIGN PATENT DOCUMENTS

| | | |
|---|---|---|
| WO | WO 02/081505 | 10/2002 |
| WO | WO 02/085922 | 10/2002 |
| WO | WO 02/088306 | 11/2002 |
| WO | WO 02/088307 | 11/2002 |
| WO | WO 02/094870 | 11/2002 |
| WO | WO 02/094985 | 11/2002 |
| WO | WO 02/096350 | 12/2002 |
| WO | WO 02/096937 | 12/2002 |
| WO | WO 03/000714 | 1/2003 |
| WO | WO 03/008626 | 1/2003 |
| WO | WO 03/014162 | 2/2003 |
| WO | WO 03/014329 | 2/2003 |
| WO | WO 03/015617 | 2/2003 |
| WO | WO 03/015691 | 2/2003 |
| WO | WO 03/015812 | 2/2003 |
| WO | WO 03/016466 | 2/2003 |
| WO | WO 03/016467 | 2/2003 |
| WO | WO 03/020212 | 3/2003 |
| WO | WO 03/028668 | 4/2003 |
| WO | WO 03/031475 | 4/2003 |
| WO | WO 03/035835 | 5/2003 |
| WO | WO 03/039467 | 5/2003 |
| WO | WO 03/045128 | 6/2003 |
| WO | WO 03/046012 | 6/2003 |
| WO | WO 03/047499 | 6/2003 |
| WO | WO 03/051374 | 6/2003 |
| WO | WO 03/070760 | 8/2003 |
| WO | WO 03/074081 | 8/2003 |
| WO | WO 03/074004 | 9/2003 |
| WO | WO 03/074569 | 9/2003 |
| WO | WO 03/076455 | 9/2003 |
| WO | WO 03/077858 | 9/2003 |
| WO | WO 03/080672 | 10/2003 |
| WO | WO 03/089460 | 10/2003 |
| WO | WO 03/090772 | 11/2003 |
| WO | WO 03/091734 | 11/2003 |
| WO | WO 03/095429 | 11/2003 |
| WO | WO 03/100419 | 12/2003 |
| WO | WO 03/104437 | 12/2003 |
| WO | WO 03/105658 | 12/2003 |
| WO | WO 04/001422 | 12/2003 |
| WO | WO 2004/003019 | 1/2004 |
| WO | WO 2004/003563 | 1/2004 |
| WO | WO 2004/006861 | 1/2004 |
| WO | WO 2004/009776 | 1/2004 |
| WO | WO 2004/011674 | 2/2004 |
| WO | WO 2004/011943 | 2/2004 |
| WO | WO 2004/013172 | 2/2004 |
| WO | WO 2004/014296 | 2/2004 |
| WO | WO 2004/014367 | 2/2004 |
| WO | WO 2004/016282 | 2/2004 |
| WO | WO 2004/016655 | 2/2004 |
| WO | WO 2004/018997 | 3/2004 |
| WO | WO 2004/019045 | 3/2004 |
| WO | WO 2004/024090 | 3/2004 |
| WO | WO 2004/029093 | 4/2004 |
| WO | WO 2004/029630 | 4/2004 |
| WO | WO 2004/031241 | 4/2004 |
| WO | WO 2004/031400 | 4/2004 |
| WO | WO 2004/032868 | 4/2004 |
| WO | WO 2004/033397 | 4/2004 |
| WO | WO 2004/038411 | 5/2004 |
| WO | WO 2004/041067 | 5/2004 |
| WO | WO 2004/043989 | 5/2004 |
| WO | WO 2004/044204 | 5/2004 |
| WO | WO 2004/045525 | 6/2004 |
| WO | WO 2004/050707 | 6/2004 |
| WO | WO 2004/050850 | 6/2004 |
| WO | WO 2004/050876 | 6/2004 |
| WO | WO 2004/056318 | 7/2004 |
| WO | WO 2004/058239 | 7/2004 |
| WO | WO 2004/058258 | 7/2004 |
| WO | WO 2004/058820 | 7/2004 |
| WO | WO 2004/062556 | 7/2004 |
| WO | 2004067561 | 8/2004 |
| WO | WO 2004/065419 | 8/2004 |
| WO | WO 2004/065569 | 8/2004 |
| WO | WO 2004/067561 | 8/2004 |
| WO | WO 2004/068931 | 8/2004 |
| WO | WO 2004/069182 | 8/2004 |
| WO | WO 2004/071408 | 8/2004 |
| WO | WO 2004/072286 | 8/2004 |
| WO | WO 2004/074837 | 9/2004 |
| WO | WO 2004/078140 | 9/2004 |
| WO | WO 2004/085712 | 10/2004 |
| WO | WO 2004/087733 | 10/2004 |
| WO | WO 2004/087735 | 10/2004 |
| WO | WO 2004/090544 | 10/2004 |
| WO | WO 2004/095031 | 11/2004 |
| WO | WO 2004/098631 | 11/2004 |
| WO | WO 2004/104597 | 12/2004 |
| WO | WO 2004/108895 | 12/2004 |
| WO | WO 2004/111250 | 12/2004 |
| WO | WO 2005/000897 | 1/2005 |
| WO | WO 2005/005638 | 1/2005 |
| WO | WO 2005/011599 | 2/2005 |
| WO | WO 2005/012330 | 2/2005 |
| WO | WO 2005/014618 | 2/2005 |
| WO | WO 2005/016236 | 2/2005 |
| WO | WO 2005/018424 | 3/2005 |
| WO | WO 2005/018536 | 3/2005 |
| WO | WO 2005/025516 | 3/2005 |
| WO | WO 2005/025592 | 3/2005 |
| WO | WO 2005/025616 | 3/2005 |
| WO | WO 2005/026360 | 3/2005 |
| WO | WO 2005/027965 | 3/2005 |
| WO | WO 2005/028511 | 3/2005 |
| WO | WO 2005/033142 | 4/2005 |
| WO | WO 2005/033145 | 4/2005 |
| WO | WO 2005/037209 | 4/2005 |
| WO | WO 2005/040212 | 5/2005 |
| WO | WO 2005/041650 | 5/2005 |
| WO | WO 2005/044306 | 5/2005 |
| WO | WO 2005/046605 | 5/2005 |
| WO | WO 2005/047484 | 5/2005 |
| WO | WO 2005/047860 | 5/2005 |
| WO | WO 2005/051998 | 6/2005 |
| WO | WO 2005/052002 | 6/2005 |
| WO | WO 2005/053604 | 6/2005 |
| WO | WO 2005/058815 | 6/2005 |
| WO | WO 2005/058940 | 6/2005 |
| WO | WO 2005/120571 | 7/2005 |
| WO | WO 2005/070965 | 8/2005 |
| WO | WO 2005/072777 | 8/2005 |
| WO | WO 2005/080986 | 9/2005 |
| WO | WO 2005/081872 | 9/2005 |
| WO | WO 2005/090971 | 9/2005 |
| WO | WO 2005/095457 | 10/2005 |
| WO | WO 2005/096730 | 10/2005 |
| WO | WO 2005/100584 | 10/2005 |
| WO | WO 2005/105841 | 11/2005 |
| WO | WO 2005/105847 | 11/2005 |
| WO | WO 2005/105998 | 11/2005 |
| WO | WO 2005/108378 | 11/2005 |
| WO | WO 2005/110056 | 11/2005 |
| WO | WO 2005/123775 | 12/2005 |
| WO | WO 2005/123776 | 12/2005 |
| WO | WO 2006/005588 | 1/2006 |
| WO | WO 2006/005707 | 1/2006 |
| WO | WO 2006/014478 | 2/2006 |
| WO | WO 2006/014638 | 2/2006 |
| WO | WO 2006/015976 | 2/2006 |
| WO | WO 2006/016644 | 2/2006 |
| WO | WO 2006/033688 | 3/2006 |
| WO | WO 2006/036291 | 4/2006 |
| WO | WO 2006/037604 | 4/2006 |
| WO | WO 2006/038729 | 4/2006 |
| WO | WO 2006/039327 | 4/2006 |
| WO | WO 2006/039470 | 4/2006 |
| WO | WO 2006/040153 | 4/2006 |
| WO | WO 2006/041934 | 4/2006 |
| WO | WO 2006/047254 | 5/2006 |
| WO | WO 2006/047670 | 5/2006 |
| WO | WO 2006/050041 | 5/2006 |

(56) References Cited

FOREIGN PATENT DOCUMENTS

| | | |
|---|---|---|
| WO | WO 2006/050667 | 5/2006 |
| WO | WO 2006/052924 | 5/2006 |
| WO | WO 2006/053428 | 5/2006 |
| WO | WO 2006/055178 | 5/2006 |
| WO | WO 2006/066049 | 6/2006 |
| WO | WO 2006/066089 | 6/2006 |
| WO | WO 2006/066118 | 6/2006 |
| WO | WO 2006/066171 | 6/2006 |
| WO | WO 2006/066233 | 6/2006 |
| WO | WO 2006/067792 | 6/2006 |
| WO | WO 2006/069081 | 6/2006 |
| WO | WO 2006/069202 | 6/2006 |
| WO | WO 2006/081171 | 8/2006 |
| WO | WO 2006/083533 | 8/2006 |
| WO | WO 2006/083689 | 8/2006 |
| WO | WO 2006/087550 | 8/2006 |
| WO | 2006094724 | 9/2006 |
| WO | WO 2006/094192 | 9/2006 |
| WO | WO 2006/094724 | 9/2006 |
| WO | WO 2006/095041 | 9/2006 |
| WO | WO 2006/096529 | 9/2006 |
| WO | WO 2006/096653 | 9/2006 |
| WO | WO 2006/099543 | 9/2006 |
| WO | WO 2006/100679 | 9/2006 |
| WO | WO 2006/103116 | 10/2006 |
| WO | WO 2006/110748 | 10/2006 |
| WO | WO 2006/116369 | 11/2006 |
| WO | WO 2006/118959 | 11/2006 |
| WO | WO 2006/119449 | 11/2006 |
| WO | WO 2006/121656 | 11/2006 |
| WO | WO 2006/125830 | 11/2006 |
| WO | WO 2006/128163 | 11/2006 |
| WO | WO 2006/133164 | 12/2006 |
| WO | WO 2006/137354 | 12/2006 |
| WO | WO 2007/005358 | 1/2007 |
| WO | WO 2007/005359 | 1/2007 |
| WO | WO 2007/008547 | 1/2007 |
| WO | WO 2007/011639 | 1/2007 |
| WO | WO 2007/011834 | 1/2007 |
| WO | WO 2007/017686 | 2/2007 |
| WO | WO 2007/019620 | 2/2007 |
| WO | WO 2007/021886 | 2/2007 |
| WO | WO 2007/022416 | 2/2007 |
| WO | WO 2007/040437 | 4/2007 |
| WO | WO 2007/042261 | 4/2007 |
| WO | WO 2007/047967 | 4/2007 |
| WO | WO 2007/047995 | 4/2007 |
| WO | WO 2007/050359 | 5/2007 |
| WO | WO 2007/053661 | 5/2007 |
| WO | WO 2007/059135 | 5/2007 |
| WO | WO 2007/059203 | 5/2007 |
| WO | WO 2007/062088 | 5/2007 |
| WO | WO 2007/062852 | 6/2007 |
| WO | WO 2007/064917 | 6/2007 |
| WO | WO 2007/064919 | 6/2007 |
| WO | WO 2007/064972 | 6/2007 |
| WO | WO 2007/067512 | 6/2007 |
| WO | WO 2007/068411 | 6/2007 |
| WO | WO 2007/068429 | 6/2007 |
| WO | WO 2007/082750 | 7/2007 |
| WO | WO 2007/068412 | 8/2007 |
| WO | WO 2007/088399 | 8/2007 |
| WO | WO 2007/088712 | 8/2007 |
| WO | WO 2007/090872 | 8/2007 |
| WO | WO 2007/092861 | 8/2007 |
| WO | WO 2007/096076 | 8/2007 |
| WO | WO 2007/097251 | 8/2007 |
| WO | WO 2007/098417 | 8/2007 |
| WO | WO 2007/103788 | 9/2007 |
| WO | WO 2007/106617 | 9/2007 |
| WO | WO 2007/108756 | 9/2007 |
| WO | WO 2007/109107 | 9/2007 |
| WO | WO 2007/109749 | 9/2007 |
| WO | WO 2007/112288 | 10/2007 |
| WO | WO 2007/113172 | 10/2007 |
| WO | WO 2007/118984 | 10/2007 |
| WO | WO 2007/119685 | 10/2007 |
| WO | WO 2007/123345 | 11/2007 |
| WO | WO 2007/125351 | 11/2007 |
| WO | WO 2007/127393 | 11/2007 |
| WO | WO 2007/127448 | 11/2007 |
| WO | WO 2007/129457 | 11/2007 |
| WO | WO 2007/144198 | 12/2007 |
| WO | WO 2007/149032 | 12/2007 |
| WO | WO 2008/002893 | 1/2008 |
| WO | WO 2008/008939 | 1/2008 |
| WO | WO 2008/011348 | 1/2008 |
| WO | WO 2008/012101 | 1/2008 |
| WO | WO 2008/015384 | 2/2008 |
| WO | WO 2008/021296 | 2/2008 |
| WO | WO 2008/022349 | 2/2008 |
| WO | WO 2008/027526 | 3/2008 |
| WO | WO 2008/028939 | 3/2008 |
| WO | WO 2008/030251 | 3/2008 |
| WO | WO 2008/030973 | 3/2008 |
| WO | WO 2008/031911 | 3/2008 |
| WO | WO 2008/045962 | 4/2008 |
| WO | WO 2008/047111 | 4/2008 |
| WO | WO 2008/051017 | 5/2008 |
| WO | WO 2008/051326 | 5/2008 |
| WO | WO 2008/057240 | 5/2008 |
| WO | WO 2008/060364 | 5/2008 |
| WO | WO 2008/061795 | 5/2008 |
| WO | WO 2008/064244 | 5/2008 |
| WO | WO 2008/067464 | 6/2008 |
| WO | WO 2008/070229 | 6/2008 |
| WO | WO 2008/071394 | 6/2008 |
| WO | WO 2008/084402 | 7/2008 |
| WO | WO 2008/104385 | 9/2008 |
| WO | WO 2008/104386 | 9/2008 |
| WO | WO 2008/107677 | 9/2008 |
| WO | WO 2008/110885 | 9/2008 |
| WO | WO 2008/122441 | 10/2008 |
| WO | WO 2008/124940 | 10/2008 |
| WO | WO 2008/129023 | 10/2008 |
| WO | WO 2008/130449 | 10/2008 |
| WO | WO 2008/131298 | 10/2008 |
| WO | WO 2008/134034 | 11/2008 |
| WO | WO 2008/143708 | 11/2008 |
| WO | WO 2008/150467 | 12/2008 |
| WO | WO 2008/150946 | 12/2008 |
| WO | WO 2008/150949 | 12/2008 |
| WO | WO 2008/156621 | 12/2008 |
| WO | WO 2008/156622 | 12/2008 |
| WO | WO 2009/008890 | 1/2009 |
| WO | WO 2009/008891 | 1/2009 |
| WO | WO 2009/009768 | 1/2009 |
| WO | WO 2009/044160 | 4/2009 |
| WO | WO 2009/048537 | 4/2009 |
| WO | WO 2009/048538 | 4/2009 |
| WO | WO 2009/048539 | 4/2009 |
| WO | WO 2010/097012 | 9/2010 |

OTHER PUBLICATIONS

Flink MT & Atchison WD. Ca2+ channels as targets of neurological disease: Lambert-Eaton Syndrome and other Ca2+ channelopathies. J. Bioenerg. Biomembr. 2003; 35(6):697-718.*

Hillen H et al. Generation and therapeutic efficacy of highly oligomer-specific beta-amyloid antibodies. J Neurosci. 2010; 30(31):10369-10379.*

Lacor PN et al. Synaptic targeting by Alzheimer's-related amyloid beta oligomers. J. Neurosci. 2004; 24(45):10191-10200.*

Liao YJ et al. Anti-Ca2+ channel antibody attenuates Ca2+ currents and mimics cerebellar ataxia in vivo. Proc. Natl. Acad. Sci. USA, 105(7):2705-2710.*

Chen C. (2005) Beta-Amyloid increases dendritic Ca2+ influx by inhibiting the A-type K+ current in hippocampal CA1 pyramidal neurons. Biochem Biophys Res. Comm. 338:1913-1919.*

Chian P et al. (2003) Protofibrils of amyloid-beta protein inhibit specific K+ currents in neocortical cultures. Neurobiol. Disease, 13:177-190.*

(56) References Cited

OTHER PUBLICATIONS

Jeon D et al. (2007) Impaired long-term memory and long-term potentiation in N-type Ca2+ channel-deficient mice. Genes, Brain Behavior, 6:375-388.*
Lipscombe D et al. (2002) Functional diversity in neuronal voltage-gated calcium channels by alternative splicign of Cav.alpha1. Mol. Neurobiol. 26(1):21-44.*
Rovira C et al. (2002) Abeta(25-35) and Abeta(1-40) act on different calcium channels in CA1 hippocampal neurons. Biochem. Biophys. Res. Comm. 296:1317-1321.*
Shankar GM et al. (2007) Natural oligomers of the Alzheimer amyloid-beta protein induce reversible synapse loss by modulating an NMDA-type glutamate receptor-dependent signaling pathway. J. Neurosci. 27(11):2866-2875.*
Putney, P.W., Calcium Signaling, CRC Press, Inc., 2005.
Buraei, Z., et al., Neuropharmacology, 52, pp. 883-894, 2007.
Yan, Z., et al. J. Physiol., 540, pp. 761-770 (2002).
United States Patent Office Action for U.S. Appl. No. 11/885,362 dated Sep. 26, 2013 (11 pages).
United States Patent Office Notice of Allowance for U.S. Appl. No. 11/574,876 dated Sep. 30, 2013 (11 pages).
United States Patent Office Action for U.S. Appl. No. 13/085,891 dated Nov. 26, 2013 (10 pages).
Aisen, P.S. et al., "The development of anti-amyloid etherapy for Alzheimer's disease: from secretase modulators to polymerisation inhibitors," CNS Drugs (2005) 19(12):989-996.
Albert, S.E. et al., "Time-dependent induction of protective anti-influenza immune responses in human peripheral blood lymphocyte/SCID mice," J. Immunol. (1997) 153(3):1393-1403.
Almquist, R.G. et al., "Synthesis and biological activity of a ketomethylene analogue of a tripeptide inhibitor of angiotensin converting enzyme," J. Med. Chem. (1980) 23:1392-1398.
Altschul, S.F. et la., "Gapped BLAST and PSI_BLAST: a new generation of protein database search programs," Nucl. Acids Res. (1997) 25(17):3389-3402.
Ames, R.S. et al., "Conversion of murine Fabs isolated from a combinatorial phage display library to full length immunoglobulins," J. Immunol. Meth. (1995) 184:177-186.
Arai, K. et al., "An ELISA to determine the biodistribution of human monoclonal antibody in tumor-xenografted SCID mice," J. Immunol Meth. (1998) 217:79-85.
Ardaillou, R., "An Ang II antagonist improves the Alzheimer's disease of the mouse," Medecine/Sciences (2008) 24(1):41.
Arispe, N. et al., "Alzheimer disease amyloid beta protein forms calcium channels in bilayer membranes: blockage by tromethamine and aluminum," Proc. Natl. Acad. Sci. (1993) 90:567-571.
Armstrong, J. et al., "Familial Alzheimer disease associated with A713T mutation in APP," Neurosci. Letters (2004) 370;241-243.
Asakura, K. et al., "Alpha-eudesmol, a P/Q-type Ca2+ channel blocker, inhibits neurogenic vasodilatation and extravasation following electrical stimulation of trigeminal gangion," Brain Res. (2000) 873:94-101, abstract.
Asakura, K. et al., "P/Q-type Ca2+ channel blocker game-agatoxin IVA protects against brain injury after focal ischemia in rats," Brain Res. (1997) 776:140-145, abstract.
Askanas, V. et al., "Inclusion-body myositis: a myodegenerative conformational disorder associated with Abeta, protein misfolding, and proteasome inhibition," Neurology (2006) 66(2) Supp 1:S39-48.
Askanas, V. et al., "Molecular pathology and pathogenesis of inclusion-body myositis," Microscopy Res. Technique (2005) 67:114-120.
Askanas, V. et al., "Proposed pathogenetic cascade of inclusion-body myositis: importance of amyloid-beta, misfolded proteins, predisposing genes, and aging," Curr. Opin. Rheumatol. (2003) 15(6):737-744.
Atherton et al., "The fluorenylmethoxycarbonyl amino protecting group," The Peptides: Analysis, Synthesis, Biology (1987) 9:1-38, Academic Press.
Ausubel, et al., Current Protocols in Molecular Biology (1993) Table of Contents.
Ausubel, F. et al., Short Protocols in molecular biology, 3rd Edition (1995), Table of Contents.
Ausubel, F.M. et al., Current Protocols in Molecular Biology (1989).
Author Guidelines, Journal of Neurochemistry, Version 13, Jun. 2012, 14 pages.
Auvynet, C. et al., "Structural requirements for antimicrobial versus chemoattractant activities for dermaseptin S9," FEBS J. (2008) 2754134-4151.
Awasthi et al., "Amyloid-beta causes apoptosis of newronal cells via caspase cascade, which can be prevented by amyloid-beta-derived short peptides," Exp. Neurology (2005) 196(2):282-289.
Azzazy, H.M.E. et al., "Phage display technology: clinical applications and recent innovations," Clin. Biochem. (2002) 35:425-445.
Babcook, J.S. et al., "A novel strategy for generating monoclonal antibodies from single, isolated lymphocytes producing antibodies of defined specificities," Proc. Natl. Acad. Sci. (1996) 93:7843-7848.
Bagriantsev, S. et al., "Modulation of Abeta SUB 42 low-n oligomerization using a novel yeast reporter system," BMC Biol. (2006) 4:32, 12 pages.
Banker, G.A. et al., "Rat hippocampal neurons in dispersed cell culture," Brain Res. (1977) 126(3):397-425.
Barany, G. et al., "Solid-phase peptide synthesis," in The Peptides: Analysis, Synthesis, Biology, (1980), Academic Press, Gross editor, vol. 2, p. 1-284.
Barbas, III, C.F. et al., "Assembly of combinatorial antibody libraries on phage surfaces: the gene III site," proc. Natl. Acad. Sci. USA (1991) 88:7978-7982.
Barghorn, S. et al., "Globular amyloid beta-peptide 1-42 oligomer—a homogeneous and stable neuropathological protein in Alzheimer's disease," J. Neurochem. (2005) 95(1):834-847.
Barghorn, S. et al., "Abeta-oligomer selective antibody A-887755 exhibits a favorable profile for Alzheimer's disease immunotherapy compared to Abeta-peptide unselective antibodies," Alzheimer's & Dementia: The Journal of the Alzheimer's & Association (2009) 5(4):p. 424.
Barrow, C.J. et al., "Solution conformations and aggregational properties of synthetic amyloid beta-peptides of Alzheimer's disease. Analysis of circular dichroism spectra," J. Mol. Biol. (1992) 225(4):1075-1093.
Bartolini, M. et al., "Insight into the kinetic of amyloid beta (1-42) peptide self-aggregation: elucidation of inhibitors' mechanism of action," Chembiochem. (2007) 8(17):2152-61.
Bateman, D. et al., "Specific binding of Alzheimer amyloid peptides to the cell surface implicates the presence of a membrane receptor," Neurobiol. of Aging (2004) 9th International Conf. on Alzheimers Disease and Related Disorders, Philadelphia, PA, Jul. 17-22, 2004.
Bateman, R.J. et al., "Human amyloid-beta synthesis and clearance rates as measured in cerebrospinal fluid in vivo," Nature Med. (2006) 12(7):856-861.
Bates, K.A. et al., "Clearance mechanisms of Alzheimer's amyloid-Beta peptide: implications for therapeutic design and diagnostic tests," Mol. Psych. (2009) 14(5):469-486.
Bayer, T.A. et al., "Review on the APP/PS1K1 mouse model: intraneuronal A beta accumulation triggers axonopathy, neuron loss and working memory impairment," Genes Brain Behav. (2008) 7:6-11.
Bedzyk, W.D. et al., "Active site structure and antigen binding properties of idiotypically cross-reactive anti-fluorescein monoclonal antibodies," J. Biol. Chem. (1990) 265(1):133-138.
Bell, K.A. et al., MAPK recruitment by beta-amyloid in organotypid hippocampal slice cultures depends on physical state and exposure time, J. Neurochem. (2004) 91(2):349-361.
Belokon, Y.N. et al., "Improved procedures for the synthesis of (S)-2-[N-(N'-benzyl-prolyl)amino]benzophenoe (BPB) and Ni(II) complexes of Schiff's bases derived from BPB and amino acids," Tetrahedron: Asymmetry (1998) 9:4249-4252.
Bendig, "Humanization of rodent monoclonal antibodies by CDR grafting," Methods: A Companion to Methods in Enzymology (1995) 8:83-93.
Benevenuti et al., "Crystallization of soluble proteins in vapor diffusion for xray crystallography," Nature Protocols (2007) 2(7):1633-1651.

(56) References Cited

OTHER PUBLICATIONS

Bennett et al., "Immunization therapy for Alzheimer disease?" Neurology (2005) 64:10-12.
Berman, D.E. et al., "Oligomeric amyloid-beta peptide disrupts phosphatidylinositol-4,5-bisphosphate metabolism," Nat. Neurosci. (2008) 11(5):547-554.
Bernstein, S.L. et al., "Amyloid beta-protein: monomer structure and early aggregation states of Abeta42 and its pro SUP 19 alloform," J. Am. Chem. Soc. (2005) 127(7):2075-2084.
Bernstein, S.L. et al., "Amyloid-beta protein oligomerization and the importance of tetramers and dodecamers in the aetiology of Alzheimer's disease," Nature Chem. (2009) 1:326-331.
Better, M. et al., "*Escherichia coli* secretion of an active chimeric antibody fragment," Science (1988) 240:1041-1043.
Bezprozvanny, I. et al., "Neuronal calcium mishandling and the pathogenesis of Alzheimer's disease," Trends Neurosci. (2008) 31(9):454-463.
Bharadwaj, P. e al., "A new method to measure cellular toxicity of non-fibrillar and fibrillar Alzheimer's Abeta using yeast," J. Alzheimer's Disease (2008) 13(2):147-150.
Bhaskar, K. et al., "The P13K-Akt-mTOR pathway regulates a oligomer induced neuronal cell cycle events," Mol. Neurodegeneration (2009) 4:1.
Bieniarz, C. et al., "Extended length heterobifunctional coupling agents for protein conjugations," Bioconjug. Chem. (1996) 7(1):88-95.
Bird, R.E. et al., "Single-chain antigen-binding proteins," Science (1988) 242:423-426.
Birren, B. et al., Genome Analysis—A Laboratory Manual, vols. 1 & 2, Table of Contents (1998).
Bitan, G. et al., "A molecular switch in amyloid assembly: met35 and amyloid beta-protein oligomerization," J. Am. Chem. Soc. (2003) 125:15359-15365.
Bitan, G. et al., "Amyloid beta-protein (Abeta) assembly: Abeta40 and Abeta42 oligomerize through distinct pathways," Proc. Natl. Acad. Sci. USA (2003) 100(1):330-335.
Bitan, G. et al., "Primary-quaternary structure relationships controlling early A beta oligomerizationpeptide revolution: genomics, proteomics and therapeutics," 18th American Peptide Symposium, Boston, MA Jul. 19-23, 2003, 765-767.
Bitan, G. et al., "Towards inhibition of amyloid beta-protein oligomerization," Biopolymers (2005) 80573, 19th American Peptide Symposium, San Diego, CA Jun. 18-23, 2005.
Bobich, J.A. et al., "Incubation of nerve endings with a physiological concentration of Abeta SUB 1-42 activates CaV2.2(N-type)-voltage operated calcium channels and acutely increases glutamate and noradrenaline release," J. Alzheimer's Dis. (2004) 6(3):243-255.
Bocher, W.O. et al., "Antigen-specific B and T cells in human/ouse radiation chimera following immunization in vivo," Immunol (1999) 96:634-641.
Bombil, F. et al., "A promising model of primaray human immunization in human-scid mouse," Immuolbiol. (1996) 195:360-375.
Boridy, S. et al., "The binding of pullalan modified cholesteryl nanogels to Abeta oligomers and their suppression of cytotoxicity," Biomaterials (2009) 30(29):5583-5591.
Boss, M.A. et al., "Genetically engineered antibodies," Immunol (1985) 6(1):12-13.
Boutaud, O. et al., "PGH SUB 2-derived levuglandin adducts increase the neurotoxicity of amyloid beta 1-42," J. Neurochem. (2006) 96(4):917-923.
Boutaud, O. et al., "Prostaglandin H2 (PGH2) accelerates formation of amyloid beta1-42 oligomers," J. Neurochem. (2002) 82:1003-1006.
Boyd-Kimball, D. et al., "Neurotoxicity and oxidative stress in D1M-substituted Alzheimer's Abeta(1-42): relevance to N-terminal methionine chemistry in small model peptides," Peptides (2005) 26:665-673.
Bravo, R. et al., "Sulfated polysaccharides promote the assembly of amyloid beta 1-42 peptide into stable fibrils of reduced cytotoicity," J. Biol. Chem. (2008) 283:32471-32483.

Brettschneider, S. et al., "Decreased serum amyloid Beta1-42 autoantibody levels in Alzheimer's disease, determined by a newly developed immuno-precipitation assay with radiolabeled amyloid beta1-42 peptide," Biol. Psychiatry (2005) 57:813-816.
Brinkley, M.A., "A survey of methods for preparing protein conjugates with dyes, haptens and crosslinking reagents," Bioconjugate Chem. (1992) 3:2-13.
Brinkman, U. et al., "Phage display of disulfide-stabilized FV fragments," J. Immunol Meth. (1995) 182:41-50.
Britschgi, M. et al., "Neuroprotective natural antibodies to assemblies of amyloidogenic peptides decrease with normal aging and advancing Alzheimer's disease," Proc. Natl. Acad. Sci. USA (2009) 106(29):12145-12150.
Brorson et al., "Mutational analysis of avidity and fine specificity of anti-levan antibodies," J. Immunol (1999) 163:6694-6701.
Brown, J.P. et al., "Protein antigens of normal and malignant human cells identified by immunoprecipitation with monoclonal antibodies," J. Biol. Chem. (1980) 255(11):4980-4983.
Brown, J.P. et al., "Structural characterization of human melanoma-associated antigen p97 with monoclonal antibodies," J. Immunol (1981) 127(2):539-546.
Brummell et al., "Probing the combining site of an anti-carbohydrate antibody by saturation-mutagenesis: role of the heavy-chain CDR3 residues," Biochem. (1993) 32:1180-1187.
Brunger et al., "Crystallography and NMR system: a new software suite for macromolecular structure determination," Acta Crystallogr. (1998) D54(Pt5):905-921.
Brutlag, D. "Computational Molecular Biology—Multiple Sequence Alignment," (2007).
Buchwald, H. et al., "Long-term continuous intravenous heparin administration by an implantable infusion pump in ambulatory patients with recurrent venous thrombosis," Surgery (1980) 88:507-516.
Buraei, Z. et al., "Roscovitine differentially affects CaV2 and Kv channels by binding to the open state," Neuropharmacology (2007) 52:883-894.
Burks et al., "In vitro scanning saturation mutagenesis of an antibody binding pocket," Proc. Natl. Acad. Sci. USA (1997) 94:412-417.
Burton, D.R. et al., "Human antibodies from combinatorial libraries," Adv. In Immunol (1994) 57:191-208.
Butler, D. et al., "Cellular responses to protein accumulation involve autophagy and lysosomal enzyme activation," Rejuvenation Res. (2005) 8(4):227-237.
Carlsson, J. et al., "Protein thiolation and reversible protein-protein conjugation. N-succinimidyl 3-(2-pyridyldithio) propionate, a new heterobifunctional reagent," Biochem. J. (1978) 173(3):723-737.
Carter, D.A. et al., "More missense in amyloid gene," Nat. Genet. (1992) 2:255-256.
Carter, P. et al., "Humanization of an anti-p185HER2 antibody for human cancer therapy," Proc. Natl. Acad.Sci. (1992) 89:4285-4289.
Casset et al., "A peptide mimetic of an anti-CD4 monoclonal antibody by rational design," Biochem. Biophys. Res. Comm. (2003) 307:198-205.
Catterall, W.A. et al., "International Union of Pharmacology. XLVIII. Nomenclature and structure-function relationships of voltage-gated calcium channels," Pharm. Rev. (2005) 57(4):411-425.
Cecchini, C. et al., "Increased susceptibility to amyloid toxicity in familial Alzheimer's fibroblasts," Neurobiol. Aging (2007) 28(6):863-876.
Cecchini, M. et al., "A molecular dynamics approach to the structural characterization of amyloid aggregation," J. Mol. Biol. (2006) 357(4):1306-1321.
Chacon, M.A. et al., "Frizzled-1 is involved in he neuroprotective effect of Wnt3a against Abeta oligomers," J. Cell. Physiol. (2008) 217(1):215-227.
Chaiken, I.M., "Semisynthetic peptides and proteins," CRC Crit. Rev. Biochem. (1981) 11(3):255-301.
Chamat, S. et al., "Human monoclonal antibodies isolated from spontaneous Epstein-Barr virus-transformed tumors of Hu-SPL-SCID mice and specific for fusion protein display broad neutralizing activity toward respiratory syncytial virus," J. Infect. Dis. (1999) 180:268-277.

(56) References Cited

OTHER PUBLICATIONS

Chander, H. et al., "Binding of trypsin to fibrililar amyloid beta-protein," Brain Res. (2006) 1082(1):173-181.
Chang, L. et al., "Femtomole immunodetection of synthetic and endogenous amyloid-beta oligomers and its application to Alzheimer's disease drug candidate screening," J. Mol. Neurosci. (2003) 20(3):305-313.
Chanki, H. et al., "Ex situ atomic force microscopy analysis of beta-amyloid self-assembly and deposition on a synthetic template," Langmuir (2006) 16(22):6977-6985.
Chen et al., "Selection and analysis of an optimized anti-VEGF antibody: crystal structure of an affinity-matured Fab in complex with antigen," J. Mol. Biol. (1999) 293:865-881.
Chen, K. et al., "Cooperation between NOD2 and toll-like receptor 2 ligands in the up-regulation of mouse mFPR2, a G-protein-coupled Aalpha SUB 42 peptide receptor, in microglial cells," J. Leukocyte Biol. (2008) 83(6):1467-1475.
Chen, Y-R. et al., "Distinct early folding and aggregation properties of Alzheimer amyloid-beta peptides A beta 40 and A beta 42—stable trimer or tetramer formation by A beta 42," J. Biol. Chem. (2006) 281:24414-24422.
Chiang, H-C. et al., "Distinctive roles of different beta-amyloid 42 aggregates in modulation of synaptic functions," FASEB Journal (2009) 23(6):1969-1977.
Chiang, P.K. et al., "The many faces of amyloid beta in Alzheimer's disease," Curr. Mol. Med. (2008) 8(6):580-584.
Chiarini, A. et al., "Calcium-sensing receptor (CaSR) in human brain's pathophysiology: roles in late-onset Alzheimer's disease (LOAD)," Curr. Pharma. Biotech. (2009) 10(3):317-326.
Choo-Smith, LP et al., "The interaction between Alzheimer amyloid beta (1-40) peptide and ganglioside Gmi-containing membranes," FEBS Lett. (1997) 402:95-98.
Chothia, C. et al., "Canonical structures for the hypervariable regions of immunoglobulins," J. Mol. Biol. (1987) 196:901-917.
Chothia, C. et al., "Conformations of immunoglobulin hypervariable regions," Nature (1989) 342:877-883.
Chothia, C. et al., "Structural repertoire of the human VH segments," J. Mol. Biol. (1992) 227:799-817.
Chrisey, L. et al., "Covalent attachment of synthetic DNA to self-assembled monolayer films," Nucl. Acids. Res. (1996) 24(15):3031-3039.
Christensen, D.D., "Changing the course of Alzheimer's disease: anti-amyloid disease-modifying treatments on the horizon," Primary Care Companion J. Clin. Psych. (2007) 9(1):32-41.
Chromy et al., "Oligomer/conformation-dependent Abeta antibodies," Abstracts of the Annual Meeting of the Society for Neuroscience (2000) 26(1-2):4.
Chromy, B. et al., "Self-assembly of a beta 1-42 into globular neurotoxins," Biochem. (2003) 42(17):12749-12760.
Chromy, B.A. et al., "Stability of small oligomers of Abeta1-42( ADDLs)," Society for Neuroscience Abstracts (1999) Abstract No. 252129, 29th Annual Meeting of the Society for Neuroscience, Miami Beach, FL, Oct. 23-28, 1999.
Chung, H. et al., "Degradation of beta-amyloid peptide by microglia," Society for Neuroscience Abstracts (2000) 26 Abstract No. 858.10, 30th Annual Meeting of the Society of Neuroscience, New Orleans, LA, Nov. 4-9, 2000.
Ciccotosto, G.B. et al., "Methionine oxidation: implications for the mechanism of toxicity of the beta-amyloid peptide from Alzheimer's disease," Lett. Peptide Sci. (2003) 10(5-6):413-417.
Citron, M., "Alzheimer's disease: strategies for disease modification," Nature Reviews Drug Discovery (2010) 9:387-398.
Clackson, T. et al., "Making antibody fragments using phage display libraries," Nature (1991) 352:624-628.
Clark, M.S., Plant Molecular Biology—A Laboratory Manual, Table of Contents (1997).
Cleary, J.P. et al., "Cognitive effects of oligomeric and fibril Abeta in rats," Soc. for Neuroscience Abstract Viewer and Itinerary Planner (2002) Abstract No. 882.2, 32nd Annual meeting of the Society for Neuroscience, Orlando, FL, Nov. 2-7, 2002.

Cleek, R.L. et al., "Biodegradable polymeric carriers for a bFGF antibody for cardiovascular application," Proc. Intl. Symp. Control. Re. Bioact. Mater. (1997) 24:853-854.
Co, M.S. et al., "Genetically engineered deglycosylation of the variable domain increases the affinity of anti-Cd33 monoclonal antibody," Molec. Immunol. (1993) 30(15):1361-1367.
Cole, G.M. et al., "Alzheimer's amyloid story finds its star," Trends Mol. Med. (2006) 12(9):395-396.
Cole, G.M. et al., "Cat and mouse," Neuron (2006) 51(6):671-672.
Cole, G.M. et al., "Docosahexaenoic acid protecs from amyloid and dendritic pathology in an Alzheimer's disease mouse model," Nutrition and Health (2006) 18(3):249-259.
Cole, M.S. et al., "Human IgG2 variants of chimmeric anti-CD3 are nonmitogenic to T cells," J. Immunol (1997) 159(7):3613-3621.
Colman, P.M., "Effects of amino acid sequence changes on antibody-antigen interactions," Research in Immunol (1994) 145:33-36.
Colombo, R. et al., "CE can identify small molecules that selectively target soluble oligomers of amyloid beta protein and display antifibrillogenic activity," Electrophoresis (2009) 30(8):1418-1429.
Co-Pending U.S. Appl. No. 13/893,780, filed May 14, 2013.
Co-Pending U.S. Appl. No. 13/862,865, filed Apr. 15, 2013.
Costantini, C. et al., "The expression of p75 neurotrophin receptor protects against the neurotoxicity of soluble oligomers of beta-amyloid," Exp. Cell Res. (2005) 311(1):126-134.
Craft, J.M. et al., "Enhanced susceptibility of S-100B transgenic mice to neuroinflammation and neuronal dysfunction induced by intracerebroventricular infusion of human beta-amyloid," Glia (2005) 51(3):209-216.
Crouch, P.J. et al., "Soluble oligomeric amyloid beta 1-42 specifically inhibits cytochrome c oxidase of human mitochondria," Mitochondrial Medicine (2004) 4:71-72.
Crouse, N.R. et al., "Oligomeric amyloid-beta(1-42) induces THP-1 human monocyte adhesion and maturation," Brain Res. (2009) 1254:109-119.
Dahlgren, K.N. et al., "Oligomeric and fibrillar species of amyloid-beta peptides differentially affect neuronal viability," J. Biol. Chem. (2002) 277(35):32046-32053.
Das, U. et al., "Interface peptide of Alzheimer's amyloid beta: application in purification," Biochem. Biophys. Res. Commun. (2007) 362(2):538-542.
Dasilva, K.A. et al., "Reduced oligomeric and vascular amyloid-beta following immunization of TgCRND8 mice with an Alzheimer's DNA vaccine," Vaccine (2009) 27136-1376.
De Felice, F.G. et al., "Alzheimer's disease-type neuronal tau hyperphosphorylation induced by Abeta oligomers," Neurobiol. Aging (2008) 29(9):1334-1347.
De Pascalis, R. et al., "Grafting of 'abbreviated' complementarity-determining regions containing specificity-determining residues essential for ligand contact to engineer a less immunogenic humanized monoclonal antibody," J. Immunol (2002) 169:3076-3084.
Dealmeida, E.R.P. et al., "Transgenic expression of two marker genes under the control of an arabidopsis rbcS promoter: sequences encoding the Rubisco transit peptide increase expression levels," Mol Gen. Genet. (1989) 218:78-86.
deChaves, P.E. et al., "Lipid rafts in amyloid beta endocytosis and amyloid beta-induced apoptosis," J. Neurochem. (2009) 110(2):146, S20-23.
DeMattos et al., "P4-358 in vitro and in vivo characterization of beta-amyloid antibodies binding to cerebral amyloid angiopathy (CAA) and the selective exacerbation of CAA-associated microhemorrhage," Neurobiol. Aging (2004) 25(S2):S577.
DeMattos, R.B. et al., "Peripheral anti-Abeta antibody alters CNS and plasma Abeta clearance and decreases brain Abeta burden in a mouse model of Alzheimer's disease," Proc. Natl. Acad. Sci. USA (2001) 98(15):8850-8855.
Demeester, N. et al., "Comparison of the aggregation properties, secondary structure and apoptotic effects of wild-type, Flemish and Dutch N-terminally truncated amyloid beta peptides," Euro. J. Neurosci. (2001) 13(11):2015-2024.
Demuro, A. et al., "Calcium dysregulation and membrane disruption as a ubiquitous neurotoxic mechanism of soluble amyloid oligomers," J. Biol. Chem. (2005) 280(17):17294-17300.

(56) References Cited

OTHER PUBLICATIONS

Denkewalter et al., "Fortschritte der arzneimittelforschung progress in drug research progres des receherches pharmaceutiques," (1996) 10:224-285.
Dewachter, I. et al., "Neuronal deficiency of presenillin 1 inhibits amyloid plaque formation and corrects hippocampal long-term potentiation but not a cognitive defect of amyloid precursor protein [V717I] transgenic mice," J. Neurosci. (2002) 22(9):3445-3453.
Dickson, D.W. et al., "Correlations of synaptic and pathological markers with cognition of the elderly," Neurobiol. Aging (1995) 16(3):285-304.
Dillen, K. et al., "A two decade contribution of molecular cell biology to the centennial of Alzheimer's disease: are we progressing toward therapy?" Int. Rev. Cytol. (2006) 254:215-300.
Dingledine, R. et al., Brain slices, Plenum Press (1984) Table of Contents.
Donnet et al., "Plasma treatment effect on the surface energy of carbon and carbon fibers," Carbon (1986) 24(6):757-770.
Du, Y. et al., "Reduced levels of amyloid beta-peptide antibody in Alzheimer disease," Neurology (2001) 57:801-805.
Dufner, P. et al., "Harnessing phage and ribosome display for antibody optimisation," Trends Biotech. (2006) 24(11):523-529.
During, M.J. et al., "Controlled release of dopamine from a polymeric brain implant: in vivo characterization," Ann. Neurol. (1989) 25:351-356.
Durocher, Y. et al., "High-level and high-throughput recombinant protein prouction by transient transfection of suspension-growing human 293-EBNA1 cells," Nucl. Acid. Res. (2002) 30(2):e9-11.
Eckenhoff, R.G. et al., "Anesthetics and neurodegenerative disorders: a molecular basis for concern?" Anesthesiology Abstracts of Scientific Papers Annual Meeting, 2003, Abstract No. A-848, 2003 Annual Meeting of the American Society of Anesthesiologists, San Francisco, CA, Oct. 11-15, 2003.
Eckert, A. et al., "Oligomeric and fibrillar species of beta-amyloid (A beta 42) both impair mitochondrial function in P301L tau transgenic mice," J. Mol. Med. (2008) 86(11):1255-67.
Eisenberg et al., "Analysis of membrane and surface protein sequences with the hydrophobic moment plot," J. Mol. Biol. (1984) 179(1):125-142.
Englund, H. et al., Oligomerization partially explains the lowering of A beta 42 in Alzheimer's disease cerebrospinal fluid, Neurodegenerative Dis. (2009) 6:139-147.
Eren, R. et al., "Human monoclonal antibodies specific to hepatitis B virus generated in a human/mouse radiation chimera: the Trimera system," Immunol. (1998) 93:154-161.
Esteras-Chopo, A. et al., "New strategy for the generation of specific D-peptide amyloid inhibitors," J. Mol. Biol. (2008) 377:1372-1381.
Evans et al., "Design of a nonpeptidal ligands for a peptide receptor: cholecystokinin antagonists," J. Med. Chem. (1987) 30:1229.
Evans, C.G. et al., "Heat shock proteins 70 and 90 inhibit early stages of amyloid beta-(1-42) aggregation in vitro," J. Biol. Chem. (2006) 281:33182-33191.
Evans, N.A. et al., "Abeta SUB 1-42 reduces synapse number and inhibits neurite outgrowth in primary cortical and hippocampal neurons: a quantitative analysis," J. Neurosci. Methods (2008) 175(1):96-103.
Evin, G., "Gamma-secretase modulators: hopes and setbacks for the future of Alzheimer's treatment," Expert Rev. Neurother. (2008) 8(11):1611-1613.
Fauchere, "Elements for the rational design of peptide drugs," Adv. Drug Res. (1986) 15:29-69.
Feld, M. et al., "Effect on memory of acute administration of naturally secreted fibrils and synthetic amyloid-beta peptides in an invertebrate model," Neurobiol. Learn. Mem. (2008) 89(4):407-418.
Ferrao-Gonzales, A et al., "Controlling beta-amyloid oligomerization by the use of naphthalene sulfonates: trapping low molecular weight oligomeric species," J. Biol. Chem. (2005) 280(41):34747-34754.
Fishwild, D.M. et al., "High-avidity human IgGx monoclonal antibodies from a novel strain of minilocus transgenic mice," Nature Biotech. (1996) 14:845-851.
Flink, M.T. et al., "Ca2+ channels as targets of neurolgoical disease: Lambert-Eaton Syndrome and other Ca2+ channelopathies," J. Bioeng. Biomembr. (2003) 35(6):697-718.
Foote, J. et al., "Antibody framework residues affecting the conformation of the hypervariable loops," J. Mol. Biol. (1992) 224:487-499.
Forsell, C. et al., "Amyloid precursor protein mutation at codon 713 (Ala→Val) does not cause schizophrenia: non-pathogenic variant found at codon 705 (silent)," Neurosci. Lett. (1995) 184:90-93.
Fradinger, E.A. et al., "C-terminal peptides coassemble into Abeta42 oligomers and protect neurons against Abeta42-induced neurotoxicity," Proc. Natl. Acad. Sci. USA (2008) 105(37):14175-14180.
Fuchs, P. et al., "Targeting recombinant antibodies to the surface of *Escherichia coli*: fusion to a peptidoglycan associated lipoprotein," BioTech. (1991) 9:1369-1372.
Funke, S.A. et al., "Detection of amyloid-beta aggregates in body fluids: a suitable method for early diagnosis of Alzheimer's disease?" Current Alzheimer's Research (2009) 6(3):285-289.
Galfre, G. et al., "Antibodies to major histocompatibility antigens produced by hybrid cell lines," Nature (1977) 266(5602):550-552.
Gallo, M.L. et al., "The human immunoglobulin loci introduced into mice: V(D) and J gene segment usage similar to that of adult humans," Eur. J. Immunol (2000) 30:534-540.
Garrard, L.J. et al., "FAB assembly and enrichment in a monovalent phage display system," BioTech. (1991) 9:1373-1377.
Garzon, D.J. et al., "Oligomeric amyloid decreases basal levels of brain-derived neurotrophic factor (BDNF) mRNA via specific downregulation of BDNF transcripts IV and V in differentiated human neuroblastoma cells," J. Neurosci. (2007) 27(10):2628-2635.
Gavilondo, J.V. et al., "Antibody engineering at the millennium," BioTechniques (2002) 29:128-145.
Gefter, M.L. et al., "A simple method for polyethylene glycol-promoted hybridization of mouse myeloma cells," Somatic Cell Genetics (1997) 3(2):231-236.
Gellermann, G.P. et al., "Abeta-globulomers are formed independently of the fibril pathway," Neurobiol. of Dis. (2008) 30(2):212-220.
Gervais, F. et al., "Targeting soluble Abeta peptide with tramiprosate for the treatment of brain amyloidosis," Neurobiol. Aging (2007) 28(4):537-547.
Ghiso, J. et al., "Systemic catabolism of Alzheimer's Abeta40 and Abeta42," J. Biol. Chem. (2004) 279:45897-45908.
Ghosal, K. et al., "Alzheimer's disease-like pathological features in transgenic mice expressing the APP intracellular domain," Proc. Natl. Acad. Sci. (2009) 106(43):18367-18372.
Giacobini, E. et al., "One hundred years after the discovery of Alzheimer's disease. A turning point for therapy? The multifaceted aspects of Alzheimer's disease: from social to molecular problems," J. Alzheimer's Disease (2007) 12(1):37-52.
Gibbs, M.E. et al., "Rescue of Abeta SUB 1-42-induced memory impairment in day-old chick by facilitation of astrocytic oxidative metabolism: implications for Alzheimer's disease," J. Neurochem. (2009) 109 Suppl. 1:230-236.
Giege, R. et al., "An introduction to the crystallogenesis of biological macromolecules," Crystallization of Nucleic Acids & Proteins, a Practical Approach, 2nd Edition: 1-16 (1999).
Giliberto, L. et al., "Mutant presenilin 1 increases the expression and activity of BACE1," J. Biol. Chem. (2009) 284(14):9027-9038.
Gillies, S.D. et al., "High-level expression of chimeric antibodies using adapted cDNA variable region cassettes," J. Immunol Meth. (1989) 125:191-202.
Giuffrida, M.L. et al., "A beta(25-35) and its C- and/or N-blocked derivatives: copper driven structural features and neurotoxicity," J. Neursci. Res. (2007) 85:623-633.
Giuffrida, M.L. et al., "Beta-amyloid monomers are neuroprotective," J. Neurosci. (2009) 29(34):10582-10587.
Goeddel, D., "Systems for heterologous gene expression," Meth. in Enzymol. (1990) 185:3-7.
Goldspiel, B.R. et al., "Human gene therapy," Clin. Pharm. (1993) 12:488-505.

(56) References Cited

OTHER PUBLICATIONS

Gong, Y. et al., "Abeta-derived diffusible ligands in Alzheimer's disease brain as therapeutic antibody targets," Abstracts of the Annual Meeting of the Society of Neuroscience (2002) 1 page.

Gong, Y., "Alzheimer's disease-affected brain: presence of oligomeric A ligands (ADDLs) suggests a molecular basis for reversible memory loss," Proc. Natl. Acad. Sci. (2003) 100(18):10417-10422.

Gonzalo-Ruiz, A. et al., "Oligomers of beta-amyloid (1-42) peptide induce co-localization of AB and TAU proteins associated with calpain activity," J. Neurochem. (2009) 110:57-58.

Goodson, J.M., "Dental applications" in Medical Applications of Controlled Release, (1984) vol. II, Chapter 6, 115-138.

Gowing, E. et al., "Chemical characterization of A beta 17-42 peptide, a component of diffuse amyloid deposits of Alzheimer disease," J. Biol. Chem. (1994) 269:10987-10988.

Grabarek, Z. et al., "Zero-length crosslinking procedure with the use of active esters," Anal. Biochem. (1990) 185(1):131-135.

Grabowski, T.J. et al., "Novel amyloid precursor protein mutation in an Iowa family with dementia and severe cerebral amyloid angiopathy," Ann. Neurol. (2001) 49(6):697-705.

Grace, S.Y. et al., "Abeta induces oxidative-degradative stress through NADPH oxidase and phopholipase A2," J. Neurochem. (2009) 110222, 22nd Biennial Meeting of the International Society of Neurochemistry, South Korea, Aug. 23-29, 2009.

Gram, H. et al., "In vitro selection and affinity maturation of antibodies from a naïve combinatorial immunoglobulin library," Proc. Natl. Acad. Sci. USA (1992) 89:3576-3580.

Grange, P.De La. et al., "Fast DB: a website resource for the study of the expression regulation of human gene products," Nucl. Acids Res. (2005) 33(13):4276-4284.

Green, L.L. et al., "Antigen-specific human monoclonal antibodies from mice engineered with human Ig heavy and light chain YACs," Nature Genetics (1994) 7(1):13-21.

Green, L.L. et al., "Regulation of B cell development by variable gene complexity in mice reconstituted with human immunoglobulin yeast artificial chromosomes," J. Exp. Med. (1998) 188(3):483-495.

Green, L.L., "Antibody engineering via genetic engineering of the mouse: XenoMouse strains are a vehicle for the facile generation of therapeutic human monoclonal antibodies," J. Immunol Meth. (1999) 231:11-23.

Griffiths, A.D. et al., "Human anti-self antibodies with high specificity from phage display libraries," The EMBO Journal (1993) 12(2):725-734.

Guo, L. et al., "APOE down regulates pro-inflammatory responses induced by oligomeric Abeta in activated glia," Soc. for Neurosci. Abstract Viewer and Itinerary Planner (2002), Abstract No. 883.12, 32nd Annual meeting of the Society for Neuroscience, Orlando, FL, Nov. 2-7, 2002.

Ha, C. et al., "Ex situ atomic force microscopy analysis of beta-amyloid self-assembly and deposition on a synthetic template," Langmuir (2006) 22:6977-6985.

Ha, C. et al., "Metal ions differntially influence the aggregation and deposition of Alzheimer's beta-amyloid on a solid template," Biochem. (2007) 46(20):6118-6125.

Ha, H.J. et al., "Development of herbal medicine for Alzheimer's disease from RHEI rhizoma," J. Neurochem. (2009) 110114.

Haass, C. et al., "Soluble protein oligomers in neurodegeneration: lessons from the Alzheimer's amyloid beta-peptide," Nat. Rev. Mol. Cell Biol. (2007) 8(2):101-112.

Hachiya, N.S. et al., "Oligomeric Aip2p/Dld2p modifies the protein conformation of both properly folded and misfolded substrates in vitro," Biochem. Biophys. Res. Comm. (2004) 323(1):339-344.

Hagemeyer, C.E. et al., "Single-chain antibodies as diagnostic tools and therapeutic agents," Thromb. Haemost. (2009) 101:1012-1019.

Halladay, M.W. et al., "Synthesis of hydroxyethelene and ketomethylene dipeptide isosteres," Tetrahedron Lett. (1983) 24:4401-4404.

Hann, M.M., "On the double bond isostere of the peptide bond: preparation of an enkephalin analogue," J. Chem. Soc. Perkin Transactions (1982) 1:307-314.

Harding, F.A. et al., "Class switching in human immunoglobulin transgenic mice," Ann. N.Y. Acad. Sci. (1995) 764:536-546.

Hardy, J. et al., "The amyloid hypothesis of Alzheimer's disease: progress and problems on the road to therapeutics," Science (2002) 297:353-356.

Harris-White, M.E. et al., "Effects of low dose, low MW soluble amyloid oligomers on spatial memory performance," Society for Neurosci. Abstr. Viewer and Itin. Plann. (2003) Abstract No. 240.11, 33rd Annual Meeting of the Society of Neuroscience, Nov. 8-12, 2003, New Orleans.

Hartley, D.M. et al., "Transglutaminase induces protofibril-like amyloid beta-protein assemblies that are protease-resistant and inhibit long-term potentiation," J. Biol. Chem. (2008) 283(24):16790-16800.

Hashida, S. et al., "More useful maleimide compounds for the conjugation of Fab to horseradish peroxidase through thiol groups in the hinge," J. Appl. Biochem. (1984) 6:56-63.

Hashimoto, M. et al., "Role of protein aggregation in mitochondrial dysfunction and neurodegeneration in Alzheimer's and Parkinson's disease," Neuromol. Med. (2003) 4(1-2):21-36.

Hawkins, R.E., "Selection of phage antibodies by binding affinity—imicking affinity maturation," J. Mol. Biol. (1992) 226:889-896.

Hay, B.N. et al., "Bacteriophage cloning and *Escherichia coli* expression of a human IgM fab," Hum. Antibod. Hybridomas (1992) 3:81-85.

Hayes, G.M. et al., "Production of beta-amyloid by primary human foetal mixed brain cell cultures and its modulation by exogenous soluble beta-amyloid," Neurosci. (2002) 113(3):641-646.

Head, E. et al., "A two-year study with fibrillar beta-amyloid (Abeta) immunization in aged canines: effects on cognitive function and brain Abeta," J. Neurosci. (2008) 28(14):3555-3566.

Head, E. et al., "The efffects of immunization with fibrillar or oligomeric Abeta in the brain and CSF of aged canines: a pilot study," Society for Neuroscience Abstract Viewer and Itinerary Planner (2003) Abstract No. 525.24, 33rd Annual Meeting of the Society of Neuroscience, New Orleans, LA, Nov. 8-12, 2003.

Heard, C. et al., "Two neutralizing human anti-RSV antibodies: cloning, expression, and characterization," Molec. Med. (1999) 5:35-45.

Heinitz, K. et al., "Toxicity mediated by soluble oligomers of beta-amyloid(1-42) on cholinergic SN56.B5.G4 cells," J. Neurochem. 92006) 98(6):1930-1945.

Helisalmi, S. et al., "Screening for amyloid beta precursor protein codon 665, 670/671 and 717 mutations in Finnish patients with Alzheimer's disease," Neurosci. Lett. (1996) 205:68-70.

Herz, U. et al., "The humanized (Hu-PBMC) SCID mouse as an in vivo model for human IgE production and allergic inflammation of the skin," Int. Arch Allergy Immunol. (1997) 113(1-3):150-152.

Hess et al., "Cooperation of glycolytic enzymes," J. Adv. Enzyme Reg. (1968) 7:149-167.

Hieter, P.A. et al., "Evolution of human immunoglobulin kJ region genes," J. Biol. Chem. (1982) 257(3):1516-1522.

Higgins, D.G. et al., "Fast and sensitive multiple sequence alignments on a microcomputer," CABIOS Comm. (1989) 5(2):151-153.

Higuchi, R., "Using PCR to engineer DNA," PCR Technol: Princ. & Appl. for DNA Amplification (1989) 61-70.

Hilbich, C. et al., "Aggregation and secondary structure of synthetic amyloid betaA4 peptides of Alzheimer's disease," J. Mol. Biol. (1991) 218:149-163.

Hillen, H. et al., "Generation and therapeutic efficacy of highly oligomer-specific beta-amyloid antibodies," J. Neurosci. (2010) 30(31):10369-10379.

Hirko, A.C. et al., "Peripheral transgene expression of plasma gelsolin reduces amyloid in transgenic mouse models of Alzheimer's disease," Mol. Ther. (2007) 15(9):1623-9.

Hock, C. et al., "Clinical observations with AN-1792 using TAPIR analyses," Neurodegenerative Dis. (2006) 2(5):273-276.

Holliger, P. et al., "Diabodies small bivalent and bispecific antibody fragments," Proc. Natl. Acad. Sci. (1993) 90:6444-6448.

(56) References Cited

OTHER PUBLICATIONS

Holm et al., "Functional mapping and single chain construction of the anti-cytokeratin 8 monoclonal antibody TS1," Mol. Immunol (2007) 44:1075-1084.

Hong, H-S. et al., "Combining the rapid MTT formazan exocytosis assay and the MC65 protection assay led to the discovery of carbozole analogs as small molecule inhibitors of Abeta oligomer-induced cytotoxicity," Brain Res. (2007) 1130(1):223-234.

Hong, H-S. et al, "Inhibition of Alzheimer's amyloid toxocity with a tricyclic pyrone molecule in vitro and in vivo," J. Neurochem. (2009) 108(4):1097-1108.

Hoogenboom, H.R. et al., "Multi-subunit proteins on the surface of silamentous phage: methodologies for displaying antibody (Fab) heavy and light chains," Nucl. Acids Res. (1991) 19(15):4133-4137.

Hoogenboom, H.R. et al., "Natural and designer binding sites made by phage display technology," Immunol Today (2000) 21(8):371-378.

Hoogenboom, H.R., "Designing and optimizing library selection strategies for generating high-affinity antibodies," Tibtech (1997) 15:62-70.

Hoozemans, J.J.M. et al., "Always around, never the same: pathways of amyloid beta induced neurodegeneration throughout the pathogenic cascade of Alzheimer's disease," Curr. Med. Chem. (2006) 13(22):2599-2605.

Hossain, S. et al., "Mechanism of docosahexaenoic acid-induced inhibition of in vitro Abeta1-42 fibrillation and Abeta1-42-induced toxicity in SH-S5Y5 cells," J. Neurochem. (2009) 111(2):568-579.

Howard III, M.A. et al., "Intracerebral drug delivery in rats with lesion-induced memory deficits," J. Neurosurg. (1989) 71:105-112.

Howlett, D.R. et al., "The pathology of APP transgenic mice: a model of Alzheimer's disease or simply overexpression of APP?" Histol. Histopathol. (2009) 24(1):83-100.

Hoyer, W. et al., "Stabilization of a beta-hairpin in monomeric Alzheimer's amyloid-beta peptide inhibits amyloid formation," Natl. Acad. Sci. Proc. Natl. Acad. Sci. (2008) 105(13):5099-5104.

Hruby, V.J., "Conformational restrictions of biologically active peptides via amino acid side chain groups," Life Sci. (1982) 31:189-199.

Hsiao et al., "Correlative memory deficits, abeta elevation, and amyloid plaques in transgenic mice," Science (1996) 274(5284):99-102.

Huang, C. et al., "Isoproterenol potentiates synaptic transmission primarily by enhancing presynaptic calcium influx via P- and/or Q-type calcium channels in the rat amygdala," J. Neurosci. (1996) 16(3):1026-1033.

Huang, C.C. et al., "Selective enhancement of P-type calcium currents by isoproterenol in the rat amygdata," J. Neurosci. (1998) 18(6):2276-2282.

Huang, X. et al., "Metal-dependence of Abeta oligomerization," Soc. for Neurosci. Abstract Viewer and Itinerary Planner (2002), Abstract No. 19.1, 32nd Annual meeting of the Society for Neuroscience, Orlando, FL, Nov. 2-7, 2002.

Huse, W.D. et al., "Generation of a large combinatorial library of the immunoglobulin repertoire in phage lambda," Science (1989) 246:1275-1281.

Huston, J.S. et al., "Protein engineering of antibody binding sites: recovery of specific activity in all anti-digoxin single-chain Fv analogue produced in *Escherichia coli*," PNAS (1988) 85:5879-5883.

Huston, J.S. et al., "Protein engineering of single-chain Fv analogs and fusion proteins," Meth. in Enzymol. (1991) 203:46-88.

Hutchins, W.A. et al., "Human immune response to a peptide mimic of neisseria meningitis serogroup C in hu-PBMC-SCID mice," Hybridoma (1999) 18(2):121-129.

Hyman et al., "Autoantibodies to Amyloid-beta and Alzheimer's disease," Ann. Neurol. (2001) 49:808-810.

Iijima, K. et al., "A beta 42 mutants with different aggregation profiles induce distinct pathologies in *Drosophila*," PLoS One (2008) 3 Article No. E1703.

Ilan, E. et al., "The hepatitis B virus-trimera mouse: a model for human HBV infection and evaluation of anti-HBV therapeutic agents," Hepatology (1999) 29:553-562.

Ingelbrect, I.L.W. et al., "Different 3' end regions strongly influence the level of gene expression in plant cells," The Plant Cell (1989) 1:671-780.

Jang et al., "The structural basis for DNA binding by an anti-DNA autoantibody," Molec. Immunol. (1998) 35:1207-1217.

Janssen, J.C. et al., "Early onset familial Alzheimer's disease: mutation frequency in 31 families," Neurology (2003) 60(2):235-239.

Jefferis, R., "Glycosylation of recombinant antibody therapeutics," Biotechnol. Prog. (2005) 21:11-16.

Jennings-White, C. et al., "Synthesis of ketomethylene analogogs of dipeptides," Tetrahedr. Lett. (1982) 23(25):2533-2534.

Jensen, M.T. et al., "Lifelong immunization with human beta-amyloid (1-42) protects Alzheimer's transgenic mice against cognitive impairment throughout aging," Neurosci. (2005) 130:667-684.

Jiang, S. et al., "Recent progress of synthetic studies to peptide and peptidomimetic cyclization," Curr. Org. Chem. (2008) 12(17):1502-1542.

Joerchel, S. et al., "Oligomeric beta-amyloid(1-42) induces the expression of Alzheimer disease-relevant proteins in cholinergic SN56.B5.G4 cells as revealed by proteomic analysis," Int. J. Developm. Neurosci. (2008) 26(3-4):301-308.

Johansson, A.S. et al., "Attenuated amyloid-beta aggregation and neurotoxicity owing to methionine oxidation," NeuroReport (2007) 18(6):559-563.

Johansson, A.S. et al., "Dramatic changes in fibrillization rate and oligomer/protofibrillar formation of beta-amyloid peptide with oxidized methionine: implications for novel therapeutic approaches in Alzheimer's disease," Soc. for Neurosci. Abstract Viewer and Itinerary Planner (2002), Abstract No. 123.8, 32nd Annual meeting of the Society for Neuroscience, Orlando, FL, Nov. 2-7, 2002.

Johansson, A-S. et al., "Docosahexaenoic acid stabilizes soluble amyloid-beta protofibrils and sustains amyloid-beta-induced neurotoxicity in vitro," FEBS J. (2007) 274(14):990-1000.

Johansson, A-S. et al., "Physiochemical characterization of the Alzheimer's disease-related peptides Abeta 1-42Arctic and Abeta1-42wt," FEBS Journal (2006) 273(12):2618-2630.

Johnsson, B. et al., "Comparison of methods for immobilozation to carboxymethyl dextran sensor surfaces by analysis of the specific activity of monoclonal antibodies," J. Mol. Rec. (1995) 8:125-131.

Johnsson, B. et al., "Immobilizataion of progeins to a carboxymethyldextran-modified gold surface for biospecific interaction analysis in surface plasmon resonance sensors," Anal. Biochem. (1991) 198:268-277.

Joliot, A. et al., "Antennapedia homeobox peptide regulates neural morphogenesis," Proc. Natl. Acad. Sci. USA (1991) 88:1864-1868.

Jones, C.T. et al., "Mutation in codon 713 of the beta-amyloid precursor protein gene presenting with schizophrenia," Nat. Genet. (1992) 1(4):306-309.

Jones, J.D.G. et al., "High level expression of introduced chimaeric genes in regenerated transformed plants," EMBO J. (1985) 4(10):2411-2418.

Jonsson, U. et al., "Introducing a biosensor based technology for real-time biospecific interaction analysis," Ann. Biol. Clin. (1993) 51:19-26.

Jonsson, U. et al., "Real-time biospecific interaction analysis using surface plasmon resonance and a sensor chip technology," BioTechniques (1991) 11(5):620-627.

Jungbauer, L.M. et al., "Preparation of fluorescently-labeled amyloid-beta peptide assemblies: the effect of luorophore conjugation on structure and function," J. Mol. Recogn. (2009) 22(5):403-413.

Kabat, E.A. et al., "Attempts to locate complementarity-determining residues in the variable positions of light and heavy chains," Ann. NY Acad. Sci. (1971) 190:382-391.

Kabat, E.A. et al., Sequences of Proteins of Immunological Interest, 5th Edition, NIH Publ. #91-3242 (1981), Table of Contents.

Kaiser et al., "Peptide and protein synthesis by segment synthesis-condensation," Science (1989) 243:187.

Kakio, A. et al., "Interactions of amyloid beta-protein with various gangliosides in raft-like membranes: importance of GM1

(56) References Cited

OTHER PUBLICATIONS ganglioside-bound form as an endogenous seed fr Alzheimer amyloid," Biochem. (2002) 41:7385-7390.
Kamino, K. et al., "Linkage and mutational analysis of familial Alzheimer disease kindreds for the APP gene region," Am. J. Hum. Genet. (1992) 51(5):998-1014.
Kanemitsu, H. et al., "Human neprilysin is capable of degrading amyloid beta peptide not only in the monomeric form but also the pathologica oligomeric form," Neursci. Lett. (2003) 350:113-116.
Kaufman, R.J. et al., "Amplification and expression of sequences contrasfected with a modular dihydrofolate reductase complementary DNA gene," Mol. Biol. (1982) 159:601-621.
Kawarabayashi, T. et al., "Age-dependent changes in brain, CSF, and plasma amyloid beta protein in the Tg2576 transgenic mouse model of Alzheimer's disease," J. Neurosci. (2001) 21(3):372-381.
Kawarabayashi, T. et al., "Dimeric amyloid beta protein rapidly accumulates in lipid rafts followed by apolipoprotein E and phosphorylated Tau accumulation in the Tg2576 mouse model of Alzheimer's disease," J. Neurosci. (2004) 24(15):3801-3809.
Kayed, R. et al., "Common structure of soluble amyloid oligomers implies common mechanism of pathogenesis," Science (2003) 300(18):486-489.
Kellermann, S-A. et al., "Antibody discovery: the use of transgenic mice to generate human monoclonal antibodies for therapeutics," Curr. Opin. in Biotechnol. (2002) 13:593-597.
Kenneth, R.H. In Monoclonal Antibodies: A New Dimension in Biological Analyses, Plenum Publishing Corp. New York, New York (1980).
Kent, S.B.H., "Chemical synthesis of peptides and proteins," Ann. Rev. Biochem. (1988) 57:957-989.
Keowkase, R. et al., "Mechanism of CNS drugs and their combinations for Alzheimer's disease," Central Nervous System Agents in Medicinal Chemistry (2008) 8(4):241-248.
Kettleborough, C.A. et al., "Isolation of tumor cell-specific single-chain Fv from immunized mice using phage-antibody libraries and the re-construction of whole antibodies from these antibody fragments," Eur. J. Immunol (1994) 24:952-958.
Kim, N.D. et al., "Putative therapeutic agents for the learning and memory deficits of people with Down syndrome," Bioorg. Med. Chem. Left. (2006) 16(14):3772-3776.
Kim, Y.S. et al., "Biological tuning of snythetic tactics in solid-phase synthesis: application to Abeta(1-42)" J. Org. Chem. (2004) 69(22):7776-7778.
Kipriyanov, S.M. et al., "Recombinant single-chain Fv fragments carrying C-terminal cysteine residues: production of bivalent and biotinylated miniantibodies," Mol. Immun. (1994) 31(14):1047-1058.
Kipriyanov, S.M. et al., "Single-chain antibody streptavidin fusions: tetrameric bifunctional scFv-complexes with biotin binding activity and enhanced affinity to antigen," Hum. Antibod. Hybridomas (1995) 6(3):93-101.
Kirkitadze, M.d. et al., "Identification and characterization of key kinetic intermediates in amyloid B-protein fibrillogenesis," J. Mol. Biol. (2001) 312:1103-1119.
Kitamura, Y. et al., "Stress proteins and regulation of microglial amyloid-beta phagocytosis," Folia Pharmacologica Japonica (2004) 124(6):407-413.
Kitchin, K. et al., "Cloning, expression, and purification of an anti-desipramine single chain antibody in NS/0 myeloma cells," J. Pharm. Sci. (1995) 84(10):1184-1189.
Klafki, H-W. et al., "Electrophoretic separation of beta-A4 peptides (1-40) and 1-42)," Anal. Biochem. (1996) 237:24-29.
Klein, W., "A beta toxicity in Alzheimers disease; globular oligomers (ADDLs) as new vaccine and drug targets," Neurochem. Intl. (2002) 41(5):345-352.
Klyubin, I. et al., "Amyloid beta-protein (abeta) bearing the arctic mutation is a more potent inhibitor of LTP than wild type Abeta," Society for Neuroscience Abstract Viewer and Itinerary Planner (2003), 2003 Abstract No. 904.13, 33rd Annual Meeting of the Society of Neuroscience, New Orleans, LA, Nov. 8-12, 2003.

Knappik, A. et al., "Fully synthetic human combinatorial antibody libraries (hUCAL) based on modular consensus frameworks and CDRs randomized with trinucleotides," J. Mol. Biol. (2000) 296:57-86.
Knowles, J.K. et al., "The p75 neurotrophin receptor promotes amyloid-beta(1-42)-induced neuritic dystrophy in vitro and in vivo," J. Neurosci. (2009) 29:10627-10637.
Kobayashi et al., "Tryptophan H33 plays an important role in Pyrimidine (6-4) pyrimidone photo product binding by a high-affinity antibody," Protein Eng. (1999) 12:879-884.
Koh, S-H. et al., "Amyloid-beta-induced neurotoxicity is reduced by inhibition of glycogen synthase kinase-3," Brain Res. (2008) 1188:254-262.
Kohler, "Continuous cultues of fused cells secreting antibody of predefined specificity," Nature (1975) 256:495-497.
Kokubo, H. et al., "Oligomeric proteins ultrastructurally localize to cell processes, especially to axon terminals with higher density, but not to lipid rafts in Tg2576 mouse brain," Brain Res. (2005) 1045(1-2):224-228.
Kontermann, Antibody Engineering, Springer-Verlag, Berlin, Table of Contents (2001).
Kooistra, J. et al., "A new function of human htra2 as an amyloid-beta oligomerization inhibitor," J. Alzheimer's Disease (2009) 17(2):281-294.
Kortekaas, P. et al., "Development of HVA and LVA calcium currents in pyramidal CA1 neurons in the hippocampus of the rat," Dev. Brain Res. (1997) 101(1-2):139-147.
Kranenburg, O. et al., "beta-Amyloid (Abeta) cuases detachment of N1E-115 neuroblastoma cells by acting as a scaffold for cell-associated plasminogen activity," Mol. Cell. Neurosci. (2005) 28(3):496-508.
Kriegler, M., Gene Transfer and Expression—A Laboratory Manual (1990) Table of Contents.
Kumar et al., "Molecular cloning and expression of the Fabs of human autoantibodies in *Escherichia coli*," J. Biol. Chem. (2000) 275:35129-35136.
Kumar, A. et al., "Neuropathology and therapeutic management of Alzheimer's disease—an update," Drugs of the Future (2008) 33(5):433-446.
Kumar-Singh, S. et al., "Dense-core senile plaques in the Flemish variant of Alzheimer's disease are vasocentric," Am. J. Pathol. (2002) 161(2):507-520.
Kundrot, C.E. et al., "Which strategy for a protein crystallization project?" Cell. Mol. Life Sci. (2004) 61:525-536.
Kuo, Y-M. et al., "Water-soluble Abeta (N-40, N-42) oligomers in normal and Alzheimer disease brains," J. Biol. Chem. (1996) 271(8):4077-4081.
Kwon, Y.E. et al., "Synthesis, in vitro assay, and molecular modeling of new piperidine derivatives having dual inhibitory potency against acetylcholinesterase and Abeta SUB 1-42 aggregation for Alzheimer's disease therapeutics," Bioorg. Med. Chem. (2007) 15(20):6596-6607.
Lacor et al., "Synaptic targeting by Alzheimer's-related amyloid beta oligomers," J. Neurosci. (2004) 24:10191-10200.
Laemmli, U.K. et al., "Cleavage of structural proteins during the assembly of the head of bacteriophage T4," Nature (1970) 227:680-685.
Lahiri, D.K. et al., "Lethal weapon: amyloid beta-peptide, role in the oxidative stress and neurodegeneration of Alzheimer's disease," Neurobiol Aging (2004) 25(5):581-587.
Lam, a.R. et al., "Effects of the Arctic (E22-G) mutation on amyloid beta-protein folding: discrete molecular dynamics study," J. Amer. Chem. Soc. (2008) 130(51):17413-22.
Lam, X.M. et al., "Microencapsulation of recombinant humanized monoclonal antibody for local delivery," Proceedings Intl. Symp. Control. Rel. Bioact. Mater. (1997) 24:759-760.
Lambert, M.P. et al., "Diffusible, nonfibrillar ligands derived from A Beta1-42 are potent central nervous system neurotoxins," Proc. Natl. Acad. Sci. (1998) 95:6448-6453.
Lambert, M.P. et al., "Monoclonal antibodies that target pathological assemblies of A beta," J. Neurochem. (2007) 100(1):23-35.

(56) References Cited

OTHER PUBLICATIONS

Lambert, M.P. et al., Vaccination with soluble AB oilgerm generates toxicity-neutralizing antibodies, J. Neurochem. (2001) 79(3):595-605.

Langer & Peppas, Editors, Journal of Macromolec. Sci. (1983) 23:61-127.

Langer, R., New methods of drug delivery, Science (1990) 249:1527-1533.

Lanni, C. et al., "Studies and screening of molecules interacting with beta amyloid and other amyloidogenic proteins," Society for Neuroscience Abstract Viewer and Itinerary Planner (2003) Abstract No. 841.1, 33rd Annual Meeting of the Society of Neuroscience, New Orleans, LA, Nov. 8-12, 2003.

Lashuel, H.A. et al., "Amyloid pores from pathogenic mutations," Nature (2002) 418(6895):291.

Lau, T-L. et al., "Cholesterol and clioquinol modulation of A beta(1-42) interaction with phospholipid bilayers and metals," Biochimica et biophysica acta 92007) 1768(12):3135-44.

Lauren, J. et al., "Cellular prion protein mediates impairment of synaptic plasticity by amyloid-beta oligomers," Nature (2009) 457(7233):1128-1132.

Lazo, N.D. et al., "On the nucleation of amyloid beta-protein monomer folding," Protein Sci. (2005) 14(6):1581-15196.

Leader, K.A. et al., "Antibody responses to the blood group antigen D in SCID mice reconstituted with human blood mononuclear cells," Immunology (1992) 76:229-234.

Lecanu, L. et al., "Caprospinol: moving from a neuroactive steroid to a neurotropic drug," Exp. Opin. Invest. Drugs (2009) 18(3):265-276.

Lee, C-C. et al., "Insulin rescues amyloid beta-induced impairment of hippocampal long-term potentiation," Neurobiol. Aging (2009) 30(3):377-387.

Lee, D.H.S., et al., "Differential physiologic responses of alpha7 nicotinic acetylcholine receptors to beta-amyloid SUB 1-40 and beta-amyloid SUB 10-42," J. Neurobiol. (2003) 55(1):25-30.

Lee, E.B. et al., "Secretion and intracellular generation of truncated Abeta in beta-site amyloid-beta precursor protein-cleaving enzyme expressing human neurons," J. Biol Chem. (2003) 278(7):4458-4466.

Lee, E.B. et al., "Targeting amyloid-beta peptide (Abeta) oligomers by passive immunization with a conformation-selective monoclonal antibody improves learning and memory in Abeta precursor protein (APP) transgenic mice," J. Biol. Chem. (2006) 281(7):4292-4299.

Lee, H-K. et al., "The insulin/Akt signaling pathway is targeted by intracellular beta-amyloid," Mol. Biol. Cell (2009) 20(5):1533-1544.

Lee, T.Y. et al., "Artificial proteases toward catalytic drugs for amyloid diseases," Pure and Applied Chem. (2009) 81:255-262.

Lemere, C.A. et al., "Amyloid-beta immunotherapy for the prevention and treatment of Alzheimer disease: lessons from mice, monkeys, and humans," Rejuvenation Res. (2006) 9(1):77-84.

Lemere, C.A. et al., "Developing novel immunogens for a safe and effective Alzheimer's disease vaccineNeurotherapy: Progress in Restorative Neuroscience and Neurology," Progress in Brain Research (2009) 175:83-93.

Lerner, E.A., "How to make a hybridoma," The Yale Journal of Biology and Medicine (1981) 5(5):387-402.

Leveille, F. et al., "Influence des formes oligomeriques du peptide amyloide beta 1-42 sur la viabilite neuronale," Revue Neurologique (2007) 163(11)-2:4S23.

LeVine, H. et al., "Alzheimer's .beta.-peptide oligomer formation at physiologic concentrations," Anal. Biochem. (2004) 335:81-90.

Levitt, M., "Molecular dynamics of native protein," J. Mol. Biol. (1983) 168:595-620.

Levy et al., "Inhibition of calcification of bioprosthetic heart valves by local controlled-release diphosphonate," Science (1985) 228:190-192.

Lewis, H. et al., "Quantification of Alzheimer pathology in ageing and dementia: age-related accumulation of amyloid-beta(42) peptide in vascular dementia," Neuropath. Appl. Neurobiol. (2006) 32(2):103-118.

Li, H. et al., "SAR and mechanistic studies of tetrapeptide inhibitors of A beta 42-induced neurotoxicity," Biopolymers (2009) 92(4):p. 077.

Liao, Y.J. et al., "Anti-Ca2+ channel antibody attenuates Ca2+ currents and mimics cerebellar ataxia in vio," Proc. Natl. Acad. Sci. USA (2008) 105(7):2705-2710.

Liirs, T. et al., "3D structure of Alzheimer's amyloid-beta (1-42) fibrils," Proc. Natl. Acad. Sci. (2005) 102(48):17342-17347.

Lindberg, C. et al., "beta-amyloid protein structure determines the nature of cytokine release from rat microglia," J. Mol. Neurosci. (2005) 271-21.

Little, M. et al., "Of mice and men: hybridoma and recombinant antibodies," Immun. Today (2000) 21(8):364-370.

Liu, M. et al., "Progress in soluble Abeta oligomers in Alzheimer's disease and drugs targeting Abeta oligomers," Chinese Pharmacological Bulletin (2008) 24(12):1554-1557.

Liu, Q. et al., "A novel nicotinic acetylcholine receptor subtype in basal forebrain cholinergic neurons with high sensitivity to amyloid peptides," J. Neurosci. (2009) 29(4):918-929.

Liu, R. et al., "Residues 17-20 and 35-35 of beta-amyloid play critical roles in aggregation," J. Neurosci Res. (2004) 75(2):162-171.

Liu, R. et al., "Trehalose differentially inhibits aggregation and neurotoxicity of beta-amyloid 40 and 42," Neurobiol. Dis. (2005) 20(1):74-81.

Lonberg, N. et al., "Antigen-specific human antibodies from mice comprising four distinct genetic modifications," Nature (1994) 368:856-859.

Lonberg, N. et al., "Human antibodies from transgenic mice," Intern. Rev. Immunol. (1995) 13:65-92.

Lue, L-F et al., "Soluble amyloid beta peptide concentration as a predictor of synaptic change in Alzheimer's disease," Am. J. Path. (1999) 155(3):853-862.

Lunn, M.P.T. et al., "High-affinity anti-ganglioside IgG antibodies raised in complex ganglioside knockout mice: reexamination of FDIa immunolocalization," J. Neurochem. (2000) 75:404-412.

Ma, Q.L. et al., "p21-activated kinase-aberrant activation and translocation in Alzheimer's disease pathogenesis," J. Biol. Chem. (2008) 283(20):14132-14143.

Macao, B. et al., "Recombinant amyloid beta-peptide production by coexpression with an affibody ligand," BMC Biotechnology (2008) 8:82.

MacCallum, R. M. et al., "Antibody-antigen interactions: contact analysis and binding site topography," J. Mol. Biol. (1996) 262:732-745.

Maccioni, R.B. et al., "What have we learned from the tau hypothesis? Current hypothesis and research milestones in Alzheimer's disease current hypotheses and research milestones in Alzheimer's disease," International Summitt Meeting on Current Hypotheses on Alzheimer Disease, Renaca, Chile, Nov. 22-25, 2007.

MacQuitty, J.M. et al., "GenPharm's knockout mice," Science (1992) 257:1188.

Mader, C. et al., "Interaction of the crystalline bacterial cell surface layer protein SbsB and the secondary cell wall polymer of geobacillus stearothermophilus PV72 assessed by real-time surface plasmon resonance biosensor technology," J. Bacteriol. (2004).

Madrigal, J.L.M. et al., "Neuroprotective actions of noradrenaline: effects of glutathione synthesis and activation of peroxisome proliferator activated receptor delta," J. Neurochem. (2007) 103(5):2092-101.

Maier, M. et al., "Short amyloid-beta immunogens reduce cerebral in an Alzheimer's disease mouse model in the absence of an Amyloid-beta-specific cellular immune response," J. Neurosci. (2006) 26(18):4717-4728.

Maliga, P. et al., Methods in Plant Molecular Biology—A Laboratory Manual, Table of Contents (1995).

Mandal, P.K. et al., "Alzheimer's disease: halothane induces Abeta peptide to oligomeric form—solution NMR studies," Neurochem. Res. (2006) 31(7):883-890.

Manelli, A.M. et al., "A beta 42 neurotoxicity in primary co-cultures: effect of apoE isoform and A beta conformation," Neurobiol. of Aging (2007) 281139-1147.

Manelli, A.M. et al., "ApoE and Abeta1-42 interactions," J. Mol. Neurosci. (2004) 23235-246.

(56) References Cited

OTHER PUBLICATIONS

Manelli, A.M. et al., "Glial activation by oligomeric versus fibrillar Abeta1-42," Soc. for Neurosci. Abstract Viewer and Itinerary Planner (2002), Abstract No. 193.9, 32nd Annual meeting of the Society for Neuroscience, Orlando, FL, Nov. 2-7, 2002.
Marachalonis, J.J. et al., "Evolutionary factors in the emergence of the combinatorial germline antibody repertoire," Adv. Exp. Med. Biol. (2001) 484:13-30.
Maria, T.J. et al., "Upregulation of p21(Cip1) in activated glial cells," Glia (2009) 57524-534.
Mariette, X., "Nucleotidic sequence analysis of the variable domains of four human monoclonal IgM with an antibody activity to myelin-associated glycoprotein," Eur. J. Immunol (1993) 23:846-851.
Marlow, L. et al., "APH1, PEN2 and Nicastrin increase Abeta levels and gamma-secretase activity," Biochem. Biophys. Res. Comm. (2005) 305(3):502-509.
Masliah, E. et al., "Progress in the development of new treatments for combined Alzheimer's and Parkinson's diseases," Drug Development Res. (2002) 56282-292.
Masman, MF. Et al., "In silico study of full-length amyloid beta 1-42 tri- and penta-oligomers in solution," J. Phys. Chem. B. (2009) 113:11710-11719.
Masters, C.L. et al., "Amyloid plaque core portein in Alzheimer disease and Down syndrome," Proc. Natl. Acad. Sci. USA (1985) 82:4245-4249.
Mastrangelo, I.A. et al., "High-resolution atomic force microscopy of soluble A.beta.42 oligomers," J. Mol. Biol. (2006) 358:106-119.
Masuda, Y. et al., "Identification of physiological and toxic conformations in Abeta42 aggregates," Chem Bio Chem. (2009) 10(2):287-295.
Mathura, V.S. et al., "Model of Alzheimer's disease amyloid-beta peptide based on a RNA binding protien," Biochem. Biophys. Res. Comm. (2005) 332(2):585-592.
Mattson et al., "A practical approach to crosslinking," Mol. Biol. Reports (1993) 17:167-183.
Mattson, M.P., "Pathways towards and away from Alzheimer's disease," Nature (2004) 430:631-639.
Mattson, M.P., "Pathways towards and away from Alzheimer's disease," Nature (2004) 431(7004):107.
Maurer, M.H. et al., "The proteome of neural stem cells from adult rat hippocampus," Proteome Sci. (2003) 1(1):4.
May, K., "Buying a new immnoassay system?" BioTechnology—TIBTECH (1993) 11:272-273.
McCafferty, J. et al., "Phage antibodies: filamentous phage displaying antibody variable domains," Nature (1990) 348:552-554.
McLaurin, J. et al., "Inositol steroisomers stabilize an oligomeric aggregate of Alzheimer amyloid beta peptide and inhibit Abeta-induced toxicity," J. Biol. Chem. (2000) 27518495-18502.
McLaurin, J. et al., "Review modulating factors in amyloid-beta fibril formation," J. Structural Biol. (2000) 130(2-3):259-270.
McLean, C.A. et al., "Soluble pool of Abeta amyloid as a determinant of severity of neurodegeneration in Alzheimer's disease," Am. Neurol. Assoc. (1999) 46:860-866.
McPherson, A., "Current approaches to macromolecular crystallization," Eur. J. Biochem. (1990) 189:1-23.
Meijer et al., "Biochemical and cellular effects of roscovitine, a potent and selective inhibitor of the cyclin-dependent kinases cdc2, cdk2 and cdk5," Eur. J. Biochem. (1997) 243(1-2):527-536.
Meli, G. et al., "Direct in vivo intracellular selection of conformation-sensitive antibody domains targeting Alzheimer's amyloid-beta oligomers," J. Mol. Biol. (2009) 287(3):584-606.
Mendez, M.J. et al., "Functional transplant of megabase human immunoglobulin loci recapitulates human antibody response in mice," Nat. Genet. (1997) 15(2):146-156.
Merrifield, B., "Solid phase synthesis," Science (1986) 232:342.
Merrifield, J., "The total synthesis of an enzyme with ribonuclease A activity," J. Am. Chem. Soc. (1969) 91:501-502.
Miller, Y. et al., "Polymorphism of Alzheimer's A beta(17-42) (p3) oligomers: the importance of the turn location and its conformation," Biophys. J. (2009) 971168-1177.

Minkeviciene, R. et al., "Amyloid beta-induced neuronal hyperexcitability triggers progressive epilepsy," J. Neurosci. (2009) 29(11):3453-3462.
Mizushima, S. et al., "pEF-BOX, a powerful mammalian expression vector," Nucl. Acids Res. (1990) 18(17):5322.
Moechars et al., "Early phenotypic changes in transgenic mice that overexpress different mutants of amyloid precursor protein in brain," J. Biol. Chem. (1999) 274(10):6483-6492.
Moir et al., "Autoantibodies to redox-modified oligomeric Abeta are attenuated in the plasma of Alzheimer's disease patients," J. Biol. Chem. (2005) 280:17458-17463.
Monien, B.H. et al., "A novel approach to Alzheimer's disease therapy: inhibition of A beta 42 oligomerization by C-terminal A beta 42 fragments," J. Peptide Sci. (2006) 12147.
Morgan, R.a. et al., "Human gene therapy," Ann. Rev. Biochem. (1993) 62:191-217.
Morgan, T.E. et al., "Abeta-derived diffusible ligands (ADDLs): Clusterin (apo J), congo red binding and toxicity," Society for Neuroscience Abstracts (1999) Abstract No. 252130, 29th Annual Meeting of the Society for Neuroscience, Miami Beach, FL, Oct. 23-28, 1999.
Morley, J.S., "Modulation of the action of regulatory peptides by structural modification," TIPS (1980) 463-468.
Morrison, S.L. et al., "Chimeric human antibody molecules: mouse antigen-binding domains with human constant region domains," Proc. Natl. Acad. Sci. (1984) 81:6851-6855.
Morrison, S.L., "Transfectomas provide novel chimeric antibodies," Science (1986) 229:1202-1207.
Mueller, W. et al., "Apolipoprotein E isoforms increase intracellular Ca2+ differentially through an omega-agatoxin IVA-sensitive Ca2+ channel," Brain Pathology (1998) 8(4):641-653.
Mullan et al., "A locus for familial early-onset Alzheimer's disease on the long arm of chromosome 14, proximal to the alphal-amtichymotrypain gene," Nature Genet. (1992) 2:340-342.
Mullan, M. et al., "A pathogenic mutation for probable Alzheimer's disease in the APP gene at the N-terminus of beta-amyloid," Nat. Genet. (1992) 1(5):345-347.
Muller, W. et al., "Impaired Ca-signling in astrocytes from the Ts16 mouse model of Down syndrome," Neurosci. Lett. (1997) 223(2):81-84.
Mulligan, R.C., "The basic science of gene therapy," Science (1993) 260:926-932.
Mullis, K. et al., "Specific enzymatic amplification of DNA in vitro: the polymerase chain reaction," Cold Spring Harbor Symp. Quant. Biol. (1986) 51:263-273.
Munter, L-M. et al., "GxxxG motifs within the amyloid precursor protein transmembrane sequence are critical for the etiology of Abeta42," EMBO J. (2007) 26(6):1702-1712.
Murphy, W.J. et al., "CD40 stimulation promotes human dsecondary immunoglobulin responses in HuPBL-SCID chimeras," Clin. Immunol (1999) 90(1):22-27.
Murphy, W.J. et al., "The huPBL-SCID mouse as a means to examine human immune functionin vivo," Immunol (1996) 8:233-241.
Murray, M.M. et al, "Amyloid beta protein: a beta 40 inhibits A beta 42 oligomerization," J. Am. Chem. Soc. (2009) 131:6316-6317.
Myagkova, M.A. et al., "Autoantibodies to beta-amyloid and neurotransmitters in patients with Alzheimer's disease and senile dementia of the Alzheimer type," Bulletin of Exp. Biol. Med. (2001) 2:127-129.
Nagele, R.G. et al., "Contribution of glial cells to the development of amyloid plaques in Alzheimer's disease," Neurobiol of Aging (2004) 25(5):663-674.
Naslund, J. et al., "Relative abundance of Alzheimer Abeta amyloid peptide variants in Alzheimer disease and normal aging," Proc. Natl. Acad. Sci. (1994) 91:8378-8382.
Nath et al., "Autoantibodies to amyloid B-peptide (AB) are increased in Alzheimer's disease patients and AB antibodies can enhance AB neurotoxicity," Neuromol. Med. (2003) 3:29-39.
Needleman, S.B. et al., "A general method applicable to the search for similarities in the amino acid sequence of two proteins," J. Mol. Biol. (1970) 48:443-453.

(56) References Cited

OTHER PUBLICATIONS

Nerelius, C. et al., "Alpha-Helix targeting reduces amyloid-beta peptide toxicity," Proc. Natl. Acad. Sci. USA (2009) 106(23):9191-9196.
Neuberger, M.S. et al., "Recombinant antibodies possessing novel effector functions," Nature (1984) 312:604-608.
Nguyen, H. et al., "Production of human monoclonal antibodies in SCID mouse," Microbiol. Immunol. (1997) 41(12):901-907.
Nicholas, M.R. et al., "Different amyloid-ent amyloid-beta aggregation states induced monocyte differentiation or activation," J. Neurochem. (2009) 10867, 40th Annual Meeting of the American Society for Neurochemistry, Charleston, South Carolina, Mar. 7-11, 2009.
Nielsen, H.M. et al., "Preferential uptake of amyloid beta 1-42 oligomers by primary human astrocytes in vitro: influence of SAP and C1q," Mol. Immunol. (2009) 262860, 12th European Meeting on Complement in Human Disease, Hungary, Sep. 5-8, 2009.
Nilges, M. et al., "Determination of three-dimensional structures of proteins from interproton distance data by hybrid distance geometry-dynamical simulated annealing calculations," FEBS Lett. (1989) 229(2):317-324.
Nimmrich, V. et al., "Amyloid beta oligomers (A beta(1-42) globulomer) suppress spontaneous synaptic activity by inhibition of P/Q-type calcium currents," J. Neurosci. (2008) 28(4):788-797.
Nimmrich, V. et al., "Is Alzheimer's disease a result of presynaptic failure?—Synaptic dysfunctions induced by oligomeric p-amyloid," Rev. Neurosci. (2009) 20(1):1-12.
Ning, S. et al., "Intratumoral radioimmunotherapy of a human colon cancer xenograft using a sustained-release gel," Radiotherapy & Oncology (1996) 39:179-189.
Nomura, I. et al., "Mechanism of impairment of long-term potentiation by amyloid beta is independent of NMDA receptors or voltage-dependent calcium channels in hippocampal CA1 pyramidal neurons," Neurosci. Lett. (2005) 391(1-2):1-6.
Oi, V.T. et al., "Chimeric antibodies," BioTechniques (1985) 4(3):214-215.
Okamuro et al., The Biochemistry of Plants—A comprehensive Treatise, V. 15, 1-82 (1989).
Ono, K. et al., "Effects of grape seed-derived polyphenols on amyloid beta-protein self-assembly and cytotoxicity," J. Biol. Chem. (2008) 283(47):32176-32187.
Opazo, C. et al., "Metalloenzyme-like activity of Alzheimer's disease beta-amyloid: Cu-dependent catalytic conversion of dopamine, cholesterol, and biological reducing agents to neurotoxic H SUB 2O SUB 2," J. Biol. Chem. (2002) 277(43):40302-40308.
Orgogozo et al., "Subacute meningoencephalitis in a subset of patients with AD after Abeta42 immunization," Neurology (2003) 61:46-54.
Origlia, N. et al., "Abeta-dependent inhibition of LTP in different intracortical circuits of the visual cortex: the role of RAGE," J. Alzheimer's Disease (2009) 17(1):59-68.
Otto, M. et al., "Neurochemical approaches of cerebrospinal fluid diagnostics in neurogenerative diseases," Methods (2008) 44(4):289-298.
Padlan et al., "Structure of an antibody-antigen complex: crystal structure of the HyHEL-10 Fab-lysozyme complex," Proc. Natl. Acad. Sci USA (1989) 86:5938-5942.
Padlan, E.A. et al., "Identification of specificity-determining residues in antibodies," FASEB (1995) 9:133-139.
Padlan, E.A., "A possible procedure for recucing the immunogenicity of antibody variable domains while preserving their ligand-binding properties," Molec. Immunol (1991) 28(4/5):489-498.
Palmer, J. et al., "Endothelin-converting enzyme-2 is increased in Alzheimer's disease and up-regulated by Abeta," Am. J. Path. (2009) 175(1):262-270.
Pan, X.D. et al., "Tripchlorolide protects neuronal cells from microglia-mediated beta-amyloid neurotoxicity through inhibiting NF-kappa B and JNK signaling," GLIA (2009) 57:1227-1238.
Pan, X-D. et al., "Effect of inflammatory responses in microglia induced by oligomeric beta-amyloid SUB 1-42 on neuronal cells," Acta Anatomica Sinica (2008) 39(6):804-809.
Partis, M.D. et al., "Crosslinking of proteins by omega-maleimido alkanoyl N-hydroxysuccinimide esters," J. Protein Chem. (1983) 2:263-277.
Pastor, M.T. et al., "Amyloid toxicity is independent of polypeptide sequence, length and chirality," J. Mol. Biol. (2008) 375:695-707.
Paul, W.E., editor, Fundamental Immunology, Third Edition, Raven Press, New York (1993) 292-295.
Peacock, M.L. et al., "Novel amyloid precursor protein gene mutation (codon 665Asp) in a patient with late-onset Alzheimer's disease," Ann. Neurol. (1994) 35(4):432-438.
Peacock, M.L. et al., "Novel polymorphism in the A4 region of the amyloid precursor protein gene in a patient without Alzheimer's disease," Neurol. (1993) 43(6):1254-1256.
Pearson, W.R. et al., "Improved tools for biological sequence comparison," PNAS (1988) 85:2444-2448.
Pellicano, M. et al., "The sea urchin embryo: a mdoel to study Alzheimer's beta amyloid induced toxicity," Archives of Biochem. Biophys. (2009) 483:120-126.
Perouansky, M., "Liaisons dangereuses? General anaesthetics and long-term toxicity in the CNS," Eur. J. Anaesthesiol. (2007) 24(2):107-115.
Persic, L. et al., "An integrated vector system for the eukaryotic expression of antibodies or their fragments after selection from phage display libraries," Gene (1997) 187:9-18.
Petrushina, I., "Alzheimer's disease peptide epitope vaccine reduces insoluble but not soluble/oligomeric Abeta species in amyloid precursor protein transgenic mice," J. Neurosci. (2007) 27(46):12721-12731.
Pfeifer, M. et al., "Cerebral hemorrhage after passitve anti-Abeta immunotherapy," Science (2002) 298:1379.
Phu, M-J et al., "Fluorescence resonance energy transfer analysis of apolipoprotein e C-terminal domain and amyloid beta peptide (1-42) interaction," J. Neurosci. Res. (2005) 80(6):877-886.
Pike, C.J. et al., "Structure-activity analyses of B-amyloid peptides: contributions of the B25-35 region to aggregation and neurotoxicity," J. Neurochem. (1995) 64(1):253-265.
Plant, LD. Et al., "The production of amyloid beta peptide is a critical requirement for the viablility of central neurons," J. Neurosci. (2003) 23(13):5531-5535.
Podlisny, M.B. et al., "Aggreagation of secreted amyloid beta-protein into sodium dodecyl sufate-stable oligomers in cell culture," J. Biol. Chem. (1995) 270(16):9564-9570.
Poljak, R.J., "Production and structure of diabodies," Structure (1994) 2:1121-1123.
Portelius, E. et al., "Targeted proteomics in Alzheimer's disease: focus on amyloid-beta," Exp. Rev. Proteomics (2008) 5(2):225-237.
Portolano, S. et al., "High affinity, thyroid-specific human autoantibodies displayed on the surface of filamentous phage use V genes similar to other autoantibodies," J. Immunol (1993) 151(5):L2839-2851.
Presta, LG. et al., "Humanization of an antibody directed against IgE," J. Immunol (1993) 151(5):2623-2632.
Putney, P.W., Calcium Signaling, CRC Press Inc. (2005).
Puzzo, D. et al., "Picomolar amyloid-beta positively modulates synaptic plasticity and memory in hippocampus," J. Neurosci. (2008) 28:14537-14545.
Qian, J. et al., "Presynaptic Ca2+ channels and neurotransmitter release at the terminal of a mouse cortical neuron," J. Neurosci. (2001) 21(11):3721-3728.
Qiu, W. et al., "Convenient, large-scale asymmetric synthesis of eriantiomerically pure trans-cinnamylglycine and -alpha-alamine," Tetrahedron (2000) 56:2577-2582.
Qiu, W.Q. et al., "Degradation of amyloid beta-protein by a metalloprotease secreted by microglia and other neural and non-neural cells," J. Biol. Chem. (1997) 272(10):6641-6646.
Qiu, W.Q. et al., "Insulin-degrading enzyme regulates extracellular levels of amyloid beta-protein by degradation," J. Biol. Chem. (1998) 273(49):32730-32738.

(56) References Cited

OTHER PUBLICATIONS

Qiu, W., "Facile synthesis of hydrocarbon-stapled peptides," Anaspec poster at 20th American Peptide Society Annual Meeting (2008).
Racke, M.M. et al., "Exacerbation of cerebral amyloid angiopathy-associated microhemmorrhage in amyloid precursor protein transgenic mice by immunotherapy is dependent on antibody recognition of deposited forms of amyloid beta," J. Neurosci. (2005) 25(3):629-636.
Rahimi, F. et al., "Photo-induced cross-linking of unmodified proteins (PICUP) applied to amyloidogenic peptides," J. Visualized Exp. (2009) 23.
Rahimi, F. et al., "Structure-function relationships of pre-fibrillar protein assemblies in Alzheimer's disease and related disorders," Curr. Alzheimer Res. (2008) 5(3):319-341.
Rambaldi, D.C. et al., "In vitro amyloid A beta(1-42) peptide aggregation monitoring by asymmetrical flow field-flow fractionation with multi-angle light scattering detection," Anal. Bioanal. Chem. (2009) 394:2145-2149.
Rangachari, V. et al., "Amyloid beta(1-42) rapidly forms protofibrils and oligomers by distinct pathways in low concentrations of sodium dodecylsulfatet," Biochem. (2007) 46:12451-12462.
Rangachari, V. et al., "Rationally designed dehydroalanine (Delta Ala)-containing peptides inhibit amyloid-beta (A beta) peptide aggregation," Biopolymers (2009) 91:456-465.
Rangachari, V. et al., "Secondary structure and interfacial aggregation of Amyloid beta(1-40) on sodium dodecyl sulfate micelles," Biochem. (2006) 45:8639-8648.
Ravault, S. et al., "Fusogenic Alzheimer's peptide fragment Abeta (29-42) in interaction with lipid bilayers: secondary structure, dynamics, and specific interaction with phosphatidyl ethanolamine polar heads as revealed by solid-state NMR," Protein Sci. (2005) 14(5):1181-1189.
Ravetch, J.V. et al., "Structure of the human immunoglobulin µ locus: characterization of embryonic and rearranged J and D genes," Cell (1981) 27:583-591.
Reisner, Y. et al., "The trimera mouse: generating human monoclonal antibodies and an animal model for human diseases," Trends in Biotech. (1998) 16:242-246.
Remington: The Science and Practice of Pharmacy, Mack Publishing (1995) 19th Edition: Table of Contents.
Resende, R. et al., "ER stress is involved in Abeta-induced GSK-3 beta activation and tau phosphorylation," J. Neurosci. Res. (2008) 86(9):2091-2099.
Resende, R. et al., "Neurotoxic effect of oligomeric and fibrillar species of amyloid-beta peptide 1-42: involvement of endoplasmic reticulum calcium release in oligomer-induced cell death," Neurosci. (2008) 155(3):725-737.
Riechman, L. et al., "Reshaping human antibodies for therapy," Nature (1988) 332:323-327.
Robert, R. et al., "Engineered antibody intervention strategies for Alzheimer's disease and related dementias by targeting amyloid and toxic oligomers," Protein Engineering, Design and Selection (2009) 22(3):199-208.
Roberts, R.W. et al., "RNA-peptide fusions for the in vitro selection of peptides and proteins," Proc. Natl. Acad. Sci. USA (1997) 94:12297-12302.
Robinson, J.R. et al., Sustained and Controlled Release Drug Delivery Systems, (1978) Table of Contents.
Roes, J. et al., "Mouse anti-mouse IgD monoclonal antibodies generated in IgD-deficient mice," J. Immunol Meth. (1995) 183:231-237.
Roguska, M.A. et al., "Humanization of murine monclonal antibodies through variable domain resurfacing," Proc. Natl. Acad. Sci. (1994) 91:969-973.
Roher, A.A. et al., "Oligomerization and fibril assembly of the amyloid-beta protein," Biochimica et Biophysica Acta (2000) 1502(1):31-43.
Roher, A.E. et al., "Morphology and toxicity of Abeta-(1-42) dimer derived from neuritic and vascular amyloid deposits of Alzheimer's disease," J. Biol. Chem. (1996) 271(34):20631-20635.
Ronicke, R. et al., Abeta mediated diminution of MTT reduction—an artefact or single cell culture? PLoS One (2008) 3(9) e3236.
Rossi, G. et al., "A family with Alzheimer disease and strokes associated with A713T mutation of the APP gene," Neurology (2004) 63(5):910-912.
Rouillard, J-M et al., "Gene2Oligo: oligonucleotide design for in vitro gene synthesis," Nucl. Acids. Res. (2004) 32:W176-180.
Rudikoff et al., "Single amino acid substitution altering antigen-binding specificity," Proc. Natl. Acad. Sci. USA (1982) 79(6):1979-1983.
Russo, C. et al., "Presenilin-1 mutatiosn in Alzheimer's disease," Nature (2000) 405:531-532.
Sabella, S. et al., "Capillary electrophoresis studies on the aggregation process of beta-amyloid 1-42 and 1-40 peptides," Electrophoresis (2004) 25:3186-3194.
Saido, T.C. et al., "Dominant and differential deposition of distinct beta-amyloid peptide species, AbetaN3 in senile plaques," Neuron (1995) 14:457-486.
Sakmann, B. et al., "Single-channel recording" in Antibodies, 2nd edition, Springer, Table of Contents (1995).
Salomon, A.R. et al., "Nicotine inhibits amyloid formation by the beta-peptide," Biochem. (1996) 35(42):13568-78.
Sambamurti, K. et al., "A partial failure of membrane protein turnover may cause Alzheimer's disease: a new hypothesis," Curr. Alzheimer Res. (2006) 3:81-90.
Sambrook, J. et al., Molecular Cloning—A Laboratory Manual, 2nd Edition (1989) Table of Contents 17.2-17.9.
Samoszuk, M.K. et al., "A peroxide-generating immunoconjugate directed to eosinophil peroxidase is cytotoxic to Hodgkin's disease cells in vitro," Antibody, Immunoconjugates and Radiopharmaceuticals (1989) 2:37-45.
Sandberg, A. et al., "Stabilization of neurotoxic Alzheimer amyloid-beta oligomers by protein engineering," Proc. Natl. Acad. Sci. (2010) 107(35):15595-15600.
Sankaranarayanan, S., "Genetically modified mice models for Alzheimer's disease," Curr. Top. Med. Chem. (2006) 6(6):609-627.
Santos, A.N. et al., "A method for the detection of amyloid-beta SUB 1-40, amyloid-beta SUB 1-42 and amyloid-beta oligomers in blood using magnetic beads in combination with flow cytometry and its application in the diagnostics of Alzheimer's disease," J. Alzheimer's Dis. (2008) 14(2):127-131.
Sanz-Blasco, S. et al., "Mitochondrial Ca2+ overload underlies a beta oligomers neurotoxicity providing an unexpected mechanism of neuroprotection by NSAIDs," PloS One (2008) 3 Article No. e2718.
Sato, J. et al., "Design of peptides that form amyloid-like fibrils capturing amyloid beta 1-42 peptides," Chemistry A Eur. J. (2007) 13:7745-7752.
Sato, N. et al., "Development of new screening system for Alzheimer disease, in vitro Abeta sink assay, to identify the dissocation of soluble Abeta from fibrils," Neurobiol. Dis. (2006) 22(3):487-495.
Saudek, C.D. et al., "A preliminary trail of the programmable implantable medication system for insulin delivery," New Engl. J. Med. (1989) 321(9):574-579.
Sawai, H. et al., "Direct production of the fab fragment derived from the sperm immobilizing antibody using polymerase chain reaction and cDNA expression vectors," Amer. J. Reproduc. Immunol (1995) 34:26-34.
Schafmeister et al., "An all-hydrocarbon cross-linking system for enhancing the helicity and metabolilc stability of peptides," J. Am. Chem. Soc. (2000) 122:5891-5892.
Schenk et al., "Current progress in beta-amyloid immunotherapy," Curr. Opin. Immun. (2004) 16:599-606.
Schenk, D., "Amyloid-beta immunotherapy for Alzheimer's disease: the end of the beginning," Nature (2002) 3:824-828.
Schilling, S. et al., "On the seeding and oligomerization of pGlu-amyloid peptides (in vitro)," Biochem. (2006) 45(41):12393-12399.
Scholtzova, H. et al., "Induction fo toll-like receptor 9 signaling as a method for ameliorating Alzheimer's disease-related pathology," J. Neurosci. (2009) 291846-1854.

(56) References Cited

OTHER PUBLICATIONS

Schott, J.M. et al., "New developments in mild cognitive impairment and Alzheimer's disease," Curr. Opin. Neurol. (2006) 19(6):552-558.
Schuck, P., "Size distribution analysis of macromolecules by sedimentation velocity ultracentrifugation and Lamm equation modeling," Biophys. J. (2000) 78:1606-1619.
Sciaretta et al., "Abeta40-Lactam (D23/K28) models a conformation highly favorable for nucleation of amyloid," Biochem. (2005) 44:6003-6014.
Sefton, M.V., "Implantable pumps," Critical Reviews in Biomedical Engineering (1987) 14(3):201-240.
Selenica, M.L. et al., "Cystatin C reduces the in vitro formation of soluble Abeta1-42 oligomers and protofibrils," Scan. J. Clin. Lab. Invest. (2007) 67(2):179-190.
Selkoe, D.J., "Alzheimer's disease: genes, proteins and therapy," Physiol. Reviews, American Physiological Society (2001) 81(2):741-766.
Selkoe, D.J., Clearing the brain's amyloid cobwebs, Neuron (2001) 32:177-180.
Sergeant, N. et al., "Truncated beta-amyloid peptide species in preclinical Alzheimer's disease as new targets for the vaccination approach," J. Neurochem. (2003) 85:1581-1591.
Shapiro, .S. et al., "DNA target motifs of somatic mutagenesis in antibody genes," Crit. Rev. in Immunol. (2002) 22(3):183-200.
Shields, R.L. et al., "Lack of fucose on human IgG1 N-linked oligosaccharide improves binding to human FcγRIII and antibody-dependent cellular toxiciy," J. Biol. Chem. (2002) 277(30):26733-26740.
Shimizu, E. et al., "IL-4-induced selective clearance of oligomeric beta-amyloid peptide(1-42) by rat primary type 2 microglia," J. Immun. (2008) 181(9):6503-6513.
Shu, L. et al., "Secretion of a single-gene-encoded immunoglobulin from myeloma cells," Proc. Natl. Acad. Sci.(1993) 90:7995-7999.
Shughrue et al., "Anti=ADDL antibodies differentially block oligomer binding to hippocampal neurons," Neurobiol. Aging (2010) 31:189-202.
Sikorski, P. et al., "Structure and texture of fibrous crystals formed by Alzheimer's abeta(11-25) peptide fragment," Structure (London) (2003) 11(8):915-926.
Sims, M.J. et al., "A humanized CD18 antibody can block function without cell destruction," J. Immunol. (1993) 151(4):2296-2308.
Sinz, A., "Chemical cross-linking and mass spectrometry for mapping three-dimensional structures of proteins and protein complexes," J. Mass Spectrom. (2003) 38:1225-1237.
Sjogren, M. et al., "Cholesterol and Alzheimer's disease—is there a relation?," Mechanisms of Aging and Development (2006) 127:138-147.
Sjogren, M. et al., "The link between cholesterol and Alzheimer's disease," World J. Biol. Psych. (2005) 6(2):85-97.
Skerra, A. et al., "Assembly of a functional immunoglobulin F fragment in *Escherichia coli*," Science (1988) 240:1038-1040.
Smith, D.P. et al., "Concentration dependent Cu SUP 2+ induced aggregation and dityrosine formation of the Alzheimer's disease amyloid-betapeptide," Biochem. (2007) 46(10):2881-2891.
Smith, N.W. et al., "Amphotericin B interactions with soluble oligomers of amyloid A beta 1-42 peptide," Bioorg. Med. Chem. (2009) 17:2366-2370.
Smith, T.F. et al., "Comparison of biosequences," Adv. in Applied Math (1981) 2:482-489.
Smith-Gill et al., "Contributions of immunoglobulin heavy and light chains to antibody specificity for lysozyme and two haptens," J. Immunol. (1987) 139:4135-4144.
Smithson, S.L. et al., "Molecular analysis of the heavy chain of antibodies that recognize the capsular polysaccharide of *Neisseria meningitides* in hu-PBMC reconstituted SCID mice and in the immunized human donor," Molec. Immunol (1999) 36:113-124.
Smolen, V.F. et al., editors, Controlled Drug Bioavailability (1984) 1:Table of Contents.
Solorzano-Vargas, R.S. et al., "Epitope mapping and neuroprotective properties of a human single chain FV antibody that binds an internal epitope of amyloid-beta 1-42," Molecular Immunol. (2008) 45(4):881-886.
Sondag, C.M. et al., "Beta amyloid oligomers and fibrils stimulate differential activation of primary microglia," J. Neuroinflamm. (2009) 6 article No. 1.
Song et al., Biochem. Biophys. Res. Comm. (2000) 268:390-394.
Song, Y.K. et al., "Antibody mediated lung targeting of long-circulating emulsions," PDA J. of Pharm. Sci Tech. (1995) 50:372-397.
Soos, K. et al., "An improved synthesis of beta-amyloid peptides for in vitro and in vivo experiments," J. Peptide Science (2004) 10:136.
Sorensen, K. et al., "ApoE counteracts the impairment of mitochondrial activity induced by oligomeric A beta 1-42," Eur. J. Neurol. (2008) 15:45.
Spatola, A.F. et al., "Structure-activity relationships of enkephalins containing serially replaced thiomethylene amide bond surrogates," Life Sci. (1986) 38:1243-1249.
Spatola, A.F. et al., In Chemistry and Biochemistry of Amino Acids, Peptides and Proteins, B. Weinstein editor, Marcel Dekker, New York (1983) vol. VII, 267-357.
Spencer, B. et al., "Novel strategies for Alzheimer's disease treatment," Exp. Opin. Biol. Ther. (2007) 7(12): 1853-1867.
Stan, R.V., "Multiple PV1 dimers reside in the same stomatal or fesestral diaphragm," Am. J. Physiol. Heart Circ. Physiol. (2004) 286(4):H1347-1353.
Standridge, J.B., "Vicious cycles within the neuropathophysiologic mechanisms of Alzheimer's disease," Curr. Alzheimer Res. (2006) 3(2):95-107.
Staros et al., "Enhancement by N-hydroxysulfosuccinimide of water-soluble carbodiimide-mediated coupling reactions," Anal. Biochem. (1986) 156(1):220-222.
Stewart, J.M. et al., Solid-Phase Peptide Synthesis, 2nd Edition, Pierce Chemical Company (1984) Table of Contents.
Stine, W. et al., "In vitro characterization of conditions for amyloid-beta peptide oligomerization and fibrillogenesis," J. Biol. Chem. (2003) 278(13):11612-11622.
Stine, W.B. et al., "Antibodies specific for toxic Abeta oligomers," Abst. Viewer/Itinerary Planner, Soc. of Neurosci. (2003) 1.
Studnicka, G.M. et al., "Human-engineered monoclonal antibodies retain full specific binding activity by preserving non-CDR complementarity-modulating residues," Protein Eng. (1994) 7(6):805-814.
Suram, A. et al., "A new evidence for DNA nicking property of amyloid beta-peptide (1-42): relevance of Alzheimer's disease," Archives of Biochem. Biophys. (2007) 463(2):245-252.
Tabaton, M. et al., "Role of water-soluble amyloid-beta in the pathogenesis of Alzheimer's disease: role of amyloid-beta in Alzheimer's disease," Int. J. Exp. Path. (2005) 3(85):139-145.
Tabaton, M., "Coffee 'breaks' Alzheimer's disease," J. Alzheimer's Disease (2009) 17/3:699-700.
Taguchi, J. et al., "Different expresison of calreticulin and immunoglobulin binding protein in Alzheimer's disease brain," Acta Neuropathologica (2000) 100(2):153-160.
Takano, K., "Amyloid beta conformation in aqueous environment," Curr. Alzheimer Res. (2008) 5(6):540-547.
Takata, K. et al., "High mobility group box protein-1 enhances amyloid-beta neurotoxicity," J. Pharm. Sci. (2006) 100154P, 79th Annual Meeting of the Japanese Pharmacological Society, Yokohama, Japan, Mar. 8-10, 2006.
Takata, K. et al., "Possible involvement of small oligomers of amyloid-beta peptides in 15-deoxyDELTA12, 14 prostaglandin J2-sensitive microglial activation," J. Pharm. Sci. (2003) 91:330-333.
Takeda, S.I. et al., "Construction of chimaeric processed immunoglobulin genes containing mouse variable and human constant region sequences," Nature (1985) 314:452-454.
Tamagno, E. et al., "The various aggregation states of beta-amyloid 1-42 mediate different effects on oxidative stress, neurodegeneration, and BACE-1 expression," Free Radic. Biol. Med. (2006) 41(2):202-212.
Tamura, M. et al., "Structural correleates of an anticarcinoma antibody: identification of specificity-determining residues (SDRs) and

(56) References Cited

OTHER PUBLICATIONS development of a minimally immunogenic antibody variant by retention of SDRs only," J. Immunol. (2000) 164(3):1432-1441.

Taniguchi, A. et al., "'Click peptide': pH-triggered in situ production and aggregation of monomer Abeta1-42," Chembiochem. (2009) 10(4);710-715.

Taniuchi, M. et al., "Induction of nerve growth factor receptor in Schwann cells after axotomy," Proc. Natl. Acad. Sci. (1986) 83:4094-4098.

Tanzi, R., "Alzheimer research forum discussion: gain or loss of function—time to shake up assumptions on gamma-secretase in Alzheimer disease? Commentary," J. Alzheimer's Dis. Sep. 2007) 11(3):409.

Tanzi, R.E., "Novel therapeutics for Alzheimer's disease," Neurotherapeutics (2008) 5(3):377-380.

Tarozzi, A. et al., "Cyanidin 3-O-glucopyranoside protects and rescues SH-Sy5Y cells against amyloid-beta peptide-induced toxicity," Neuroreport (2008) 19(15):1483-1486.

Taylor, L.D. et al., "A transgenic mouse that expresses a diversity of human sequence heavy and light chain immunoglobulins," Nucl. Acids. Rse. (1992) 20(23):6287-6295.

Teplow, D.B. et al., "Effects of structural modifications in a beta on its oligomer size distribution," Soc. for Neurosci. Abstract Viewer and Itinerary Planner (2002), Abstract No. 19.6, 32nd Annual meeting of the Society for Neuroscience, Orlando, FL, Nov. 2-7, 2002.

Terry, R.D. et al., "Physical basis of cognitive alterations in Alzheimer's disease: synapse loss is the major correlate of cognitive impairment," Am. Neurol. Assoc. (1991) 572-580.

Terryberry, J.W. et al., "Autoantibodies in neurodegenerative diseases: antigen-specific frequencies and intrathecal analysis," Neurobiology of Aging (1998) 19(3):205-216.

Tew, D.J. et al., "Stabilization of neurotoxic soluble beta-sheet-rich conformations of the Alzheimer's disease amyloid-beta peptide," Biophys. J. (2008) 974752-2766.

Thal, D.R. et al., "Fleecy amyloid deposits in the internal layers of the human entorhinal cortex are comprised of N-terminal truncated fragments of A13," J. Neuropath. Exp. Neurol. (1999) 58:210-216.

Tijssen, P., editor, "Hybridization with nucleic acid probes—Part II: Probe labeling and hybridzation techniques," Laboratory Techniques in Biochemistry and Molecular Biology, (1993) 24:iii-vi, 269-613, table of contents.

Tolstoshev, P., "Gene therapy, concentps, current trials and future directions," Ann. Rev. Pharmacol. Toxicol. (1993) 32:573-596.

Tomaselli, S. et al., "The alpha-to-beta conformational transition of Alzheimer's Abeta-(1-42) peptide in aqueous media is reversible: a step by step conformational analysis suggests the location of beta conformation seeding," ChemBioChem. (2006) 7(2):257-267.

Tomidokoro, Y. et al., "Familial Danish dementia: co-existence of Danish and Alzheimer amyloid subunits (Adan and Abeta) in the absence of compact plaques," J. Biol. Chem. (2005) 280(44):36883-36894.

Tomidokoro, Y. et al., "Familial Danish dementia: the relationship of two different amyloids (Adan/Abeta) deposited in the brain," Society for Neuroscience Abstract Viewer and Itinerary Planner (2002) 2002Abstract No. 328.9, 32nd Annual Meeting of the Society of Neuroscience, Orlando, FL, Nov. 2-7, 2002.

Tomiyama, T. et al., "A new amyloid beta variant favoring oligomerization in Alzheimer's-type dementia," Ann. Neurol. (2008) 63(3):377-387.

Tsubuki, S. et al., "Dutch, Flemish, Italian and Arctic mutations of APP and resistance of Abeta to physiologically relevant proteolytic degradation," Lancet (2003) 361(9373):1957-1958.

Turner, R. et al., "The potential exploitation of plant viral translational enhancers in biotechnology for increased gene expression," Mol. Biotech. (1995) 3:225-236.

Tusell, J.M. et al., "Upregulation of p21Cip1 in activated glial cells," Glia (2009) 57(5):524-534.

Ueki et al., "Solid phase synthesis and biological activities of (Arg8)-vasopressin methylenedithioether," Bioorg. Med. Chem. Lett. (1999) 9:1767-1772.

Umana, P. et al., "Engineered glycoforms of an antieuro-blastoma IgG1 with optimized antibody-dependent cellular cytotoxic activity," Nature Biotech. (1999) 17:176-180.

Urbanc, B. et al., "Computer simulations of Alzheimer's amyloid beta-protein folding and assembly," Curr. Alzheimer Res. (2006) 3(5):493-504.

Urbanc, B. et al., "In silico study of amyloid beta-protein folding and oligomerization," Proc. Natl. Acad. Sci. USA (2004) 101:17345-17350.

Urbanc, B. et al., "Molecular dynamics simulation of amyloid beta dimer formation," Biophys. J. (2004) 87(4):2310-2321.

Urlaub et al., "Isolation of Chinese hamster cell mutants deficient in dihydrofolate reductase activity," Proc. Natl. Acad. Sci. (1980) 77:4216-4220.

Uto, L. et al., "Determination of urinary Tamm-Horsfall protein by ELISA using a maleimide method for enzyme-antibody conjugation," J. Immunol. Methods (1991) 138:87-94.

Vajdos et al., J. Mol. Biol. (2002) 320(2):415-428.

Valincius, G. et al., "Soluble amyloid beta-oligomers affect dielectric membrane properties by bilayer insertion and domain formation: implications for cell toxicity," Biophys. J. (2008) 95(10):4845-4851.

Van Broeck, B. et al., "Current insights into molecular mechanisms of Alzheimer disease and their implications for therapeutic approaches," Neurdegenerative Dis. (2007) 4(5):349-365.

Van Broeckhoven et al., "Amyloid beta protein precursor gene and hereditary cerebral hemorrhage with amyloidosis (Dutch)" Science (1990) 248(4959):1120-1122.

Vattemi, G. et al., "Amyloid-beta42 is preferentially accumulated in muscle fibers of patients with sporadic inclusion-body myositis," Acta Neuropathol. (2009) 117(5):569-574.

Veber, D.F. et al., "The design of metabolically-stable peptide analogs," TINS (1985) 392-396.

Verhoeven, M. et al., "Engineering of antibodies," Bioessays (1988) 8(2):74-78.

Vestergaard, M. et al., "Detection of Alzheimer's amyloid beta aggregation by capturing molecular trails of individual assemblies," Biochem. Biophys. Res. Comm. (2008) 377(2):725-728.

Vickers, "A vaccine against Alzheimer's disease," Drugs Aging (2002) 19:487-494.

Viola, K.L. et al., "Addls bind selectively to nerve cell surfaces in receptor-like puncta," Soc. for Neurosci. Abstract Viewer and Itinerary Planner (2002), Abstract No. 91.9, 32nd Annual meeting of the Society for Neuroscience, Orlando, FL, Nov. 2-7, 2002.

Viola, K.L. et al., "Immunolocalization of oligomeric Abeta42 bindnig to primary mouse hippocampal cells and B103 rat neuroblastoma cells," Society for Neuroscience Abstracts (1999), 29th Annual Meeting of the Society for Neuroscience, Miami Beach, FL, Oct. 23-28, 1999.

Wahlstrom, A. et al., "Secondary structure conversions of Alzheimer's A beta(1-40) peptide induced by membrane-mmimicking detergents," FEBS J. (2008) 275:5117:5128.

Wakutani, Y. et al., "Novel amyloid precursor protein gene missense mutation (D678N) in probable familial Alzheimer's disease," J. Neurol. Neurosurg. Psychiatry (2004) 75(7):1039-1042.

Walensky et al., "Activation of apoptosis in vivo by a hydrocarbon-stapled BH3 helix," Science (2004) 305:1466-1470.

Wallick, S.C. et al., "Glycosylation of a V(H) residue of a monoclonal antibody against alpha-1-6) dextran increases its affinity for antigen," J. Exp. Med. (1988) 168:1099-1109.

Wang, H. et al, "Soluble oligomers of Abeta(1-42) impair LTP in rat hippocampal dentate gyms," Society for Neuroscience Abstracts (2000) Abstract No. 663.18, 30th Annual Meeting of the Society of Neuroscience, New Orleans, LA, Nov. 4-9, 2000.

Wang, H. et al., "Direct and selective elimination of specific prions and amyloids by 4,5-dianilinophthalimide and analogs," Proc. Natl. Acad. Sci. USA (2008) 105:7159-7164.

Wang, H.W. et al., "Differential effect of Abeta1-42 conformation and apoE isoform on LTP," Society for Neurosci. Abstracts (2001) 752.18, 31st Annual meeting of the Society for Neurosci., San Diego, CA, Nov. 10-15, 2001.

Wang, H-W. et al., "Soluble oligomers of beta amyloid (1-42) inhibito long-term potentiation but not long-term depression in rat dentate gyrus," Brain Res. (2002) 924(2):133-140.

(56) References Cited

OTHER PUBLICATIONS

Wang, J. et al., "Development and characterization of a TAPIR-like mouse monoclonal antibody to amyloid-beta," J. Alzheimer's Disease (2008) 14(2):161-173.
Wang, R. et la., "The profile of soluble amyloid beta protein in cultured cell medicine . . . " J. Biol. Chem. (1996) 271(50):31894-31902.
Wang, Z. et al., "Per-6-substituted-per-6-deoxy beta-cyclodextrins inhibit the formation of beta-amyloid peptide derived soluble oligomers," J. Med. Chem. (2004) 47:3329-3333.
Ward, E.S. et al., "Binding activities of a repetoire of single immunoglobulin varialbe domains secreted from *Escherichia coli*," Nature (1989) 341:544-546.
Weggen, S. et al., "Evidence that nonsteroidal anti-inflammatory drugs decrease amyloid beta-42 production by direct moculation of y-secretase activity," J. Biol. Chem. (2003) 276(34):31831-31837.
Weksler et al., "Patients with Alzheimer disease have lower levels of serum anti-amyloid peptide antibodies than healthy elderly individuals," Gerontology (2002) 37:943-948.
Wels, B. et al., "Synthesis of a novel potent cyclic peptide MC4-ligand by ring-closing metathesis," Bioorg. Med. Chem. (2005) 13:4221-4227.
Wermuth, C.G. et al., "Glossary of terms used in medicinal chemistry," Pure and Applied Chem. (1998) 70:1129-1143.
Westlind-Danielsson, A. et la., "Spontaneous in vitro formation of supramolecular beta-amyloid structures, 'betaamy balls' by beta-amyloid 1-40 peptide," Biochem. (2001) 40(49):14736-43.
White, J.A. et al., "Differential effects of oligomeric and fibrillar amyloid-beta 1-42 on astrocyte-mediated inflammation," Neurbiol. of Disease 92005) 18(3):459-465.
Wilcock et al., "Passive immunotherapy against Abeta in aged APP-transgenic mice reverses cognitive deficits and depletes parenchymal amyloid deposits in spite of increased vascular amyloid and microhemorrhage," J. Neuroinflammation (2004) 1(24):1-11.
Wilcock, D.M. et al., "Intracranially administered anti-A-beta antibodies reduce beta-amyloid depsoition by mechanisms both independent of and associated with microglial activation," J. Neurosci. (2003) 23(9):3745-3751.
Williamson, M.P. et al., "Binding of amyloid beta-peptide to ganglioside micelles is dependent on histidine-13," Biochem. J. (2006) 397:483-490.
Wilson, D.M. et al., "Free fatty acids stimulate the polymerization of tau and amyloid beta peptides in vitro evidence for a common effector in pathogenesis in Alzheimer's disease," Am. J. Path. (1997) 150(6):2181-2195.
Wiltfang, J. et al., "Highly conserved and disease-specific patterns of carboxyterminally truncated A-beta peptides 1-37/38/39 in addition to 1-40/42 in Alzheimer's disease and in patients with chronic neuroinflammation," J. Neurochem. (2002) 81:481-495.
Windisch, M. et al., "The role of alpha-synuclein in neurodegenerative diseases: a potential target for new treatment strategies," Neuro-Degenerative Diseases (2008) 5(3-4):218-221.
Winnacker, E-L., From Genes to Clones: Introduction to Gene Technology (1987) Table of Contents.
Wong, P.T. et al., "Amyloid-beta membrane binding and permeabilization are distinct processes influenced separately by membrane charge and fluidity," J. Mol. Biol. (2009) 286(1):81-96.
Woodhouse, A. et al., "Vaccination strategies for Alzheimer's disease: a new hope?" Drugs Aging (2007) 24(2): 107-119.
Wright, A. et al., "Antibody variable region glycosylation: position effects on antigen binding and carbohydrate structure," EMBO J. (1991) 10(10):2717-2723.
Wu et al., "Humanization of a murine monoclonal antibody by simultaneous optimization of framework and CDR residues," J. Mol. Biol. (1999) 294:151-162.
Wu, C. et al., "The structure of Abeta42 C-terminal fragments probed by a combined experimental and theoretical study," J. Mol. Biol. (2009) 287(2):492-501.
Wu, G.Y. et al., "Delivery systems for gene therapy," Biotherapy (1991) 3:87-95.
Wu, G.Y. et al., "Receptor-mediated in vitro ene transformation by a soluble DNA carrier system," J. Biol. Chem. (1987) 262:4429-4432.
Wurth, C. et al., "Mutations that reduce aggregation of the Alzheimer's Abeta42 peptide: an unbiased search for the sequence determinants of Abeta amyloidogenesis," J. Mol. Biol. (2002) 319(5):1279-1290.
Xia, W. et al., "A specific enzyme-linked immunosorbent assay for measuring beta-amyloid protein oligomers in human plasma and brain tissue of patients with Alzheimer disease," Archives of Neurology (2009) 66190-199.
Xia, W. et al., "Enhanced production and oligomerization fo the 42-residue amyloid beta-protein by Chinese hamster ovary cells stably expressing mutant presenilins," J. Biol. Chem. (1997) 272(12):7977-7982.
Xu, X. et al., "gamma-secretase catalyzes sequential cleavages of the A beta PP transmembrane domain," J. Alzheimer's Disease (2009) 16:211-224.
Yamamoto, N. et al., "Environment- and mutation-dependent aggregation behavior of Alzheimer amyloid beta-protein," J. Neurochem. (2004) 90:62-69.
Yamin, G. et al., "Amyloid beta-protein assembly as a therapeutic target of Alzheimer's disease," Curr. Pharm. Design (2008) 14:3231-3246.
Yamin, G. et al., "NMDA receptor-dependent signaling pathways that underlie amyloid beta-protein disruption of LTP in the hippocampus," J. Neuroscience Res. (2009) 87(8):1729-1736.
Yan, Y. et al., "Protection mechanisms against Abeta42 aggregation," Curr. Alzheimer Res. (2008) 5(6):548-554.
Yan, Z. et al., "Roscovitine: a novel regulator of P/Q-type calcium channels and transmitter release in central neurons," J. Physiol. (2002) 540(3):761-770.
Yang, M. et al., "Amyloid beta-protein monomer folding: free-energy surfaces reveal alloform-specific differences," J. Mol. Biol. (2008) 384(2):450-464.
Yang, X.D. et al., "Fully human anti-interleukin-8 monoclonal antibodies: potential therapeutics for the treatment of inflammatory disease status," J. Leukocyte Biol. (1999) 66:401-410.
Yeh, M.Y. et al., "A cell-surface antigen which is present in the ganglioside fraction and shared by human melanomas," Int. J. Cancer (1982) 29:269-275.
Yeh, M.Y. et al., "Cell surface antigens of human melanoma identified by monoclonal antibody," Proc. Natl. Acad. Sci. USA (1979) 76(6):2927-2931.
Yoshinari, K. et al., "Differential effects of immunosuppressants and antibiotics on human monoclonal antibody production is SCID mouse ascites by five heterohybridomas," Hybridoma (1998) 17(1):41-45.
Yoshitake et al., "Mild and efficient conjugation of rabbit Fab and horseradish peroxidase using a maleimide compound and its use for enzyme immunoassay," J. Biochem. (1982) 92:1413-1424.
Young, K.F. et al., "Oligomeric amyloid-beta 1-42 activates extracellular signal regulated kinases ERK1 and ERK2 of the mitogen activated protein kinase pathway in SH-SY5YCells," Neurobiol of Aging (2004) 25:S150.
Youssef, I. et al., "N-truncated amyloid-beta oligomers induce learning impairment and neuronal apoptosis," Neurobiol of Aging (2008) 29:1319-1333.
Yu, L. et al., "Structural characterization of a soluble amyloid beta-peptide oligomer," Biochem. (2009) 48:1870-1877.
Yun, S. et al., "Role of electrostatic interactions in amyloid beta-protein (Abeta) oligomer formation: a discrete molecular dynamics study," Biophys. J. (2007) 92(11):4064-4077.
Yun, S.H. et al., "Amyloid-beta 1-42 reduces neuronal excitability I nmouse dentate gyrus," Neurosci. Lett. Sep. 2006) 403:162-165.
Zameer, A. et al., "Anti-oligomeric abeta single-chain variable domain antibody blocks abeta-induced toxicity against human neuroblastoma cells," J. Mol. Biol. (2008) 384(4):917-928.
Zarandi, M. et al., "Synthesis of Abeta[1-42] and its derivatives with improved efficiency," J. Peptide Sci. (2007) 13(2):94-99.
Zhao, J-H. et al., "Molecular dynamics simulations to investigate the aggregation behaviors of the Abeta(17-42) oligomers," J. Biomol. Struct. Dyn. (2009) 26(4):481-490.

(56) References Cited

OTHER PUBLICATIONS

Zhao, W. et al., "Identification of antihypertensive drugs which inhibit amyloid-beta protein oligomerization," J. Alzheimer's Dis. (2009) 16(1):49-57.
Zheng, J. et al., "Annular structures as intermediates in fibril formation of Alzheimer Abeta17-42," J. Phys. Chem. (2008) 112(22):6856-6865.
Zhu, D. et la., "Phospholipases A2 mediate amyloid-beta peptide-induced mitochondrial dysfunction," J. Neurosci. (2006) 26(43):11111-11119.
Zlokovic, B.V., "Clearing amyloid through the blood-brain barrier," J. neurochem. (2004) 89(40:807-811.
Zou, K et al., "A novel function of monomeric amyloid beta-protein serving as an antioxidant molecule against metal-induced oxidative damage," J. Neurosci. (2002) 22:4833-4841.
Zou, K. et al., "Amyloid beta-protein (Abeta)1-40 protects neurons from damage induced by Abeta1-42 in culture and in rat brain," J. Neurochem. (2003) 87(3):609-619.
European Patent Office Search Report for Application No. 09180982 dated May 31, 2010 (4 pages).
Notice of Opposition for European Application No. 06707413/Patent No. 1861422 dated Nov. 24, 2010.
Supplemental European Patent Office Search Report for Application No. 07864914 dated Apr. 28, 2010 (5 pages).
Supplemental European Search Report from European Patent Publication No. 2303920 dated Sep. 26, 2011.
European Patent Office Action for Application No. 087160818 dated Dec. 22, 2011 (6 pages).
European Patent Office Action for Application No. 101783942 dated Mar. 2, 2012 (4 pages).
European Patent Office Action for Application No. 101783942 dated Aug. 22, 2012 (4 pages).
International Preliminary Report on Patentability and Written Opinion for Application No. PCT/EP2004/000927 dated Aug. 5, 2005 (11 pages).
International Preliminary Report on Patentability and Written Opinion for Application No. PCT/EP2006/011530 dated Jun. 3, 2008 (11 pages).
International Preliminary Report on Patentability and Written Opinion for Application No. PCT/EP2008/001548 dated Sep. 1, 2008 (11 pages).
International Preliminary Report on Patentability and Written Opinion for Application No. PCT/IB2009/006636 dated Jan. 25, 2011 (7 pages).
International Preliminary Report on Patentability and Written Opinion for Application No. PCT/US2006/046043 dated Jun. 30, 2008 (32 pages).
International Preliminary Report on Patentability and Written Opinion for Application No. PCT/US2006/046148 dated Jun. 3, 2008 (8 pages).
International Preliminary Report on Patentability and Written Opinion for Application No. PCT/US2007/085932 dated Jun. 3, 2009 (5 pages).
International Preliminary Report on Patentability and Written Opinion for Application No. PCT/US2008/065199 dated Dec. 1, 2009 (10 pages).
International Preliminary Report on Patentability and Written Opinion for Application No. PCT/US2008/065205 dated Dec. 1, 2009 (6 pages).
International Preliminary Report on Patentability and Written Opinion for Application No. PCT/US2009/051721 dated Jan. 25, 2011 (7 pages).
International Search Report for Application No. PCT/EP2004/000927 dated Jun. 14, 2004 (4 pages).
International Search Report for Application No. PCT/EP2008/001548 dated Jul. 4, 2008 (3 pages).
International Search Report for Application No. PCT/EP2008/001549 mailed on Dec. 23, 2008 (6 pages).
International Search Report for Application No. PCT/IB2009/006636 dated Jan. 22, 2010 (6 pages).
International Search Report for Application No. PCT/PCT/EP2006/011530 dated Jun. 6, 2007 (7 pages).
International Search Report for Application No. PCT/US2006/046043 dated Jun. 21, 2008 (16 pages).
International Search Report for Application No. PCT/US2006/046148 dated Jun. 19, 2007 (5 pages).
International Search Report for Application No. PCT/US2007/085932 dated Spetember 22, 2008 (3 pages).
International Search Report for Application No. PCT/US2008/065199 dated Sep. 26, 2008 (4 pages).
International Search Report for Application No. PCT/US2008/065205 dated Oct. 31, 2008 (3 pages).
International Search Report for Application No. PCT/US2009/051721 mailed on Mar. 16, 2010 (6 pages).
International Search Report for Application No. PCT/US2011/047622 dated Jan. 2, 2012 (6 pages).
Written Opinion for Application No. PCT/US2011/047622 dated Jan. 2, 2012 (8 pages).
United States Patent Office Action for U.S. Appl. No. 11/574,844 dated Feb. 10, 2011 (11 pages).
United States Patent Office Action for U.S. Appl. No. 11/574,847 dated Jul. 14, 2011 (22 pages).
United States Patent Office Action for U.S. Appl. No. 11/574,876 dated Jan. 23, 2012 (17 pages).
United States Patent Office Action for U.S. Appl. No. 11/574,876 dated Nov. 15, 2012 (9 pages).
United States Patent Office Action for U.S. Appl. No. 11/885,362 dated Jul. 22, 2010 (10 pages).
United States Patent Office Action for U.S. Appl. No. 11/885,362 dated Mar. 29, 2011 (8 pages).
United States Patent Office Action for U.S. Appl. No. 11/945,124 dated Mar. 3, 2010 (15 pages).
United States Patent Office Action for U.S. Appl. No. 11/945,124 dated Oct. 14, 2010 (8 pages).
United States Patent Office Action for U.S. Appl. No. 12/509,315 dated Jun. 6, 2012 (10 pages).
United States Patent Office Action for U.S. Appl. No. 12/509,325 dated Jun. 6, 2012 (14 pages).
United States Patent Office Action for U.S. Appl. No. 13/102,713 dated Apr. 19, 2012 (20 pages).
United States Patent Office Action for U.S. Appl. No. 13/102,713 dated Oct. 1, 2012 (14 pages).
United States Patent Office Action for U.S. Appl. No. 13/188,034 dated Jan. 3, 2012 (35 pages).
United States Patent Office Action for U.S. Appl. No. 13/188,034 dated Sep. 11, 2012 (18 pages).
United States Patent Office Action for U.S. Appl. No. 13/195,533 dated Nov. 13, 2012 (23 pages).
United States Patent Office Notice of Allowance for U.S. Appl. No. 11/574,844 dated Aug. 11, 2011 (14 pages).
United States Patent Office Notice of Allowance for U.S. Appl. No. 11/574,844 dated May 9, 2012 (8 pages).
United States Patent Office Notice of Allowance for U.S. Appl. No. 11/574,847 dated Feb. 10, 2012 (12 pages).
United States Patent Office Notice of Allowance for U.S. Appl. No. 11/574,847 dated Oct. 4, 2012 (8 pages).
United States Patent Office Notice of Allowance for U.S. Appl. No. 11/945,124 dated Apr. 4, 2011 (8 pages).
United States Patent Office Notice of Allowance for U.S. Appl. No. 11/945,124 dated Mar. 5, 2012 (7 pages).
United States Patent Office Notice of Allowance for U.S. Appl. No. 11/945,124 dated Oct. 9, 2012 (7 pages).
United States Patent Office Action for U.S. Appl. No. 13/085,891 dated Apr. 18, 2013 (16 pages).
Acha-Orbea et al., "Anti-T-cell receptor V beta antibodies in autoimmunity," Immunol. Ser. (1993) 59:193-202.
Anderson et al., "Characterization of beta amyloid assemblies in drusen: the deposits associated with aging and age-related macular degeneration," Experimental Eye Research (2004) 78:243-256.
Bard et al., "Epitope and isotype specificities of antibodies to beta-amyloid peptide for protection against Alzheimer's disease-like neuropathology," Proc. Natl. Acad. Sci. (2003) 100(4):2023-2028.

(56) References Cited

OTHER PUBLICATIONS

Bard et al., "Peripherally administered antibodies against amyloid bipeptide enter the central nervous system and reduce pathology in a mouse model of Alzheimer disease," Nature Med. (2000) 6:916-919.
Brown, M. et al., "Tolerance to single, but not multiple, amino acid replacements in antibody V-H CDR2: a means of minimizing B cell wastage from somatic hypermutation?" J. Immunol (1996) 156(9):3285-3291.
Campbell et al., "General properties and applications of monoclonal antibodies," Elsevier Science Publishers B.V. (1984) pp. 1-32.
Celli et al., "Origin and pathogenesis of antiphospholipid antibodies," Braz. J. Med. Biol. Res. (1998) 31(6):723-732.
Database EMBL, "Mouse immunoglobulin rearranged kappa-chain V-region V105 gene from, C.AL20-TEPC-105 myeloma, exons 1 and 2," Jul. 16, 1988, Database Accession No. M12183.
Database EMBL, "*Mus musculus* F5.20G3 low-affinity anti-phosphorylcholine IgG antibody mRNA, partial cds," Feb. 8, 1999, Database Accession No. AF044238.
Database Geneseq, "Anti-human Fas monoclonal antibody CH11 light chain cDNA," retrieved from EBI Accession No. GSN:AAV66736, Jan. 18, 1999, Database Accession No. AAV66736.
Database Geneseq, "Mouse DNA encoding antibody 3D8 heavy chain variable region," Apr. 22, 2003, Database Accession No. ABX16569.
Database Geneseq, "Mouse monoclonal antibody 4785 heavy chain SEQ ID 38", retrieved from EBI Accession No. GSP:ADX39137,(2005) Database Accession No. ADX39137.
Database Geneseq., Humanized monoclonal antibody H74785-2 heavy chain, retrieved from EBI accession No. GSP:ADX39139, 2005, Database Accession No. ADX39139.
Database Geneseq., "Humanized monoclonal antibody Hu4785-2 partial protein," retrieved from EBI Accession No. GSP:ADX39104 (2005) Database Accession No. ADX39104.
Database Geneseq., "Humanized monoclonal antibody Hu4785-2 VH region," retrieved from EBI accession No. GSP:ADX39143 (2005), Database Accession No. ADX39143.
Database Geneseq., "Mouse monoclonal antibody 4785 heavy chain SEQ ID 1," retrieved from EBI Accession No. GSP:ADX39100 (2005) Database Accession No. ADX39100.
Database NCBI Protein dated Apr. 11, 1996, Accession No. AAA96779.
Database NCBI Protein dated Mar. 23, 2002, Accession No. AAA92933.
Database NCBI Protein, dated Mar. 23, 2002, Accession No. AAL92941.
Database NCBL Protein, dated Aug. 30, 1993, Accession No. AAA38584.
David et al., A significant reduction in the incidence of collagen induced arthritis in mice treated with anti-TCRV-beta antibodies, Cell Biochem. (1991) 179.
DeGiorgi et al., "Induction of foetal lethality in AKR offspring after repeated inoculations into AKR females of anti-TCR/V beta 6 monoclonal antibody," Res. Immunol (1993) 144(4):245-255.
DeGiorgi et al., "Murine hybridomas secreting monoclonal antibodies reacting with Misa antigens," Exp. Clin. Immunogenet. (1993) 10(4):219-223.
Ding et al., "Targeting age-related macular degeneration with Alzheimer's disease based immunotherapies: anti-amyloid-beta antibody attenuates pathologies in an age-related macular degeneration mouse model," Vision Research, Pergamon Press, Oxford, GB (2007) 48(3):339-345.
Dorronsoro et al., "Peripheral and dual binding site inhibitors of acetylcholinesterase as neurodegenerative disease-modifying agents," Exp. Opin. Ther. Pat. (2003) 13(11):1725-1732.
Frenkel et al., "Modulation of Alzheimer's beta-amyloid neurotoxicity by site-directed single-chain antibody," J. Neuroimmunol. (2000) 106(1-2):23-31.

Fujimoro et al., "Production and characterization of monoclonal antibodies specific to multi-ubiquitin chains of polyubiquitinated proteins," FEBS (1994) 349:173-180.
Fujimoro et al., "Production of antipolyubiquitin monoclonal antibodies and their use for characterization and isolation of polyubiquitinated proteins," Meth. Enzymol. (2005) 399:75-86.
Fukuchi et al., "Amelioration of amyloid load by anti-Abeta single-chain antibody in Alzheimer mouse model," Biochem. Biophys. Res. Commun. (2006) 344(1):79-86.
Guo et al., "Targeting amyloid-beta in glaucoma treatment," Proc. Natl. Acad. Sci. USA (2007) 104(33):13444-13449.
Hicke, "Protein regulation by monoubiquitin," Nat. Rev. (2001) 2:196-201.
Kim et al., "Development of conformation-specific antibodies for neutralization of beta-amyloid oligomers," Neurobiol. Aging (2004) 25(1):S145, p. 1-175 Abstract.
Kisilevsky et al., "Arresting amyloidosis in vivo using small-molecule anionic sulphonates or sulphates: implications for Alzheimer's disease," Nat. Med. (1995) 1(2):143-148.
Kisilevsky, "Anti-amyloid drugs potential in the treatment of diseases associated with aging," Drugs Aging (1996) 8(2):75-83.
Langdon et al., "Germline sequences of VH7183 gene family members in C57BL/6 mice demonstrate natural selection of particular sequences during recent evolution," Immunogen (2000) 51:241-245.
Lee et al., "Molecular cloning of agonistic and antagonistic monoclonal antibodies against human 4-IBB," Eur. J. Immunogenet. (2002) 29(5):449-452.
LeVine, H, III., "4,4'-dianilino-1,1''-binaphthyl-5'-disulfonate (bis-ANS) reports on non-beta-sheet conformers of Alzheimer's peptide beta (1-40)," Arch Biochem. Biophys. (2002) 404:106-115.
Liu, et al., "Single chain variable fragments against beta-amyloid (Abeta) can inhibit Abeta aggregation and prevent Abeta-induced neurotoxicity," Biochem. (2004) 43:6959-6967.
Lund et al., "Oligosaccharide-protein interactions in IgG can modulate recognition by Fc-gamma receptors," FASEB J. (1995) 9(1):115-119.
McKinnon et al., "Caspase activation and amyloid precursor protein cleavage in rat ocular hypertension," Investigative Ophthalmology & Visual Science (2002) 43(4):1077-1087.
McLaurin et al., "therapeutically effective antibodies against amyloid-beta peptide target amyloid-beta residues 4-10 and inhibit cytotoxicity and fibrillogenesis," Nat. Med. (2002) 8(11):1263-1269.
Moretto et al., "Conformation-sensitive antibodies against Alzheimer amyloid-beta by immunization with a thioredoxin-constrained B-cell epitope peptide," J. Biol. Chem. (2007) 282(15):11436-11445.
Nemes et al., "Cross-linking of obiquitin, HSP27, parkin, and alpha-synuclein by gamma-glutamyl-ϵ-lysine bonds in Alzheimer's neurofibrillary tangles," FASEB J. (2004) 18:1135-1137.
Nicolau et al., "A liposome-based therapetuci vaccine against beta-amyloid plaques on the pancreas of transgenic NORBA mice," Proc. Natl. Acad. Sci. USA (2002) 99(4):2332-2337.
Rzepecki et al., "Prevention of Alzheimer's disease-associated Abeta aggregation by rationally designed non-peptide beta-sheet ligands," J. Biol. Chem. (2004) 279(46):47497-47505.
Schable et al., "Characteristics of the immunoglobulin V kappa genes, pseudogenes, relics and orphons in the mouse genome," Eur. J. Immunol (1999) 29:2082-2086.
Schenk et al., "Immunization with amyloid-beta attenuates Alzheimer'disease-like pathology in the PDAPP mouse," Nature (1999) 400:173-177.
Solomon et al., "disaggregation of Alzheimer beta-amyloid by site-directed mAb," Proc. Natl. Acad. Sci. USA (1997) 94:4109-4112.
Solomon et al., "Monoclonal antibodies inhibit in vitro fibrillar aggregation fo the Alzheimer beta-amyloid peptide," Proc. Natl. Acad. Sci. USA (1996) 93:452-455.
Tenno et al., "Structural basis for distinct roles of Lys63- and Lys48-linked polyubiquitin chains," Genes to Cells (1994) 9:865-875.
Van Gool et al., "Concentrations of amyloid-beta protein in cerebrospinal fluid increase with age in patients free from neurodegenerative disease," Neurosci Lett. (1994) 172(1-2):122-124.

(56) References Cited

OTHER PUBLICATIONS

Weaver-Feldhaus et al., "Yeast mating for combinatorial Fab library generation and surface display," FEBS Lett. (2004) 564(2):24-34.
U.S. Patent Office Notice of Allowance for U.S. Appl. No. 13/102,713 dated Mar. 14, 2014 (9 pages).
United States Patent Office Action for U.S. Appl. No. 13/195,533 dated Feb. 24, 2014 (9 pages).
Barghorn, S., et al., "Globular amyloid beta-peptidel-42 oligomer—a homogenous and stable neuropathological protein in Alzheimer's disease," Journal of Neurochemistry, vol. 95, 2005, pp. 834-847, abstract.
Lambert, M.P., et al., "Monoclonal antibodies that target pathological assemblies of A beta," Journal of Neurochemistry, vol. 100, No. 1, Jan. 2007, pp. 23-25., abstract.
Asakura, K., et al., "Alpha-Eudesmol, a P/Q-type Ca2+ channel blocker, inhibits neurogenic vasodilatation and extravasation following electrical stimulation of trigeminal ganglion," Brain Research, vol. 873, 2000, pp. 94-101, abstract.
Asakura, K., et al., "P/Q-type Ca2+ channel blocker gama-agatoxin IVA protects against brain injury after focal ischemia in rats," Brain Research, vol. 776, 1997, pp. 140-145, abstract.
Mueller, W., et al., "Apolipoprotein E isoforms increase intracellular Ca2+ differentially through a omega-agatoxin IVA-sensitive Ca2+-channel," Brain Pathology, Zuerich, vol. 8, No. 4, Oct. 1, 1998, pp. 641-653.
Hardy, J., Science, pp. 353-356 (2002).
Mattson, M.P., Nature, 430, pp. 631-639.
Qian, J., et al., Neurosci. 21, pp. 3721-3728 (2001).
United States Patent Office Notice of Allowance for U.S. Appl. No. 13/102,713 dated Jun. 24, 2014.

* cited by examiner

A-Beta wash

A-Beta control glob washout

SEQUENCE LISTING

<160> NUMBER OF SEQ ID NOS: 3

<210> SEQ ID NO 1
<211> LENGTH: 2505
<212> TYPE: PRT
<213> ORGANISM: Homo sapiens

<400> SEQUENCE: 1

```
Met Ala Arg Phe Gly Asp Glu Met Pro Ala Arg Tyr Gly Gly Gly
1               5                   10                  15

Ser Gly Ala Ala Ala Gly Val Val Gly Ser Gly Gly Gly Arg Gly
            20                  25                  30

Ala Gly Gly Ser Arg Gln Gly Gly Gln Pro Gly Ala Gln Arg Met Tyr
        35                  40                  45

Lys Gln Ser Met Ala Gln Arg Ala Arg Thr Met Ala Leu Tyr Asn Pro
50                      55                  60

Ile Pro Val Arg Gln Asn Cys Leu Thr Val Asn Arg Ser Leu Phe Leu
65                  70                  75                  80

Phe Ser Glu Asp Asn Val Val Arg Lys Tyr Ala Lys Lys Ile Thr Glu
                85                  90                  95

Trp Pro Pro Phe Glu Tyr Met Ile Leu Ala Thr Ile Ile Ala Asn Cys
                100                 105                 110

Ile Val Leu Ala Leu Glu Gln His Leu Pro Asp Asp Asp Lys Thr Pro
            115                 120                 125

Met Ser Glu Arg Leu Asp Asp Thr Glu Pro Tyr Phe Ile Gly Ile Phe
    130                 135                 140

Cys Phe Glu Ala Gly Ile Lys Ile Ile Ala Leu Gly Phe Ala Phe His
145                 150                 155                 160

Lys Gly Ser Tyr Leu Arg Asn Gly Trp Asn Val Met Asp Phe Val Val
                165                 170                 175

Val Leu Thr Gly Ile Leu Ala Thr Val Gly Thr Glu Phe Asp Leu Arg
            180                 185                 190

Thr Leu Arg Ala Val Arg Val Leu Arg Pro Leu Lys Leu Val Ser Gly
    195                 200                 205

Ile Pro Ser Leu Gln Val Val Leu Lys Ser Ile Met Lys Ala Met Ile
210                 215                 220

Pro Leu Leu Gln Ile Gly Leu Leu Phe Phe Ala Ile Leu Ile Phe
225                 230                 235                 240

Ala Ile Ile Gly Leu Glu Phe Tyr Met Gly Lys Phe His Thr Thr Cys
            245                 250                 255

Phe Glu Glu Gly Thr Asp Asp Ile Gln Gly Glu Ser Pro Ala Pro Cys
            260                 265                 270

Gly Thr Glu Glu Pro Ala Arg Thr Cys Pro Asn Gly Thr Lys Cys Gln
        275                 280                 285

Pro Tyr Trp Glu Gly Pro Asn Asn Gly Ile Thr Gln Phe Asp Asn Ile
        290                 295                 300

Leu Phe Ala Val Leu Thr Val Phe Gln Cys Ile Thr Met Glu Gly Trp
305                 310                 315                 320

Thr Asp Leu Leu Tyr Asn Ser Asn Asp Ala Ser Gly Asn Thr Trp Asn
                325                 330                 335

Trp Leu Tyr Phe Ile Pro Leu Ile Ile Ile Gly Ser Phe Phe Met Leu
            340                 345                 350

Asn Leu Val Leu Gly Val Leu Ser Gly Glu Phe Ala Lys Glu Arg Glu
                355                 360                 365

Arg Val Glu Asn Arg Arg Ala Phe Leu Lys Leu Arg Arg Gln Gln Gln
    370                 375                 380

Ile Glu Arg Glu Leu Asn Gly Tyr Met Glu Trp Ile Ser Lys Ala Glu
385                 390                 395                 400

Glu Val Ile Leu Ala Glu Asp Glu Thr Asp Gly Glu Gln Arg His Pro
                405                 410                 415
```

```
Phe Asp Gly Ala Leu Arg Arg Thr Thr Ile Lys Lys Ser Lys Thr Asp
                420                 425                 430

Leu Leu Asn Pro Glu Glu Ala Glu Asp Gln Leu Ala Asp Ile Ala Ser
            435                 440                 445

Val Gly Ser Pro Phe Ala Arg Ala Ser Ile Lys Ser Ala Lys Leu Glu
        450                 455                 460

Asn Ser Thr Phe Phe His Lys Lys Glu Arg Arg Met Arg Phe Tyr Ile
465                 470                 475                 480

Arg Arg Met Val Lys Thr Gln Ala Phe Tyr Trp Thr Val Leu Ser Leu
                485                 490                 495

Val Ala Leu Asn Thr Leu Cys Val Ala Ile Val His Tyr Asn Gln Pro
            500                 505                 510

Glu Trp Leu Ser Asp Phe Leu Tyr Tyr Ala Glu Phe Ile Phe Leu Gly
        515                 520                 525

Leu Phe Met Ser Glu Met Phe Ile Lys Met Tyr Gly Leu Gly Thr Arg
        530                 535                 540

Pro Tyr Phe His Ser Ser Phe Asn Cys Phe Asp Cys Gly Val Ile Ile
545                 550                 555                 560

Gly Ser Ile Phe Glu Val Ile Trp Ala Val Ile Lys Pro Gly Thr Ser
                565                 570                 575

Phe Gly Ile Ser Val Leu Arg Ala Leu Arg Leu Leu Arg Ile Phe Lys
            580                 585                 590

Val Thr Lys Tyr Trp Ala Ser Leu Arg Asn Leu Val Val Ser Leu Leu
        595                 600                 605

Asn Ser Met Lys Ser Ile Ile Ser Leu Leu Phe Leu Leu Phe Leu Phe
610                 615                 620

Ile Val Val Phe Ala Leu Leu Gly Met Gln Leu Phe Gly Gly Gln Phe
625                 630                 635                 640

Asn Phe Asp Glu Gly Thr Pro Pro Thr Asn Phe Asp Thr Phe Pro Ala
                645                 650                 655

Ala Ile Met Thr Val Phe Gln Ile Leu Thr Gly Glu Asp Trp Asn Glu
            660                 665                 670

Val Met Tyr Asp Gly Ile Lys Ser Gln Gly Gly Val Gln Gly Gly Met
        675                 680                 685

Val Phe Ser Ile Tyr Phe Ile Val Leu Thr Leu Phe Gly Asn Tyr Thr
        690                 695                 700

Leu Leu Asn Val Phe Leu Ala Ile Ala Val Asp Asn Leu Ala Asn Ala
705                 710                 715                 720

Gln Glu Leu Thr Lys Asp Glu Gln Glu Glu Glu Ala Ala Asn Gln
                725                 730                 735

Lys Leu Ala Leu Gln Lys Ala Lys Glu Val Ala Glu Val Ser Pro Leu
            740                 745                 750

Ser Ala Ala Asn Met Ser Ile Ala Val Lys Glu Gln Gln Lys Asn Gln
        755                 760                 765

Lys Pro Ala Lys Ser Val Trp Glu Gln Arg Thr Ser Glu Met Arg Lys
        770                 775                 780

Gln Asn Leu Leu Ala Ser Arg Glu Ala Leu Tyr Asn Glu Met Asp Pro
785                 790                 795                 800

Asp Glu Arg Trp Lys Ala Ala Tyr Thr Arg His Leu Arg Pro Asp Met
                805                 810                 815

Lys Thr His Leu Asp Arg Pro Leu Val Val Asp Pro Gln Glu Asn Arg
            820                 825                 830

Asn Asn Asn Thr Asn Lys Ser Arg Ala Ala Glu Pro Thr Val Asp Gln
```

-continued

```
            835                 840                 845
Arg Leu Gly Gln Gln Arg Ala Glu Asp Phe Leu Arg Lys Gln Ala Arg
        850                 855                 860
Tyr His Asp Arg Ala Arg Asp Pro Ser Gly Ser Ala Gly Leu Asp Ala
865                 870                 875                 880
Arg Arg Pro Trp Ala Gly Ser Gln Glu Ala Glu Leu Ser Arg Glu Gly
                    885                 890                 895
Pro Tyr Gly Arg Glu Ser Asp His His Ala Arg Glu Gly Ser Leu Glu
                900                 905                 910
Gln Pro Gly Phe Trp Glu Gly Glu Ala Glu Arg Gly Lys Ala Gly Asp
            915                 920                 925
Pro His Arg Arg His Val His Arg Gln Gly Gly Ser Arg Glu Ser Arg
        930                 935                 940
Ser Gly Ser Pro Arg Thr Gly Ala Asp Gly Glu His Arg His Arg
945                 950                 955                 960
Ala His Arg Arg Pro Gly Glu Glu Gly Pro Glu Asp Lys Ala Glu Arg
                    965                 970                 975
Arg Ala Arg His Arg Glu Gly Ser Arg Pro Ala Arg Gly Gly Glu Gly
                980                 985                 990
Glu Gly Glu Gly Pro Asp Gly Gly  Glu Arg Arg Arg Arg  His Arg His
            995                 1000                1005
Gly Ala  Pro Ala Thr Tyr Glu   Gly Asp Ala Arg  Arg   Glu Asp Lys
        1010                1015                1020
Glu Arg  Arg His Arg Arg Arg   Lys Glu Asn Gln Gly   Ser Gly Val
        1025                1030                1035
Pro Val  Ser Gly Pro Asn Leu   Ser Thr Thr Arg Pro   Ile Gln Gln
        1040                1045                1050
Asp Leu  Gly Arg Gln Asp Pro   Pro Leu Ala Glu Asp   Ile Asp Asn
        1055                1060                1065
Met Lys  Asn Asn Lys Leu Ala   Thr Ala Glu Ser Ala   Ala Pro His
        1070                1075                1080
Gly Ser  Leu Gly His Ala Gly   Leu Pro Gln Ser Pro   Ala Lys Met
        1085                1090                1095
Gly Asn  Ser Thr Asp Pro Gly   Pro Met Leu Ala Ile   Pro Ala Met
        1100                1105                1110
Ala Thr  Asn Pro Gln Asn Ala   Ala Ser Arg Arg Thr   Pro Asn Asn
        1115                1120                1125
Pro Gly  Asn Pro Ser Asn Pro   Gly Pro Pro Lys Thr   Pro Glu Asn
        1130                1135                1140
Ser Leu  Ile Val Thr Asn Pro   Ser Gly Thr Gln Thr   Asn Ser Ala
        1145                1150                1155
Lys Thr  Ala Arg Lys Pro Asp   His Thr Thr Val Asp   Ile Pro Pro
        1160                1165                1170
Ala Cys  Pro Pro Pro Leu Asn   His Thr Val Val Gln   Val Asn Lys
        1175                1180                1185
Asn Ala  Asn Pro Asp Pro Leu   Pro Lys Lys Glu Glu   Glu Lys Lys
        1190                1195                1200
Glu Glu  Glu Glu Asp Asp Arg   Gly Glu Asp Gly Pro   Lys Pro Met
        1205                1210                1215
Pro Pro  Tyr Ser Ser Met Phe   Ile Leu Ser Thr Thr   Asn Pro Leu
        1220                1225                1230
Arg Arg  Leu Cys His Tyr Ile   Leu Asn Leu Arg Tyr   Phe Glu Met
        1235                1240                1245
```

```
Cys Ile Leu Met Val Ile Ala Met Ser Ser Ile Ala Leu Ala Ala
    1250            1255            1260

Glu Asp Pro Val Gln Pro Asn Ala Pro Arg Asn Asn Val Leu Arg
    1265            1270            1275

Tyr Phe Asp Tyr Val Phe Thr Gly Val Phe Thr Phe Glu Met Val
    1280            1285            1290

Ile Lys Met Ile Asp Leu Gly Leu Val Leu His Gln Gly Ala Tyr
    1295            1300            1305

Phe Arg Asp Leu Trp Asn Ile Leu Asp Phe Ile Val Val Ser Gly
    1310            1315            1320

Ala Leu Val Ala Phe Ala Phe Thr Gly Asn Ser Lys Gly Lys Asp
    1325            1330            1335

Ile Asn Thr Ile Lys Ser Leu Arg Val Leu Arg Val Leu Arg Pro
    1340            1345            1350

Leu Lys Thr Ile Lys Arg Leu Pro Lys Leu Lys Ala Val Phe Asp
    1355            1360            1365

Cys Val Val Asn Ser Leu Lys Asn Val Phe Asn Ile Leu Ile Val
    1370            1375            1380

Tyr Met Leu Phe Met Phe Ile Phe Ala Val Val Ala Val Gln Leu
    1385            1390            1395

Phe Lys Gly Lys Phe Phe His Cys Thr Asp Glu Ser Lys Glu Phe
    1400            1405            1410

Glu Lys Asp Cys Arg Gly Lys Tyr Leu Leu Tyr Glu Lys Asn Glu
    1415            1420            1425

Val Lys Ala Arg Asp Arg Glu Trp Lys Lys Tyr Glu Phe His Tyr
    1430            1435            1440

Asp Asn Val Leu Trp Ala Leu Leu Thr Leu Phe Thr Val Ser Thr
    1445            1450            1455

Gly Glu Gly Trp Pro Gln Val Leu Lys His Ser Val Asp Ala Thr
    1460            1465            1470

Phe Glu Asn Gln Gly Pro Ser Pro Gly Tyr Arg Met Glu Met Ser
    1475            1480            1485

Ile Phe Tyr Val Val Tyr Phe Val Val Phe Pro Phe Phe Phe Val
    1490            1495            1500

Asn Ile Phe Val Ala Leu Ile Ile Thr Phe Gln Glu Gln Gly
    1505            1510            1515

Asp Lys Met Met Glu Glu Tyr Ser Leu Glu Lys Asn Glu Arg Ala
    1520            1525            1530

Cys Ile Asp Phe Ala Ile Ser Ala Lys Pro Leu Thr Arg His Met
    1535            1540            1545

Pro Gln Asn Lys Gln Ser Phe Gln Tyr Arg Met Trp Gln Phe Val
    1550            1555            1560

Val Ser Pro Pro Phe Glu Tyr Thr Ile Met Ala Met Ile Ala Leu
    1565            1570            1575

Asn Thr Ile Val Leu Met Met Lys Phe Tyr Gly Ala Ser Val Ala
    1580            1585            1590

Tyr Glu Asn Ala Leu Arg Val Phe Asn Ile Val Phe Thr Ser Leu
    1595            1600            1605

Phe Ser Leu Glu Cys Val Leu Lys Val Met Ala Phe Gly Ile Leu
    1610            1615            1620

Asn Tyr Phe Arg Asp Ala Trp Asn Ile Phe Asp Phe Val Thr Val
    1625            1630            1635
```

```
Leu Gly Ser Ile Thr Asp Ile Leu Val Thr Glu Phe Gly Asn Asn
    1640            1645                1650

Phe Ile Asn Leu Ser Phe Leu Arg Leu Phe Arg Ala Ala Arg Leu
    1655            1660                1665

Ile Lys Leu Leu Arg Gln Gly Tyr Thr Ile Arg Ile Leu Leu Trp
    1670            1675                1680

Thr Phe Val Gln Ser Phe Lys Ala Leu Pro Tyr Val Cys Leu Leu
    1685            1690                1695

Ile Ala Met Leu Phe Phe Ile Tyr Ala Ile Ile Gly Met Gln Val
    1700            1705                1710

Phe Gly Asn Ile Gly Ile Asp Val Glu Asp Glu Asp Ser Asp Glu
    1715            1720                1725

Asp Glu Phe Gln Ile Thr Glu His Asn Asn Phe Arg Thr Phe Phe
    1730            1735                1740

Gln Ala Leu Met Leu Leu Phe Arg Ser Ala Thr Gly Glu Ala Trp
    1745            1750                1755

His Asn Ile Met Leu Ser Cys Leu Ser Gly Lys Pro Cys Asp Lys
    1760            1765                1770

Asn Ser Gly Ile Leu Thr Arg Glu Cys Gly Asn Glu Phe Ala Tyr
    1775            1780                1785

Phe Tyr Phe Val Ser Phe Ile Phe Leu Cys Ser Phe Leu Met Leu
    1790            1795                1800

Asn Leu Phe Val Ala Val Ile Met Asp Asn Phe Glu Tyr Leu Thr
    1805            1810                1815

Arg Asp Ser Ser Ile Leu Gly Pro His His Leu Asp Glu Tyr Val
    1820            1825                1830

Arg Val Trp Ala Glu Tyr Asp Pro Ala Ala Trp Gly Arg Met Pro
    1835            1840                1845

Tyr Leu Asp Met Tyr Gln Met Leu Arg His Met Ser Pro Pro Leu
    1850            1855                1860

Gly Leu Gly Lys Lys Cys Pro Ala Arg Val Ala Tyr Lys Arg Leu
    1865            1870                1875

Leu Arg Met Asp Leu Pro Val Ala Asp Asp Asn Thr Val His Phe
    1880            1885                1890

Asn Ser Thr Leu Met Ala Leu Ile Arg Thr Ala Leu Asp Ile Lys
    1895            1900                1905

Ile Ala Lys Gly Gly Ala Asp Lys Gln Gln Met Asp Ala Glu Leu
    1910            1915                1920

Arg Lys Glu Met Met Ala Ile Trp Pro Asn Leu Ser Gln Lys Thr
    1925            1930                1935

Leu Asp Leu Leu Val Thr Pro His Lys Ser Thr Asp Leu Thr Val
    1940            1945                1950

Gly Lys Ile Tyr Ala Ala Met Met Ile Met Glu Tyr Tyr Arg Gln
    1955            1960                1965

Ser Lys Ala Lys Lys Leu Gln Ala Met Arg Glu Glu Gln Asp Arg
    1970            1975                1980

Thr Pro Leu Met Phe Gln Arg Met Glu Pro Pro Ser Pro Thr Gln
    1985            1990                1995

Glu Gly Gly Pro Gly Gln Asn Ala Leu Pro Ser Thr Gln Leu Asp
    2000            2005                2010

Pro Gly Gly Ala Leu Met Ala His Glu Ser Gly Leu Lys Glu Ser
    2015            2020                2025

Pro Ser Trp Val Thr Gln Arg Ala Gln Glu Met Phe Gln Lys Thr
```

-continued

```
            2030                2035                2040
Gly Thr Trp Ser Pro Glu Gln Gly Pro Pro Thr Asp Met Pro Asn
            2045                2050                2055
Ser Gln Pro Asn Ser Gln Ser Val Glu Met Arg Glu Met Gly Arg
            2060                2065                2070
Asp Gly Tyr Ser Asp Ser Glu His Tyr Leu Pro Met Glu Gly Gln
            2075                2080                2085
Gly Arg Ala Ala Ser Met Pro Arg Leu Pro Ala Glu Asn Gln Arg
            2090                2095                2100
Arg Arg Gly Arg Pro Arg Gly Asn Asn Leu Ser Thr Ile Ser Asp
            2105                2110                2115
Thr Ser Pro Met Lys Arg Ser Ala Ser Val Leu Gly Pro Lys Ala
            2120                2125                2130
Arg Arg Leu Asp Asp Tyr Ser Leu Glu Arg Val Pro Pro Glu Glu
            2135                2140                2145
Asn Gln Arg His His Gln Arg Arg Asp Arg Ser His Arg Ala
            2150                2155                2160
Ser Glu Arg Ser Leu Gly Arg Tyr Thr Asp Val Asp Thr Gly Leu
            2165                2170                2175
Gly Thr Asp Leu Ser Met Thr Thr Gln Ser Gly Asp Leu Pro Ser
            2180                2185                2190
Lys Glu Arg Asp Gln Glu Arg Gly Arg Pro Lys Asp Arg Lys His
            2195                2200                2205
Arg Gln His His His His His His His His His Pro Pro Pro
            2210                2215                2220
Pro Asp Lys Asp Arg Tyr Ala Gln Glu Arg Pro Asp His Gly Arg
            2225                2230                2235
Ala Arg Ala Arg Asp Gln Arg Trp Ser Arg Ser Pro Ser Glu Gly
            2240                2245                2250
Arg Glu His Met Ala His Arg Gln Gly Ser Ser Ser Val Ser Gly
            2255                2260                2265
Ser Pro Ala Pro Ser Thr Ser Gly Thr Ser Thr Pro Arg Arg Gly
            2270                2275                2280
Arg Arg Gln Leu Pro Gln Thr Pro Ser Thr Pro Arg Pro His Val
            2285                2290                2295
Ser Tyr Ser Pro Val Ile Arg Lys Ala Gly Gly Ser Gly Pro Pro
            2300                2305                2310
Gln Gln Gln Gln Gln Gln Gln Gln Gln Gln Ala Val Ala Arg
            2315                2320                2325
Pro Gly Arg Ala Ala Thr Ser Gly Pro Arg Arg Tyr Pro Gly Pro
            2330                2335                2340
Thr Ala Glu Pro Leu Ala Gly Asp Arg Pro Pro Thr Gly Gly His
            2345                2350                2355
Ser Ser Gly Arg Ser Pro Arg Met Glu Arg Arg Val Pro Gly Pro
            2360                2365                2370
Ala Arg Ser Glu Ser Pro Arg Ala Cys Arg His Gly Gly Ala Arg
            2375                2380                2385
Trp Pro Ala Ser Gly Pro His Val Ser Glu Gly Pro Pro Gly Pro
            2390                2395                2400
Arg His His Gly Tyr Tyr Arg Gly Ser Asp Tyr Asp Glu Ala Asp
            2405                2410                2415
Gly Pro Gly Ser Gly Gly Gly Glu Glu Ala Met Ala Gly Ala Tyr
            2420                2425                2430
```

-continued

Asp Ala Pro Pro Val Arg His Ala Ser Ser Gly Ala Thr Gly
    2435                2440                2445

Arg Ser Pro Arg Thr Pro Arg Ala Ser Gly Pro Ala Cys Ala Ser
2450                2455                2460

Pro Ser Arg His Gly Arg Arg Leu Pro Asn Gly Tyr Tyr Pro Ala
    2465                2470                2475

His Gly Leu Ala Arg Pro Arg Gly Pro Gly Ser Arg Lys Gly Leu
2480                2485                2490

His Glu Pro Tyr Ser Glu Ser Asp Asp Asp Trp Cys
    2495                2500                2505

<210> SEQ ID NO 2
<211> LENGTH: 1145
<212> TYPE: PRT
<213> ORGANISM: Homo sapiens
<220> FEATURE:
<221> NAME/KEY: MISC_FEATURE
<222> LOCATION: (1)..(1145)
<223> OTHER INFORMATION: PQ calcium channel, alpha 2/delta subunit 2
      isoform a

<400> SEQUENCE: 2

Met Ala Val Pro Ala Arg Thr Cys Gly Ala Ser Arg Pro Gly Pro Ala
1               5                   10                  15

Arg Thr Ala Arg Pro Trp Pro Gly Cys Gly Pro His Pro Gly Pro Gly
            20                  25                  30

Thr Arg Arg Pro Thr Ser Gly Pro Pro Arg Pro Leu Trp Leu Leu Leu
        35                  40                  45

Pro Leu Leu Pro Leu Leu Ala Ala Pro Gly Ala Ser Ala Tyr Ser Phe
    50                  55                  60

Pro Gln Gln His Thr Met Gln His Trp Ala Arg Arg Leu Glu Gln Glu
65                  70                  75                  80

Val Asp Gly Val Met Arg Ile Phe Gly Gly Val Gln Gln Leu Arg Glu
                85                  90                  95

Ile Tyr Lys Asp Asn Arg Asn Leu Phe Glu Val Gln Glu Asn Glu Pro
            100                 105                 110

Gln Lys Leu Val Glu Lys Val Ala Gly Asp Ile Glu Ser Leu Leu Asp
        115                 120                 125

Arg Lys Val Gln Ala Leu Lys Arg Leu Ala Asp Ala Ala Glu Asn Phe
    130                 135                 140

Gln Lys Ala His Arg Trp Gln Asp Asn Ile Lys Glu Glu Asp Ile Val
145                 150                 155                 160

Tyr Tyr Asp Ala Lys Ala Asp Ala Glu Leu Asp Asp Pro Glu Ser Glu
                165                 170                 175

Asp Val Glu Arg Gly Ser Lys Ala Ser Thr Leu Arg Leu Asp Phe Ile
            180                 185                 190

Glu Asp Pro Asn Phe Lys Asn Lys Val Asn Tyr Ser Tyr Ala Ala Val
        195                 200                 205

Gln Ile Pro Thr Asp Ile Tyr Lys Gly Ser Thr Val Ile Leu Asn Glu
    210                 215                 220

Leu Asn Trp Thr Glu Ala Leu Glu Asn Val Phe Met Glu Asn Arg Arg
225                 230                 235                 240

Gln Asp Pro Thr Leu Leu Trp Gln Val Phe Gly Ser Ala Thr Gly Val
                245                 250                 255

Thr Arg Tyr Tyr Pro Ala Thr Pro Trp Arg Ala Pro Lys Lys Ile Asp
            260                 265                 270

```
Leu Tyr Asp Val Arg Arg Pro Trp Tyr Ile Gln Gly Ala Ser Ser
        275                 280                 285

Pro Lys Asp Met Val Ile Ile Val Asp Val Ser Gly Ser Val Ser Gly
290                 295                 300

Leu Thr Leu Lys Leu Met Lys Thr Ser Val Cys Glu Met Leu Asp Thr
305                 310                 315                 320

Leu Ser Asp Asp Asp Tyr Val Asn Val Ala Ser Phe Asn Glu Lys Ala
                325                 330                 335

Gln Pro Val Ser Cys Phe Thr His Leu Val Gln Ala Asn Val Arg Asn
                340                 345                 350

Lys Lys Val Phe Lys Glu Ala Val Gln Gly Met Val Ala Lys Gly Thr
                355                 360                 365

Thr Gly Tyr Lys Ala Gly Phe Glu Tyr Ala Phe Asp Gln Leu Gln Asn
        370                 375                 380

Ser Asn Ile Thr Arg Ala Asn Cys Asn Lys Met Ile Met Met Phe Thr
385                 390                 395                 400

Asp Gly Gly Glu Asp Arg Val Gln Asp Val Phe Glu Lys Tyr Asn Trp
                405                 410                 415

Pro Asn Arg Thr Val Arg Val Phe Thr Phe Ser Val Gly Gln His Asn
                420                 425                 430

Tyr Asp Val Thr Pro Leu Gln Trp Met Ala Cys Ala Asn Lys Gly Tyr
        435                 440                 445

Tyr Phe Glu Ile Pro Ser Ile Gly Ala Ile Arg Ile Asn Thr Gln Glu
        450                 455                 460

Tyr Leu Asp Val Leu Gly Arg Pro Met Val Leu Ala Gly Lys Glu Ala
465                 470                 475                 480

Lys Gln Val Gln Trp Thr Asn Val Tyr Glu Asp Ala Leu Gly Leu Gly
                485                 490                 495

Leu Val Val Thr Gly Thr Leu Pro Val Phe Asn Leu Thr Gln Asp Gly
                500                 505                 510

Pro Gly Glu Lys Lys Asn Gln Leu Ile Leu Gly Val Met Gly Ile Asp
        515                 520                 525

Val Ala Leu Asn Asp Ile Lys Arg Leu Thr Pro Asn Tyr Thr Leu Gly
530                 535                 540

Ala Asn Gly Tyr Val Phe Ala Ile Asp Leu Asn Gly Tyr Val Leu Leu
545                 550                 555                 560

His Pro Asn Leu Lys Pro Gln Thr Thr Asn Phe Arg Glu Pro Val Thr
                565                 570                 575

Leu Asp Phe Leu Asp Ala Glu Leu Glu Asp Glu Asn Lys Glu Glu Ile
                580                 585                 590

Arg Arg Ser Met Ile Asp Gly Asn Lys Gly His Lys Gln Ile Arg Thr
        595                 600                 605

Leu Val Lys Ser Leu Asp Glu Arg Tyr Ile Asp Glu Val Thr Arg Asn
        610                 615                 620

Tyr Thr Trp Val Pro Ile Arg Ser Thr Asn Tyr Ser Leu Gly Leu Val
625                 630                 635                 640

Leu Pro Pro Tyr Ser Thr Phe Tyr Leu Gln Ala Asn Leu Ser Asp Gln
                645                 650                 655

Ile Leu Gln Val Lys Tyr Phe Glu Phe Leu Pro Ser Ser Phe Glu
                660                 665                 670

Ser Glu Gly His Val Phe Ile Ala Pro Arg Glu Tyr Cys Lys Asp Leu
        675                 680                 685
```

```
Asn Ala Ser Asp Asn Asn Thr Glu Phe Leu Lys Asn Phe Ile Glu Leu
    690             695                 700

Met Glu Lys Val Thr Pro Asp Ser Lys Gln Cys Asn Asn Phe Leu Leu
705             710                 715                 720

His Asn Leu Ile Leu Asp Thr Gly Ile Thr Gln Gln Leu Val Glu Arg
            725                 730                 735

Val Trp Arg Asp Gln Asp Leu Asn Thr Tyr Ser Leu Leu Ala Val Phe
        740                 745                 750

Ala Ala Thr Asp Gly Gly Ile Thr Arg Val Phe Pro Asn Lys Ala Ala
    755                 760                 765

Glu Asp Trp Thr Glu Asn Pro Glu Pro Phe Asn Ala Ser Phe Tyr Arg
770             775                 780

Arg Ser Leu Asp Asn His Gly Tyr Val Phe Lys Pro Pro His Gln Asp
785             790                 795                 800

Ala Leu Leu Arg Pro Leu Glu Leu Glu Asn Asp Thr Val Gly Ile Leu
            805                 810                 815

Val Ser Thr Ala Val Glu Leu Ser Leu Gly Arg Arg Thr Leu Arg Pro
        820                 825                 830

Ala Val Val Gly Val Lys Leu Asp Leu Glu Ala Trp Ala Glu Lys Phe
    835                 840                 845

Lys Val Leu Ala Ser Asn Arg Thr His Gln Asp Gln Pro Gln Lys Cys
850                 855                 860

Gly Pro Asn Ser His Cys Glu Met Asp Cys Glu Val Asn Asn Glu Asp
865             870                 875                 880

Leu Leu Cys Val Leu Ile Asp Asp Gly Gly Phe Leu Val Leu Ser Asn
            885                 890                 895

Gln Asn His Gln Trp Asp Gln Val Gly Arg Phe Phe Ser Glu Val Asp
        900                 905                 910

Ala Asn Leu Met Leu Ala Leu Tyr Asn Asn Ser Phe Tyr Thr Arg Lys
    915                 920                 925

Glu Ser Tyr Asp Tyr Gln Ala Ala Cys Ala Pro Gln Pro Pro Gly Asn
    930                 935                 940

Leu Gly Ala Ala Pro Arg Gly Val Phe Val Pro Thr Val Ala Asp Phe
945             950                 955                 960

Leu Asn Leu Ala Trp Trp Thr Ser Ala Ala Trp Ser Leu Phe Gln
            965                 970                 975

Gln Leu Leu Tyr Gly Leu Ile Tyr His Ser Trp Phe Gln Ala Asp Pro
        980                 985                 990

Ala Glu Ala Glu Gly Ser Pro Glu Thr Arg Glu Ser Ser Cys Val Met
    995                 1000                1005

Lys Gln Thr Gln Tyr Tyr Phe Gly Ser Val Asn Ala Ser Tyr Asn
    1010            1015                1020

Ala Ile Ile Asp Cys Gly Asn Cys Ser Arg Leu Phe His Ala Gln
    1025            1030                1035

Arg Leu Thr Asn Thr Asn Leu Leu Phe Val Val Ala Glu Lys Pro
    1040            1045                1050

Leu Cys Ser Gln Cys Glu Ala Gly Arg Leu Leu Gln Lys Glu Thr
    1055            1060                1065

His Cys Pro Ala Asp Gly Pro Glu Gln Cys Glu Leu Val Gln Arg
    1070            1075                1080

Pro Arg Tyr Arg Arg Gly Pro His Ile Cys Phe Asp Tyr Asn Ala
    1085            1090                1095

Thr Glu Asp Thr Ser Asp Cys Gly Arg Gly Ala Ser Phe Pro Pro
```

-continued

```
                1100                1105                1110
Ser Leu Gly Val Leu Val Ser Leu Gln Leu Leu Leu Leu Leu Gly
            1115                1120                1125

Leu Pro Pro Arg Pro Gln Pro Gln Val Leu Val His Ala Ser Arg
        1130                1135                1140

Arg Leu
    1145

<210> SEQ ID NO 3
<211> LENGTH: 598
<212> TYPE: PRT
<213> ORGANISM: Homo sapiens
<220> FEATURE:
<221> NAME/KEY: MISC_FEATURE
<222> LOCATION: (1)..(598)
<223> OTHER INFORMATION: channel beta subunit PQ

<400> SEQUENCE: 3

Met Val Gln Lys Thr Ser Met Ser Arg Gly Pro Tyr Pro Pro Ser Gln
1               5                   10                  15

Glu Ile Pro Met Glu Val Phe Asp Pro Ser Pro Gln Gly Lys Tyr Ser
                20                  25                  30

Lys Arg Lys Gly Arg Phe Lys Arg Ser Asp Gly Ser Thr Ser Ser Asp
            35                  40                  45

Thr Thr Ser Asn Ser Phe Val Arg Gln Gly Ser Ala Glu Ser Tyr Thr
        50                  55                  60

Ser Arg Pro Ser Asp Ser Asp Val Ser Leu Glu Glu Asp Arg Glu Ala
65                  70                  75                  80

Leu Arg Lys Glu Ala Glu Arg Gln Ala Leu Ala Gln Leu Glu Lys Ala
                85                  90                  95

Lys Thr Lys Pro Val Ala Phe Ala Val Arg Thr Asn Val Gly Tyr Asn
            100                 105                 110

Pro Ser Pro Gly Asp Glu Val Pro Val Gln Gly Val Ala Ile Thr Phe
        115                 120                 125

Glu Pro Lys Asp Phe Leu His Ile Lys Glu Lys Tyr Asn Asn Asp Trp
130                 135                 140

Trp Ile Gly Arg Leu Val Lys Glu Gly Cys Glu Val Gly Phe Ile Pro
145                 150                 155                 160

Ser Pro Val Lys Leu Asp Ser Leu Arg Leu Leu Gln Glu Gln Lys Leu
                165                 170                 175

Arg Gln Asn Arg Leu Gly Ser Ser Lys Ser Gly Asp Asn Ser Ser Ser
            180                 185                 190

Ser Leu Gly Asp Val Val Thr Gly Thr Arg Arg Pro Thr Pro Pro Ala
        195                 200                 205

Ser Ala Lys Gln Lys Gln Lys Ser Thr Glu His Val Pro Pro Tyr Asp
    210                 215                 220

Val Val Pro Ser Met Arg Pro Ile Ile Leu Val Gly Pro Ser Leu Lys
225                 230                 235                 240

Gly Tyr Glu Val Thr Asp Met Met Gln Lys Ala Leu Phe Asp Phe Leu
                245                 250                 255

Lys His Arg Phe Asp Gly Arg Ile Ser Ile Thr Arg Val Thr Ala Asp
            260                 265                 270

Ile Ser Leu Ala Lys Arg Ser Val Leu Asn Asn Pro Ser Lys His Ile
        275                 280                 285

Ile Ile Glu Arg Ser Asn Thr Arg Ser Ser Leu Ala Glu Val Gln Ser
    290                 295                 300
```

-continued

```
Glu Ile Glu Arg Ile Phe Glu Leu Ala Arg Thr Leu Gln Leu Val Ala
305                 310                 315                 320

Leu Asp Ala Asp Thr Ile Asn His Pro Ala Gln Leu Ser Lys Thr Ser
                325                 330                 335

Leu Ala Pro Ile Ile Val Tyr Ile Lys Ile Thr Ser Pro Lys Val Leu
                340                 345                 350

Gln Arg Leu Ile Lys Ser Arg Gly Lys Ser Gln Ser Lys His Leu Asn
                355                 360                 365

Val Gln Ile Ala Ala Ser Glu Lys Leu Ala Gln Cys Pro Pro Glu Met
        370                 375                 380

Phe Asp Ile Ile Leu Asp Glu Asn Gln Leu Glu Asp Ala Cys Glu His
385                 390                 395                 400

Leu Ala Glu Tyr Leu Glu Ala Tyr Trp Lys Ala Thr His Pro Pro Ser
                405                 410                 415

Ser Thr Pro Pro Asn Pro Leu Leu Asn Arg Thr Met Ala Thr Ala Ala
                420                 425                 430

Leu Ala Ala Ser Pro Ala Pro Val Ser Asn Leu Gln Gly Pro Tyr Leu
                435                 440                 445

Ala Ser Gly Asp Gln Pro Leu Glu Arg Ala Thr Gly Glu His Ala Ser
        450                 455                 460

Met His Glu Tyr Pro Gly Glu Leu Gly Gln Pro Pro Gly Leu Tyr Pro
465                 470                 475                 480

Ser Ser His Pro Pro Gly Arg Ala Gly Thr Leu Arg Ala Leu Ser Arg
                485                 490                 495

Gln Asp Thr Phe Asp Ala Asp Thr Pro Gly Ser Arg Asn Ser Ala Tyr
                500                 505                 510

Thr Glu Leu Gly Asp Ser Cys Val Asp Met Glu Thr Asp Pro Ser Glu
                515                 520                 525

Gly Pro Gly Leu Gly Asp Pro Ala Gly Gly Gly Thr Pro Pro Ala Arg
                530                 535                 540

Gln Gly Ser Trp Glu Asp Glu Glu Asp Tyr Glu Glu Glu Leu Thr
545                 550                 555                 560

Asp Asn Arg Asn Arg Gly Arg Asn Lys Ala Arg Tyr Cys Ala Glu Gly
                565                 570                 575

Gly Gly Pro Val Leu Gly Arg Asn Lys Asn Glu Leu Glu Gly Trp Gly
                580                 585                 590

Arg Gly Val Tyr Ile Arg
        595
```

METHOD FOR THE TREATMENT OF AMYLOIDOSES

CROSS-REFERENCE TO RELATED APPLICATIONS

This is a U.S. national stage entry of International Patent Application No. PCT/EP2008/001548, filed on Feb. 27, 2008, which claims priority to European Patent Application No. 08000324.7, filed on Jan. 9, 2008, European Patent Application No. 07020258.5, filed on Oct. 16, 2007, and U.S. Patent Application No. 60/903,695, filed on Feb. 27, 2007, the entire contents of all of which are fully incorporated herein by reference.

The present invention relates to a method for the treatment of an amyloidosis such as Alzheimer's disease.

Alzheimer's disease (AD), the most frequent cause for dementia among the aged with an incidence of about 10% of the population above 65 years, is a dementing disorder characterized by a progressive loss of cognitive abilities and by characteristic neuro-pathological features comprising extracellular amyloid deposits, intracellular neuro-fibrillary tangles and neuronal loss in several brain regions (Mattson, M. P. Pathways towards and away from Alzheimer's disease. Nature 430, 631-639 (2004); Hardy, J. & Selkoe, D. J. The amyloid hypothesis of Alzheimer's disease: progress and problems on the road to therapeutics. Science 297, 353-356 (2002)). The principal constituents of the amyloid deposits are amyloid β peptides (Aβ) which arise from the β-amyloid precursor protein (APP) by proteolytic cleavage.

Both cerebral amyloid deposits and cognitive impairments very similar to those observed in Alzheimer's disease are also hallmarks of Down's syndrome (trisomy 21), which occurs at a frequency of about 1 in 800 births. Hence, Alzheimer's disease and Down's syndrome are jointly termed "amyloidoses".

Recently, however, it was shown that in amyloidoses soluble, globular Aβ oligomers, rather than the eponymous insoluble amyloid deposits, are the causative agents for the impairment of higher-level functions, such as memory function, as indicated by its suppressing effect on long-term potentiation (WO2004/067561; Barghorn S. et al., J. Neurochem. 95: 834-847 (2005); WO2006/094724).

The term "Aβ globulomer" here refers to a particular soluble, globular, non-covalent association of Aβ peptides, possessing homogeneity and distinct physical characteristics. Aβ globulomers are stable, non-fibrillar, oligomeric assemblies of Aβ peptides which are obtainable by incubation with anionic detergents, in particular as described in WO2004/067561. In contrast to Aβ monomer and fibrils, these globulomers are characterized by defined assembly numbers of subunits (WO2004/067561). The globulomers have a characteristic three-dimensional globular type structure ("molten globule", see Barghorn et al., J. Neurochem. 95: 834-847 (2005)). They have been shown to closely mimic the properties, behaviour and effects of naturally occurring soluble Aβ oligomers.

Soluble Aβ oligomer was found to impair the functioning of the central nervous system even before the onset of cytotoxicity. However, the exact mechanisms whereby soluble Aβ oligomer causes memory failure in amyloidoses has not been elucidated so far, and a lack of understanding of such mechanisms has so far hampered the development of rational therapeutic approaches for inhibiting the further progression of the disease or compensating the damage already done.

It was thus an object of the present invention to provide a new approach to the treatment of amyloidoses such as Alzheimer's disease, in particular to rehabilitating treatment such as the restoration of cognitive abilities in amyloidoses such as Alzheimer's disease.

Surprisingly, it was now found that Aβ globulomer exerts its detrimental effects essentially by hampering normal ion fluxes through the P/Q type presynaptic calcium channel, reducing presynaptic neurotransmitter release and inhibiting spontaneous synaptic activity and thereby interfering with the proper functioning of the central nervous system even before the onset of manifest neural cytotoxicity, and that inhibition of the interaction of the Aβ globulomer with the P/Q type presynaptic calcium channel is therefore effective in compensating these effects.

In a first aspect the present invention thus relates to a method for the treatment of an amyloidosis, preferably Alzheimer's disease, in a subject in need thereof, comprising administering an inhibitor of the interaction between Aβ globulomer and the P/Q type voltage-gated presynaptic calcium channel (hereinafter referred to as "Aβ-P/Q interaction") to said subject.

The P/Q type voltage-gated presynaptic calcium channel (the channel is also referred to as $Ca_v2.1$ channel and the associated currents as P/Q type currents) belongs to the group of voltage-gated calcium channels which mediate the influx of calcium ions into excitable cells. The opening state of a voltage-gated channel is controlled by the electrical state of the surrounding membrane; however, the responsiveness of the P/Q type voltage-gated presynaptic calcium channel to membrane depolarization is extensively modulated, both qualitatively and quantitatively, by and/or through its interaction partners.

As used herein, a "P/Q type voltage-gated presynaptic calcium channel" is a voltage-gated calcium channel that is functionally characterized by its sensitivity towards ω-agatoxin IVA (a well-known funnel web spider venom).

According to a particular embodiment, ω-agatoxin IVA acts as a gating modifier of the P/Q type voltage-gated presynaptic calcium channel (e.g., P type Kd=1-3 nM; Q type Kd=100-200 nM). Further, P/Q type voltage-gated presynaptic calcium channels according to the present invention may be characterized by one or more than one of the following features:

(i) requires strong depolarization for activation (high-voltage activation); and
(ii) no or slow inactivation.

The P/Q type voltage-gated presynaptic calcium channel according to the present invention comprises an α1 subunit. According to a particular embodiment of the invention, the α1 subunit has an amino acid sequence with at least 70%, advantageously at least 80%, preferably at least 90%, more preferably at least 95% and in particular at least 98%, e. g. at least 99%, amino acid sequence identity with the sequence SEQ ID NO:1. The α1 subunit incorporates the conduction pore, the voltage sensor and gating apparatus, and sites of channel regulation by second messengers, drugs, and toxins.

Usually, the P/Q type voltage-gated presynaptic calcium channel also comprises an α2-δ subunit and a β subunit. It may also comprise an γ subunit. In a particular embodiment of the invention, the α2-δ subunit, when present, has at least 70%, advantageously at least 80%, preferably at least 90%, more preferably at least 95% and in particular at least 98%, e. g. at least 99%, amino acid sequence identity with the sequence SEQ ID NO:2. In a further particular embodiment of the invention, the β subunit, when present, has at least 70%, advantageously at least 80%, preferably at least 90%, more preferably at least 95% and in particular at least 98%, e. g. at least 99%, amino acid sequence identity with the sequence SEQ ID NO:3.

Further characteristic features of P/Q type voltage-gated presynaptic calcium channels are described in Catterall W A, Perez-Reyes E, Snutch T P, Striessnig J. International Union of Pharmacology. XLVIII. Nomenclature and structure-function relationships of voltage-gated calcium channels. Pharmacol Rev. 57: 411-25 (2005), which is herein incorporated by reference in its entirety.

The term "Aβ globulomer" here refers to any Aβ(X-Y) globulomer which is a soluble, globular, non-covalent association of Aβ(X-Y) peptides, wherein an Aβ(X-Y) peptide is a fragment of the amyloid β protein from amino acid residue X to amino acid residue Y inclusive, possessing homogeneity and distinct physical characteristics. According to one aspect, Aβ(X-Y) globulomers are stable, non-fibrillar, oligomeric assemblies of Aβ(X-Y) peptides which are obtainable by incubation with anionic detergents. In contrast to monomer and fibrils, these globulomers are characterized by defined assembly numbers of subunits (e.g. early assembly forms, n=4-6, "oligomers A", and late assembly forms, n=12-14, "oligomers B", as described in WO2004/067561). The globulomers have a 3-dimensional globular type structure ("molten globule", see Barghorn et al., 2005, J Neurochem, 95, 834-847). They may be further characterized by one or more of the following features:

cleavability of N-terminal amino acids X-23 with promiscuous proteases (such as thermolysin or endoproteinase GluC) yielding truncated forms of globulomers;

non-accessibility of C-terminal amino acids 24-Y with promiscuous proteases and antibodies;

truncated forms of these globulomers maintain the 3-dimensional core structure of said globulomers with a better accessibility of the core epitope Aβ(20-Y) in its globulomer conformation.

According to the invention and in particular for the purpose of assessing the binding affinities of the antibodies of the present invention, the term "Aβ(X-Y) globulomer" here refers in particular to a product which is obtainable by a process as described in WO 2004/067561, which is incorporated herein by reference.

Said process comprises unfolding a natural, recombinant or synthetic Aβ(X-Y) peptide or a derivative thereof; exposing the at least partially unfolded Aβ(X-Y) peptide or derivative thereof to a detergent, reducing the detergent action and continuing incubation.

For the purpose of unfolding the peptide, hydrogen bond-breaking agents such as, for example, hexafluoroisopropanol (HFIP) may be allowed to act on the protein. Times of action of a few minutes, for example about 10 to 60 minutes, are sufficient when the temperature of action is from about 20 to 50° C. and in particular about 35 to 40° C. Subsequent dissolution of the residue evaporated to dryness, preferably in concentrated form, in suitable organic solvents miscible with aqueous buffers, such as, for example, dimethyl sulfoxide (DMSO), results in a suspension of the at least partially unfolded peptide or derivative thereof, which can be used subsequently. If required, the stock suspension may be stored at low temperature, for example at about −20° C., for an interim period.

Alternatively, the peptide or the derivative thereof may be taken up in slightly acidic, preferably aqueous, solution, for example an about 10 mM aqueous HCl solution. After an incubation time of usually a few minutes, insoluble components are removed by centrifugation. A few minutes at 10000 g is expedient. These method steps are preferably carried out at room temperature, i.e. a temperature in the range from 20 to 30° C. The supernatant obtained after centrifugation contains the Aβ(X-Y) peptide or the derivative thereof and may be stored at low temperature, for example at about −20° C., for an interim period.

The following exposure to a detergent relates to the oligomerization of the peptide or the derivative thereof to give an intermediate type of oligomers (in WO 2004/067561 referred to as oligomers A). For this purpose, a detergent is allowed to act on the at least partially unfolded peptide or derivative thereof until sufficient intermediate oligomer has been produced.

Preference is given to using ionic detergents, in particular anionic detergents.

According to a particular embodiment, a detergent of the formula (I):

R—X, is used, in which the radical R is unbranched or branched alkyl having from 6 to 20 and preferably 10 to 14 carbon atoms or unbranched or branched alkenyl having from 6 to 20 and preferably 10 to 14 carbon atoms, the radical X is an acidic group or salt thereof, with X being preferably selected from among —COO$^-$M$^+$, —SO$_3$$^-$M$^+$, and especially —OSO$_3$$^-$M$^+$ and M$^+$ is a hydrogen cation or an inorganic or organic cation preferably selected from alkali metal and alkaline earth metal cations and ammonium cations.

Advantageous are detergents of the formula (I), in which R is unbranched alkyl of which alk-1-yl radicals must be mentioned in particular. Particular preference is given to sodium dodecyl sulfate (SDS). Lauric acid and oleic acid can also be used advantageously. The sodium salt of the detergent lauroylsarcosin (also known as sarkosyl NL-30 or Gardol®) is also particularly advantageous.

The time of detergent action in particular depends on whether—and if yes, to what extent—the peptide or the derivative thereof subjected to oligomerization has unfolded. If, according to the unfolding step, the peptide or derivative thereof has been treated beforehand with a hydrogen bond-breaking agent, i.e. in particular with hexafluoroisopropanol, times of action in the range of a few hours, advantageously from about 1 to 20 and in particular from about 2 to 10 hours, are sufficient when the temperature of action is about 20 to 50° C. and in particular about 35 to 40° C. If a less unfolded or an essentially not unfolded peptide or derivative thereof is the starting point, correspondingly longer times of action are expedient. If the peptide or the derivative thereof has been pretreated, for example, according to the procedure indicated above as an alternative to the HFIP treatment or said peptide or derivative thereof is directly subjected to oligomerization, times of action in the range from about 5 to 30 hours and in particular from about 10 to 20 hours are sufficient when the temperature of action is about 20 to 50° C. and in particular about 35 to 40° C. After incubation, insoluble components are advantageously removed by centrifugation. A few minutes at 10000 g is expedient.

The detergent concentration to be chosen depends on the detergent used. If SDS is used, a concentration in the range from 0.01 to 1% by weight, preferably from 0.05 to 0.5% by weight, for example of about 0.2% by weight, proves expedient. If lauric acid or oleic acid are used, somewhat higher concentrations are expedient, for example in a range from 0.05 to 2% by weight, preferably from 0.1 to 0.5% by weight, for example of about 0.5% by weight.

The detergent action should take place at a salt concentration approximately in the physiological range. Thus, in particular NaCl concentrations in the range from 50 to 500 mM, preferably from 100 to 200 mM and particularly at about 140 mM are expedient.

The subsequent reduction of the detergent action and continuation of incubation relates to a further oligomerization to give the Aβ(X-Y) globulomer of the invention (in WO 2004/067561 referred to as oligomers B). Since the composition obtained from the preceding step regularly contains detergent and a salt concentration in the physiological range it is then expedient to reduce detergent action and, preferably, also the salt concentration. This may be carried out by reducing the concentration of detergent and salt, for example, by diluting, expediently with water or a buffer of lower salt concentration, for example Tris-HCl, pH 7.3. Dilution factors in the range from about 2 to 10, advantageously in the range from about 3 to 8 and in particular of about 4, have proved suitable. The reduction in detergent action may also be achieved by adding substances which can neutralize said detergent action. Examples of these include substances capable of complexing the detergents, like substances capable of stabilizing cells in the course of purification and extraction measures, for example particular EO/PO block copolymers, in particular the block copolymer under the trade name Pluronic® F 68. Alkoxylated and, in particular, ethoxylated alkyl phenols such as the ethoxylated t-octylphenols of the Triton® X series, in particular Triton® X100, 3-(3-cholamidopropyl-dimethylammonio)-1-propanesulfonate (CHAPS®) or alkoxylated and, in particular, ethoxylated sorbitan fatty esters such as those of the Tween® series, in particular Tween® 20, in concentration ranges around or above the particular critical micelle concentration, may be equally used.

Subsequently, the solution is incubated until sufficient Aβ(X-Y) globulomer of the invention has been produced. Times of action in the range of several hours, preferably in the range from about 10 to 30 hours and in particular in the range from about 15 to 25 hours, are sufficient when the temperature of action is about 20 to 50° C. and in particular about 35 to 40° C. The solution may then be concentrated and possible residues may be removed by centrifugation. Here too, a few minutes at 10000 g proves expedient. The supernatant obtained after centrifugation contains an Aβ(X-Y) globulomer of the invention.

An Aβ(X-Y) globulomer of the invention can be finally recovered in a manner known per se, e. g. by ultrafiltration, dialysis, precipitation or centrifugation.

It is further preferred if electrophoretic separation of the Aβ(X-Y) globulomers under denaturing conditions, e. g. by SDS-PAGE, produces a double band (e. g. with an apparent molecular weight of 38/48 kDa for Aβ(1-42)), and especially preferred if upon glutardialdehyde treatment of the globulomers before separation these two bands are merged into one. It is also preferred if size exclusion chromatography of the globulomers results in a single peak (e. g. corresponding to a molecular weight of approximately 100 kDa for Aβ(1-42) globulomer or of approximately 60 kDa for glutardialdehyde cross-linked Aβ(1-42) globulomer), respectively.

For the purposes of the present invention, an Aβ globulomer is in particular the Aβ(1-42) globulomer as described in reference example 2 herein.

As used herein, an "inhibitor of Aβ-P/Q interaction" is any substance that effectively reduces an Aβ-P/Q interaction and thereby the inhibition of the activity of the P/Q type voltage-gated presynaptic calcium channel by an Aβ globulomer. Preferably, the inhibitor of the Aβ-P/Q interaction exerts no significant effect on activity of the P/Q type voltage-gated presynaptic calcium channel in the absence of Aβ globulomer.

The expression "effectively reduces" is used herein to denote any reduction causally connected with the presence of said inhibitor, irrespective of the individual mode of action.

In a particular embodiment of the invention, an inhibitor of the Aβ-P/Q interaction is a substance that effectively reduces the mutual affinity of Aβ globulomer and the P/Q type voltage-gated presynaptic calcium channel below its normal value, wherein the "normal value" is understood to be the value of [Aβ globulomer-P/Q complex]/([Aβ globulomer]+[P/Q]) in the absence of the inhibitor but under otherwise identical circumstances, which may refer to either molecule being in situ or isolated.

Herein, the term "in situ" is understood to refer to any molecule or structure being in its natural molecular environment as found in an intact cell and/or organism, which may be either healthy or diseased, e. g. as obtainable by taking samples ex vivo, and "isolated" to refer to any molecule or structure essentially separated from at least one of, preferably essentially all of the elements forming its natural environment as found in an intact cell and/or organism, e. g. as obtainable by recombinant expression. Preferably, "isolated" is in vitro.

It is noted that in vivo the P/Q type voltage-gated presynaptic calcium channel may interact with, i.e. bind to, Aβ forms other than the Aβ globulomers described herein. These Aβ forms may or may not be oligomeric or globulomeric. Thus, the ligands with which the P/Q type voltage-gated presynaptic calcium channel interacts include any Aβ form that comprises the globulomer epitope with which Aβ globulomers described herein bind to the P/Q type voltage-gated presynaptic calcium channel. Such Aβ forms include truncated and non-truncated Aβ(X-Y) forms (with X and Y being defined as above), such as Aβ(20-42), Aβ(20-40), Aβ(12-42), Aβ(12-40), Aβ(1-40) forms, provided that said forms comprise the globulomer epitope.

Inhibitors of the Aβ-P/Q interaction may be identified among compounds known per se by screening for their capacity to prevent and/or reverse the blockade of the P/Q type voltage-gated presynaptic calcium channel caused by Aβ globulomer, preferably by screening using a method comprising determining the effect of a candidate compound on the opening state of the P/Q type voltage-gated presynaptic calcium channel in the presence of Aβ globulomer, most conveniently by determining the effect of said compound on the $Ca^{++}$ flux through the P/Q type voltage-gated presynaptic calcium channel in the presence of Aβ globulomer. Suitable methods for determining transmembrane ion fluxes such as $Ca^{++}$ fluxes through the P/Q type voltage-gated presynaptic calcium channel have been described in the art (Sakmann B and Neher E. Single-Channel Recording. Springer US, 97 A.D.).

A method for determining whether any candidate compound is an inhibitor of the Aβ-P/Q interaction comprises the steps of (I) providing the P/Q type voltage-gated presynaptic calcium channel;

(II) additionally providing Aβ(1-42) globulomer and bringing it into contact with the P/Q type voltage-gated presynaptic calcium channel; and (III) determining $Ca^{++}$ fluxes through said P/Q type voltage-gated presynaptic calcium channel in the presence and in the absence of the candidate compound;

wherein an increase of the $Ca^{++}$ flux through the P/Q type voltage-gated presynaptic calcium channel in the presence relative to the situation in the absence of the candidate compound is indicative of an the candidate compound being an inhibitor of the Aβ-P/Q interaction.

The P/Q type voltage-gated presynaptic calcium channel is known per se (see, e. g., WO98/13490; Qian J and Noebels J L. *J Neurosci* 21: 3721-3728, 2001; Yan Z, et al., 2002, supra). WO98/13490 in particular discloses the cDNA sequence for the human P/Q type voltage-gated presynaptic calcium channel, encoding a protein of 2261 amino acids. Methods for expressing a protein from a cDNA in vertebrate cells are well-documented in the art; e. g. WO96/39512 discloses a process for generating cell lines expressing voltage-gated calcium channels. It is thus within the ken of the skilled person to provide the P/Q type voltage-gated presynaptic calcium channel.

Expediently, the P/Q type voltage-gated presynaptic calcium channel is provided on a living cell, which cell may be either in its natural environment (in situ) or separated therefrom (ex vivo). In a particular embodiment, the cell to be used in the screening method is of a type that naturally expresses the P/Q type voltage-gated presynaptic calcium channel, e. g. a neuronal cell such as a hippocampal neuronal cell. In another embodiment, the cell to be used in the screening method expresses the P/Q type voltage-gated presynaptic calcium channel as a foreign gene. In this embodiment, it is preferred that the cell naturally does not express any other voltage-gated presynaptic calcium channels, e. g. a non-neural cell, e. g. a *Xenopus oocyte*. Conveniently, expression of the P/Q type voltage-gated presynaptic calcium channel in the cells is verified using standard methology, e. g. by Northern blotting, RT-PCR, Western blotting, cytometry, binding of P/Q-specific ligands such as w-agatoxin, or pharmacological characterization, i. e. reduction of calcium current after agatoxin application.

In a further particular embodiment, said living cell further comprises an agent for the in situ detection of calcium ion levels (i. e. a calcium sensor agent), e. g. a protein with a calcium-dependent luminescence or fluorescence, such as aequorin or cameleon (Putney P W. *Calcium Signaling*. CRC Press Inc, 2005). Such calcium sensor agents are well-known to the skilled person, and essentially any of them may be used in the present invention. Without wishing to be bound by theory, it is believed that in suitable agents the conformation of the molecule changes in a manner that depends on the local concentration of $Ca^{++}$, thereby hampering or facilitating physical processes, such as inter- or intramolecular energy transfers, that may be detected and correlated with calcium channel function by the experimentator. Thus, the fluorescence or luminesence of said calcium sensor agents is indicative of the local (e. g. intracellular) calcium levels.

Hence, when the only functional calcium channel of the cell is the P/Q type voltage-gated presynaptic calcium channel, increases in intracellular calcium concentrations $$\left(\frac{d[Ca^{++}]}{dt} > 0\right)$$

indicate calcium fluxes through the P/Q type voltage-gated presynaptic calcium channel. Therefore, a raise in said increase $$\left(\frac{d[Ca^{++}]_c}{dt} > \frac{d[Ca^{++}]_0}{dt}\right),$$

where $[Ca^{++}]_C$ is the intracellular calcium concentration in the cell in the presence and $[Ca^{++}]_0$ in the absence of the candidate compound) in the presence of Aβ globulomer indicates that a candidate substance is an inhibitor of the Aβ-P/Q interaction and thus potentially useful for the treatment of amyloidoses, as described above.

Suitable methods for the direct determination of ion fluxes, such as the voltage-clamp method, are likewise known in the art (Sakmann B and Neher E. *Single-Channel Recording* Springer US, 97 A.D.). Essentially, conductive microconnections with the inside and the outside of the cell membrane are established, and the electrical reactivity of the system under different conditions is observed.

The standard method employed here for all determinations of $Ca^{++}$ currents is a patch-clamp method using 120 mM NMG.Cl, 10 mM TEA.Cl, 14 mM creatine phosphate, 6 mM $MgCl_2$, 1 mM $CaCl_2$ 10 mM NMG.HEPES, 5 mM $Tris_2$.ATP and 11 $NMG_2$.EGTA as internal, and 30 mM $BaCl_2$, 100 mM NMG.Cl, 10 mM NMG.HEPES and 15 mM glucose as external solution, both adjusted to a pH of about 7.2-7.3, for measuring stably transfected BHK (Baby Hamster Kidney) cells expressing the α1 component together with the α2δ and βIB components of the P/Q type voltage-gated presynaptic calcium channel.

Further details of said standard method have been described by Zafir Buraei et al., Roscovitine differentially affects CaV2 and Kv channels by binding to the open state, Neuropharmacology (2006), doi:10.1016/j.neuropharm.2006.10.006 (corresponds to issue 52, 2007, pages 883-894), which is herein incorporated by reference in its entirety.

Preferably, prior to the measurement irrelevant ion channels are blocked using inhibitors specific for said irrelevant channels ("pharmacological isolation" of the relevant channel or channels), eliminating the dependencies of the electrical status of the membrane on all channels except the one or ones of interest (i. e. the P/Q channel). An inhibitor of the Aβ-P/Q interaction and hence an agent suitable for the treatment of amyloidoses according to the present invention, as mentioned above, will thus be identified as an enhancer of $Ca^{++}$ flux observed in the presence of Aβ when only the P/Q type voltage-gated presynaptic calcium channel is expressed, or when all other calcium channels are blocked.

As all these methods for the determination of $Ca^{++}$ fluxes are essentially quantitative, they are also suitable for the identification of an inhibitor of the Aβ-P/Q interaction with any particularly desired strength of inhibitory effect on the Aβ-P/Q interaction, wherein the strength of the inhibitory effect is the increase in calcium influx induced by the inhibitor in the presence of Aβ globulomer under the conditions selected.

Thus, an agent for the treatment of amyloidoses such as Alzheimer's disease can be identified by determining the effect of said agent on a cell comprising at least the P/Q type voltage-gated presynaptic calcium channel, in particular the effect on the $Ca^{++}$ flux through the P/Q type voltage-gated presynaptic calcium channel of said living cell, in the presence of Aβ globulomer, wherein an inhibitor of the Aβ-P/Q interaction is potentially a suitable agent for the treatment of amyloidoses according to the present invention.

In a particular embodiment of the invention, the inhibitor of the Aβ-P/Q interaction binds to the P/Q type voltage-gated presynaptic calcium channel, preferably with an affinity of $K_D \leq 1$ μM, more preferably $K_D \leq 100$ nM, still more preferably $K_D \leq 10$ nM and most preferably $K_D \leq 1$ nM, in particular $K_D \leq 100$ pM.

In the context of the present invention, the term "bind" is used generically to denote any immediate physical contact between to molecules, which may be covalent or non-covalent, thus including covalent bonds, hydrogen bridges, ionic interactions, hydrophobic associations, van der Waals forces, etc. It will thus be understood that the term also extends to the temporary association of a first molecule with a catalytically active second molecule, wherein said second molecule performs a modification or modifications on said first molecule which, and consequently whose effects, outlast the actual contact between said first and said second molecule, e. g. generation or removal of covalent bonds.

Suitable methods for determining physical contact between molecules are generally well-known to the person skilled the art and comprise, without being limited to, determining radiation-free energy transfer, radiolabelling of ligands and co-immunoprecipitation.

Alternatively, the inhibitor of the Aβ-P/Q interaction binds to Aβ globulomer, preferably with an affinity of $K_D \leq 1$ µM, more preferably $K_D \leq 100$ nM, still more preferably $K_D \leq 10$ nM and most preferably $K_D \leq 1$ nM, in particular $K_D \leq 100$ pM.

The metabolism of APP and its products such as Aβ is complex and not yet fully understood. Therefore, it is preferred that the inhibitor of the Aβ-P/Q interaction specifically binds to Aβ globulomer, the term "bind specifically to Aβ globulomer" herein being used to denote that the inhibitor shows no significant amount of binding to any other elements of the APP metabolism and in particular no significant amount of binding to the APP protein itself.

The skilled person will understand that an "inhibitor of the Aβ-P/Q interaction" as defined in the present invention may thus bind to the P/Q type voltage-gated presynaptic calcium channel, thereby preventing it, either competitively or by allosteric influences, from participating in the Aβ-P/Q interaction; or to Aβ, in particular to Aβ globulomer, thereby preventing it, either competitively or by allosteric influences, from participating in the Aβ-P/Q interaction.

As used herein, the term "competitive" is used to denote all changes directly influencing a region of intermolecular interaction, which may be covalent or non-covalent, whereas "allosteric" is used to denote all changes not directly influencing a region of intermolecular interaction, which changes may be covalent or non-covalent.

In a preferred embodiment of the invention, the inhibitor reduces the Aβ-P/Q interaction to less than one half of its normal value, preferably to less than one third of its normal value, e. g. to less than 10% of its normal value, wherein the value of the interaction is defined as the difference in activity of the P/Q type voltage-gated presynaptic calcium channel in the presence and in the absence of Aβ globulomer.

According to a further aspect, the invention thus also discloses a pharmaceutical agent or composition for inhibiting the Aβ-P/Q interaction, and its use in the treatment of an amyloidosis such as Alzheimer's disease.

In a particular embodiment of the invention, said agent is an antibody, preferably an anti-P/Q type voltage-gated presynaptic calcium channel antibody, or a fragment or derivative thereof.

As used herein, the anti-P/Q type voltage-gated presynaptic calcium channel antibodies for use in the present invention include polyclonal antibodies (antisera), monoclonal antibodies, recombinant antibodies (including bispecific antibodies), and antigen-binding fragments thereof, e. g. Fab fragments, F(ab')$_2$ fragment, and single chain Fv fragments, Fab' fragments, Fv fragments, and disulfide linked Fv fragments, as well as derivatives thereof. Basically, any antibody, fragment or derivative that binds to the P/Q type voltage-gated presynaptic calcium channel may be used in the present invention. The antibody may be of any class or subclass, e. g. IgM, IgD, IgG, IgA or IgE, and be derived from any commonly used species, e. g. a mammal such as rat, mouse, rabbit, sheep, goat, horse or donkey. Procedures for obtaining suitable antibodies, as well as for fragmenting or derivatizing them, have been described extensively in the art, and are well-known to the skilled artisan. Expediently, a suitable host animal is immunized with the P/Q type voltage-gated presynaptic calcium channel or a fragment or derivative thereof, and the antibodies are isolated in a manner known per se, e. g. using standard hybridoma techniques.

Preferably, the antibody or fragment or derivative thereof does not comprise the portions that are required for induction of biological, in particular immunological, responses; expediently, the Fc part is missing or mutated so not to direct immunological reactions against the P/Q type voltage-gated presynaptic calcium channel. More preferably, the antibody or fragment or derivative thereof is univalent and does not cause cross-linking of the receptors after binding.

For instance, an affinity purified goat polyclonal antibody raised against a peptide mapping near the C-terminus of the α1A subunit of the P/Q type voltage-gated presynaptic calcium channel of human origin is commercially available from Santa Cruz Biotechnology, Inc.

In another particular embodiment of the invention, said agent is an aptamer capable of selectively binding either to the P/Q type voltage-gated presynaptic calcium channel or to Aβ globulomer, the term "aptamer" being used herein to refer to any small molecule that is capable of specific, non-covalent binding to its target, preferably to a peptide, DNA or RNA sequence, more preferably to a peptide, DNA or RNA sequence of about 3 to 100 monomers, in particular of about 5 to 30 monomers, most preferably to a peptide of about 5 to 30 amino acids, which may at one end or both ends be attached to a larger molecule, preferably a larger molecule mediating biochemical functions, more preferably a larger molecule inducing inactivation and/or degradation, most preferably ubiquitin, or preferably a larger molecule facilitating destruction, more preferably an enzyme or a fluorescent protein. Methods for obtaining such aptamers are known per se.

In another particular embodiment of the invention, said agent is a low molecular weight compound, the term "low molecular weight compound" being used herein to refer to a compound with a molecular weight of less than 2000 Da, preferably less than 1000 Da and more preferably less than 500 Da.

In a preferred embodiment of the invention, the inhibitor of the Aβ-P/Q interaction does not exert any inhibitory effect on the P/Q type voltage-gated presynaptic calcium channel when bound.

In a preferred embodiment of the invention, the inhibitor of the Aβ-P/Q interaction does not exert any activating effect on the P/Q type voltage-gated presynaptic calcium channel when bound in the absence of Aβ globulomer.

As used herein, the term "administering" is used to denote delivering an agent to a subject, especially a human subject. Basically, any route of administration known in the art, e. g. buccal, sublingual, oral, rectal, transdermal, subcutaneous, intramuscular, intravenous, intraarterial, intraperitoneal, intrathecal, intralumbaginal or intradural, and any dosage regimen, e. g. as bolus or as continuous supply, may be employed to administer the agent.

The agent may be delivered simply as such or, preferably, in combination with any of a wide range of carriers and excipients, as known in the art, thereby forming a pharmaceutical composition. If desired, a convenient drug targeting and/or delivery system may be used. Expediently, the agent and at least one carrier are combined into a dosage form as known per se to those skilled in the art, e. g. into a controlled or sustained release system. Basically, any carrier and/or excipient compatible with the agent and any kind of dosage form may be used in the methods of the present invention. Suitable compounds and methods are known in the art.

Thus, the present invention will be understood to also relate to the methods and uses relating to the manufacture of pharmaceutical compositions useful in the treatment of amyloidoses. In particular, amyloidoses according to the present invention comprise Alzheimer's disease and Down's syndrome.

In a particular embodiment of the invention, the treatment is a rehabilitating and/or symptomatic treatment.

A "rehabilitating" treatment, as used herein, is, in particular, for providing a benefit with regard to the patient's overall quality of life.

As used herein, a "benefit" is any amelioration in relevant clinical parameters or decrease in subjective suffering of the subject amenable to scoring that can be causally connected to a particular therapeutic measure. Expediently, the benefit is measured by comparing the relevant clinical parameters or the subjective suffering of the subject at a time point before treatment and at least one time point during or after treatment, and expressed in terms of a gain in quality-adjusted life years or disability-adjusted life years (QALYs and DALYs).

The concept of "quality-adjusted life years" and "disability-adjusted life years" is used extensively in the art to evaluate agents and methods, in particular in the context of those diseases where morbidity and disability are medically and socially more of a concern than mortality is, such as dementing diseases. Essentially, each year the life time following treatment is multiplied with an index factor which ranges from 1.0 to indicate perfect quality of life, or zero disability, to 0.0 to indicate death, or complete disability, and the sum of these products is compared to the value obtainable without treatment. Suitable definitions and methods for determining gains and losses in QALYs and DALYs in particular with regard to dementing diseases such as amyloidoses, have been described in the art.

Thus, a benefit is preferably an increase in the aforementioned index factor. In a particular embodiment of the invention, the treatment is hence for providing a benefit to a subject suffering from an amyloidosis.

A "symptomatic" treatment, as used herein, is, in particular, a treatment directed to the abatement or relief of the symptoms of the disease.

In a particular embodiment the present invention relates to a method for the restoration of Aβ-impaired synaptic function and/or plasticity, in particular long-term potentiation, in the subject.

In a further particular embodiment the present invention relates to a method for the restoration of cognitive abilities, memory function and/or performance of activities of daily life (ADL) capacity in the subject.

As used herein, the terms "cognitive abilities", "synaptic function", "long-term potentiation" and "memory function" have the meanings as are widely known and used in the art, and their quantifiable values are considered as "normal" or "restored" when within the range which is commonly to be expected, e. g. based on long-standing medical practice, appropriate clinical trials and/or biochemical analysis, for the individual subject under consideration when compared to a representative population of other subjects whose essential parameters otherwise agree with those of said subject under consideration (peers of said subject). In particular, memory function is considered normal in a subject when said subject upon investigation by suitable means, e. g. short- and/or long-time learning tests, shows no significant deficiencies with regard to memory in function in comparison to a control group matched in species, age, gender and optionally other factors acknowledged as relevant to mental health, which are well-known to those skilled in the art, e. g. blood cholesterol levels, and/or psycho-social factors, e. g. educational and/or occupational background.

As used herein, the term "activities of daily living", abbreviated "ADL", is used to denote the essential manual and mental tasks and chores of everyday life, in particular those involving domains of language (impairment thereof being known as "aphasia"), skilled movements (impairment being known as "apraxia" and potentially leading to total loss of control over the body in the final stages of the disease), and the use of cognitive abilities such as recognition (impairment being known as "agnosia", often accompanied by disorientation and disinhibition, and sometimes also with behavioural changes), and higher-level intellectual functions (such as decision-making and planning). These capacities can be assessed e. g. using questionnaire-based tests well-known in the art, such as the Hodgkinson test (aka. "mini-mental state examination" or MMSE, comprising the recital of basic facts of everyday life) and the Folstein test (aka. "abbreviated mental test score" or AMTS, comprising remembering the time and place of the test, repeating lists of words, arithmetic, language use and comprehension, and copying a simple drawing) for basic mental functions and the John Hopkins Functioning Inventory (aka. JHFI) for basically motoric or movement-related abilities such as sitting, standing, walking, eating, washing, dressing etc.

The skilled person will be aware that in amyloidoses such as Alzheimer's disease the impairment of ADL capacity is dominated, in particular in its early and middle stages, by impairment of the intellectual rather than of motoric or sensory functions, and that even the latter, when found, is due to central rather than peripheral disturbances (e. g. "forgetting how to walk" rather than genuine organic paralysis).

In another aspect the present invention further relates to a method for identifying an inhibitor of the Aβ-P/Q interaction, comprising determining whether a candidate compound exerts an inhibitory effect on the Aβ-P/Q interaction, as disclosed above.

In a particular embodiment of the invention, the method comprises determining the physical contact between Aβ globulomer and the P/Q type voltage-gated presynaptic calcium channel, as disclosed above.

The invention will now be further illustrated by way of reference to the following non-limiting examples and figures. Unless stated otherwise, the terms "A-Beta", "Aβ$_{1-42}$", "Aβ", "aβ", "glob" all denote the Aβ(1-42) globulomer described in reference example 2. "Kontrolle" means "control".

The SeeBlue Prestined Marker is represented with M. A represents the 80,000 g membrane-protein fraction, and B was used for the 150,000 g residual membrane protein fraction. The gels were loaded in the following order:

A1: 5 μg of membrane proteins before affinity chromatography
A2: Unbound proteins after affinity chromatography
A3: PBS/0.5% SDS elution
B1: 5 μg of residual membrane proteins before affinity chromatography
B2: Unbound proteins after affinity chromatography
B3: PBS/0.5% SDS elution FIG. 19: Spontaneous synaptic activity is reversibly suppressed by Aβ(1-42) globulomer. Original recording of spontaneously occurring synaptic currents in a cultured hippocampal neuron before (top), during (middle) and after (bottom) application of Aβ(1-42) globulomer.

Figure 20:
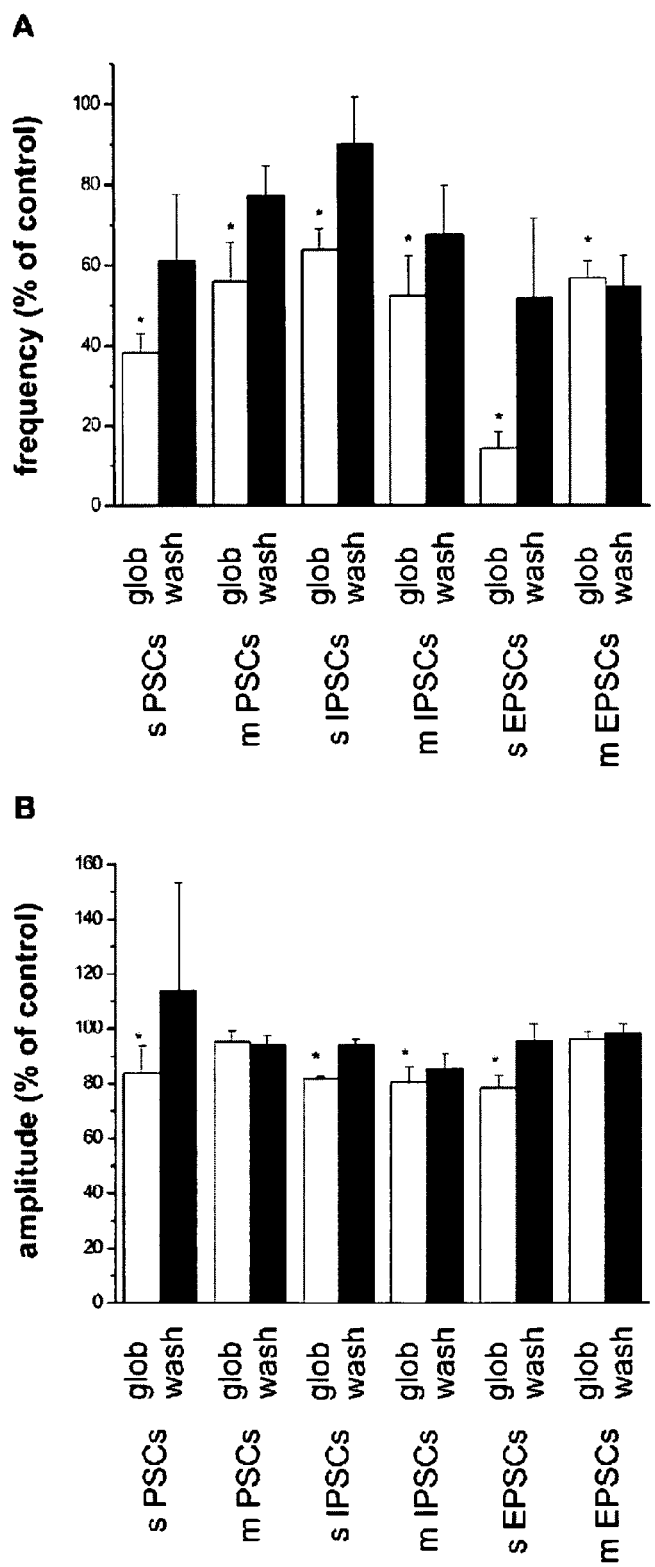

FIG. 20: Effects of Aβ(1-42) globulomer on different types of synaptic currents in cultured hippocampal neurons. White bars: effect of Aβ(1-42) globulomer; black bars: washout for at least 10 min. A: Reduction of event frequency as percentage of previously recorded control currents (1.0). B: Effects of Aβ(1-42) globulomer on median amplitude of the respective currents. sPSCs: spontaneously occurring pharmacologically naive postsynaptic currents; mPSCs: pharmacologically naive miniature postsynaptic currents recorded in the presence of TTX; mIPSCs: miniature inhibitory postsynaptic currents; sEPSCs: spontaneously occurring excitatory postsynaptic currents; mEPSCs: miniature excitatory postsynaptic currents.

Figure 21:
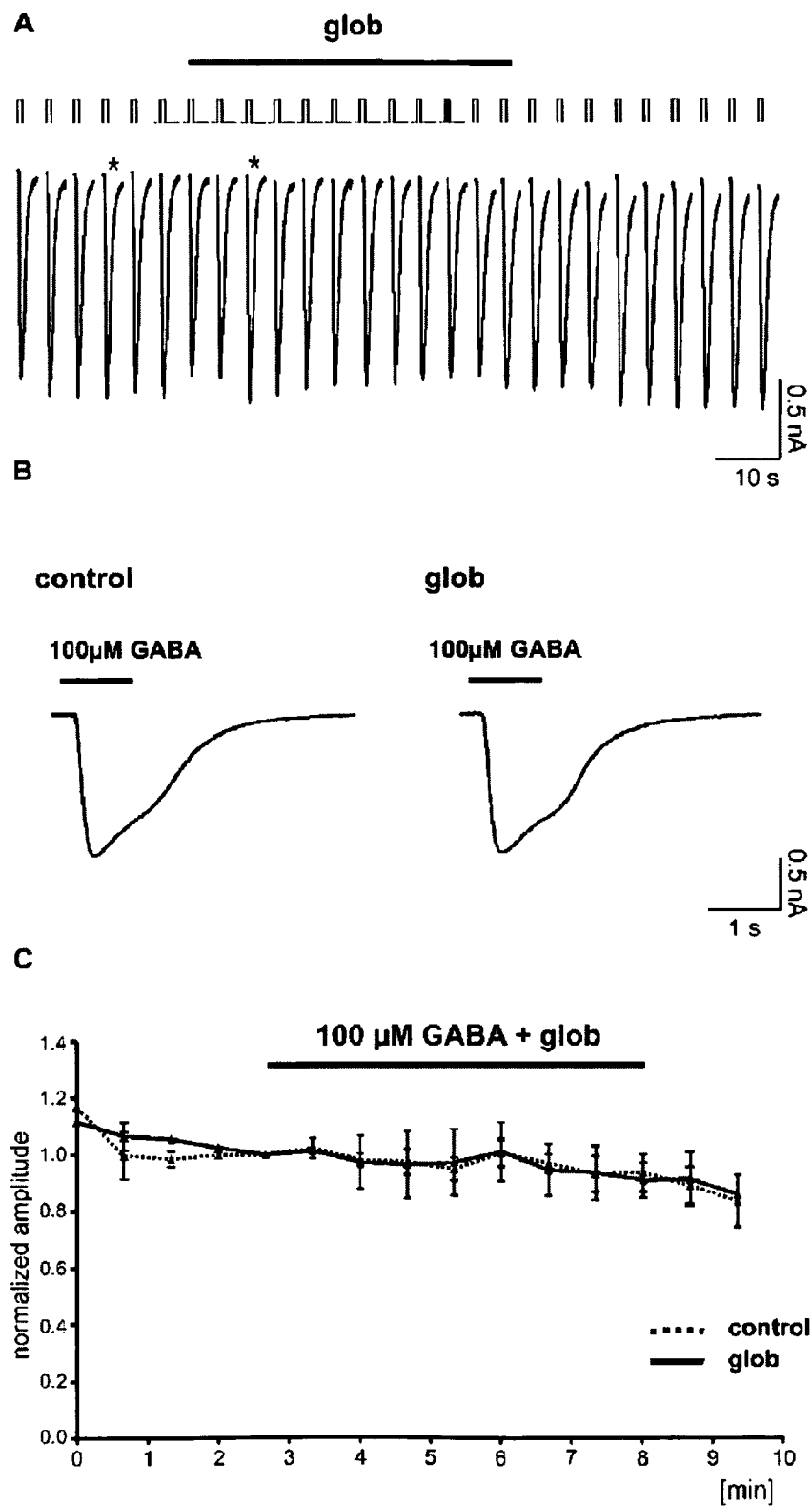

FIG. 21: Stability of $GABA_A$ receptor-mediated currents towards Aβ(1-42) globulomer. A: Repetitive application of 100 μM GABA to a cultured hippocampal neuron yields stable inward current before, during, and after application of the oligomer. B: Enlarged view of current traces marked with * in A. Note the stability of response in the absence (left) and presence (right) of Aβ(1-42) globulomer. C: Time course of GABA-induced currents from 5 cells recorded in control solution (dashed line) and from 3 neurons where Aβ(1-42) globulomer was applied (continuous line, time of application indicated by bar). Amplitudes normalized to the last GABA-induced current before application of Aβ(1-42) globulomer.

Figure 22:
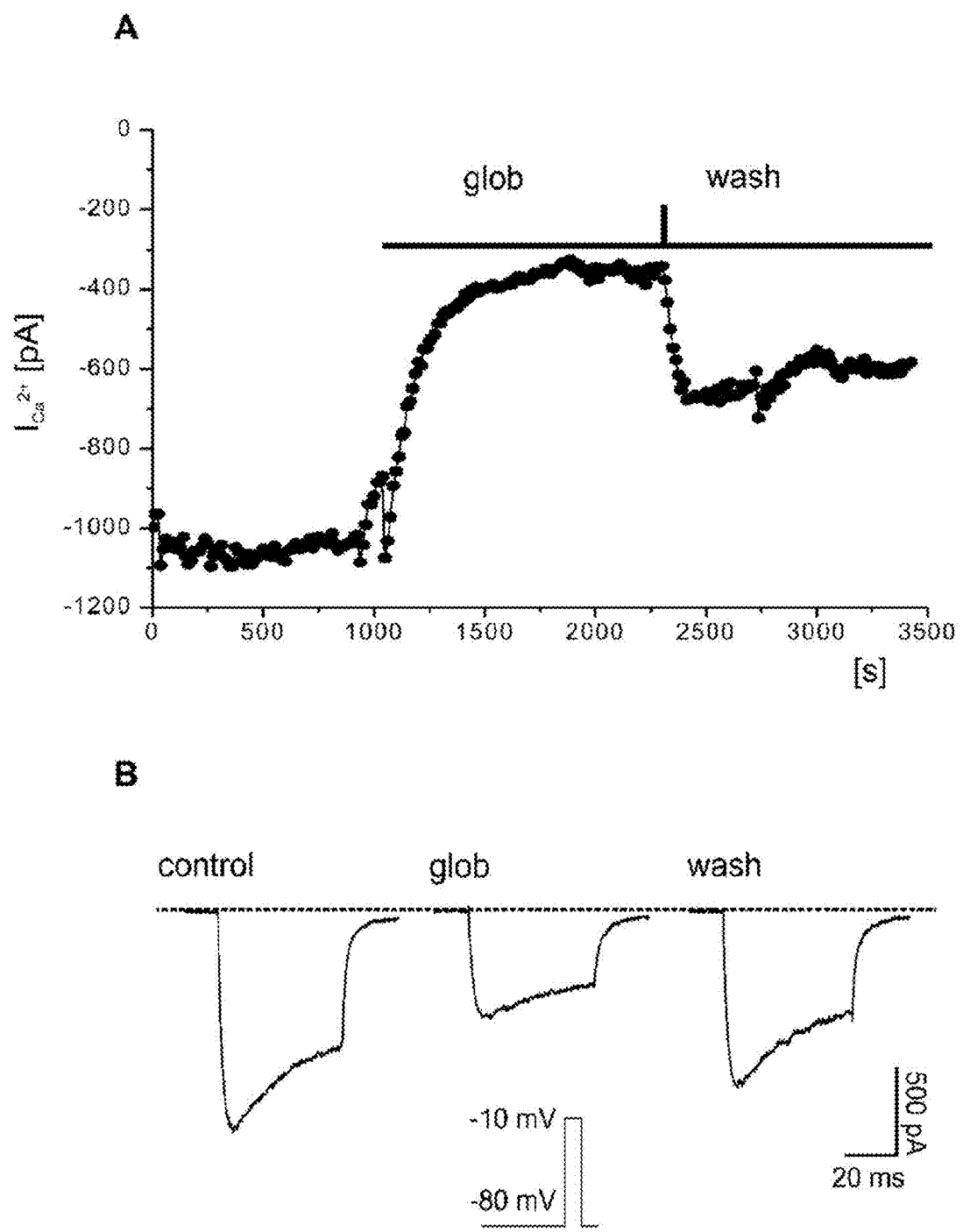

FIG. 22 Suppression of P/Q-type calcium currents by Aβ(1-42) globulomer. A: Time course of current amplitudes upon application of globulomer. Currents were elicited by voltage steps to −10 mV. B: Example traces of P/Q-type currents before, during and after globulomer.

Figure 23:
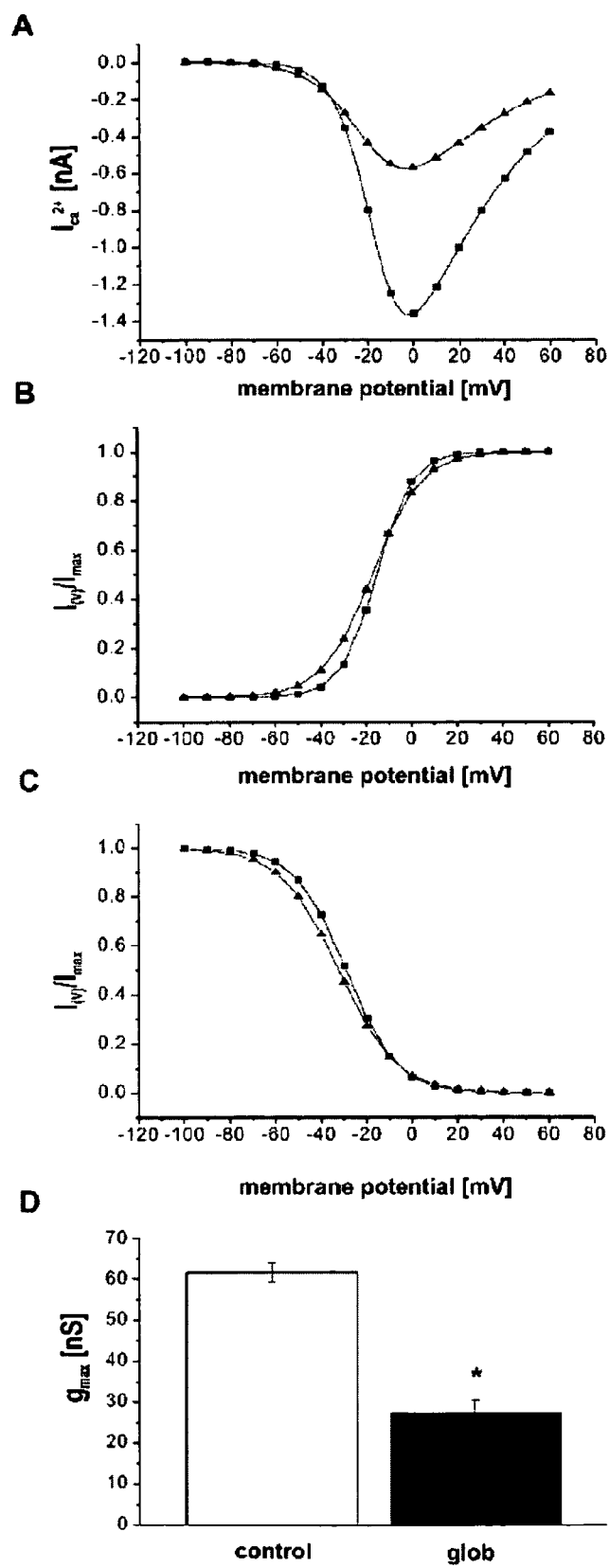

FIG. 23 Steady-state activation and inactivation parameters of P/Q currents. A: Current/voltage relationship before globulomer (squares) and during Aβ(1-42)(triangles). A reduction of the current amplitudes over the entire voltage-range, were the current could be activated, was observed following application of the globulomer. B & C: No difference in steady-state activation (B) and inactivation curves (C) for P/Q channel-mediated barium currents in the absence and presence of Aβ(1-42) globulomer. D: A significant decrease in maximal conductance ($g_{max}$) of the P/Q channels was induced by Aβ(1-42) globulomer.

Figure 24:
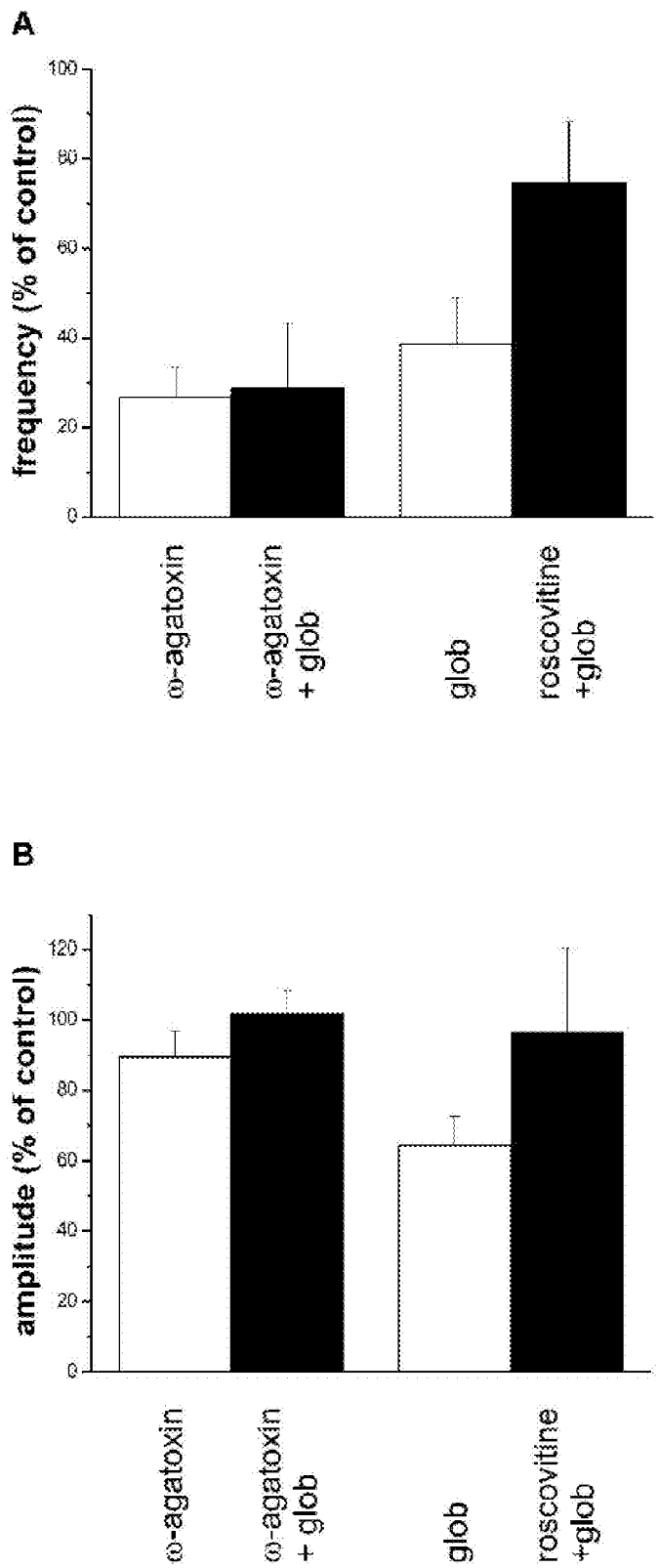

FIG. 24 Pharmacological modulation of the effect of Aβ(1-42) globulomer by agents interacting with P/Q-type calcium channels. A: Effects of Aβ(1-42) globulomer on frequency of mixed synaptic currents. B: Effects on median amplitude. Values are given relative to data in control solution. Note suppression of the effect by w-agatoxin and partial recovery of event frequency by roscovitine.

Figure 25:
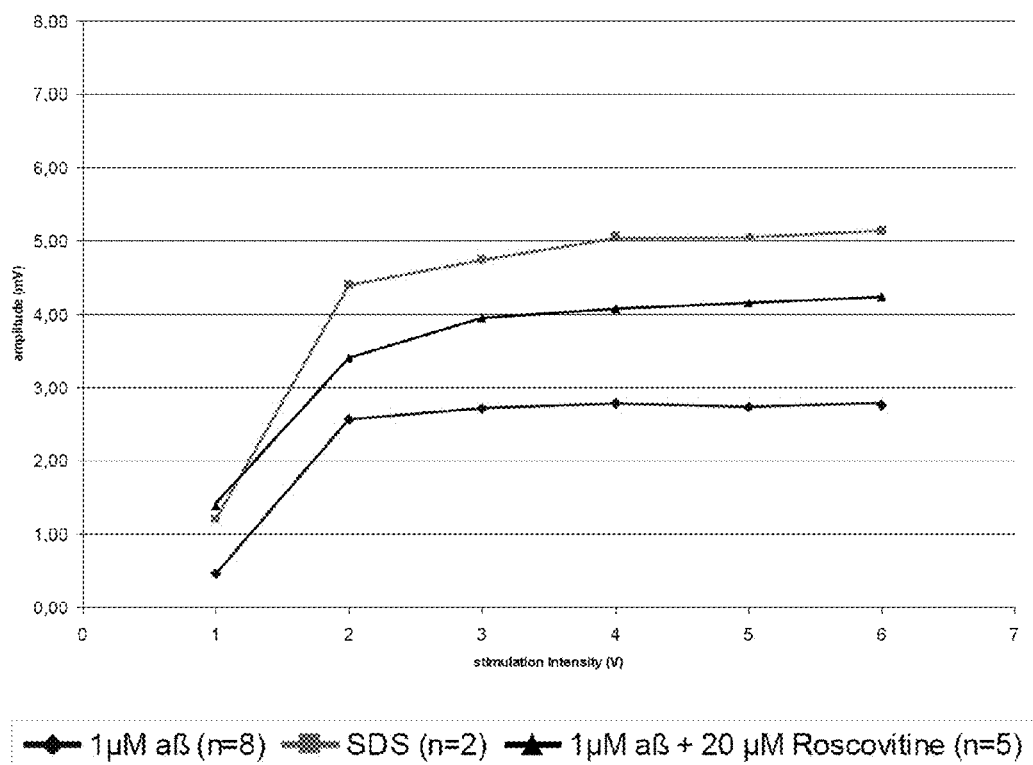

FIG. 25 Enhancing P/Q calcium currents by roscovitine prevents/reverses chronic Aβ globulomer-induced deficits on evoked synaptic transmission in hippocampal tissue (slice cultures). Recordings were performed after incubation with Aβ(1-42) globulomer (at a concentration corresponding to approximately 1 μM of Aβ monomer), Aβ(1-42) globulomer (at a concentration corresponding to approximately 1 μM of Aβ monomer)+20 μM roscovitine, or control (SDS).

Figure 26:
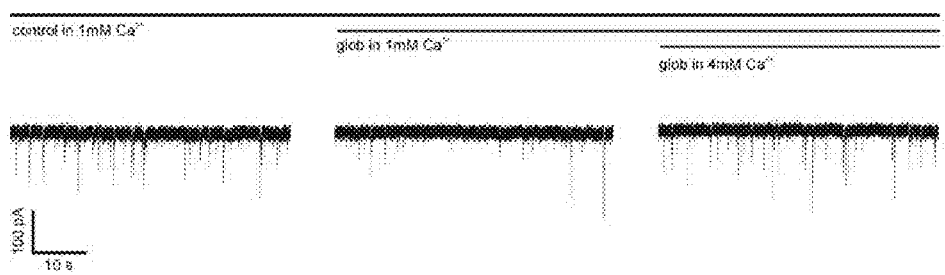
Figure 26:
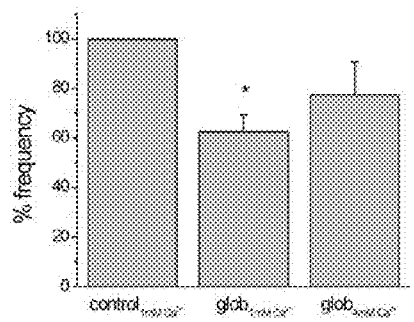
Figure 26:
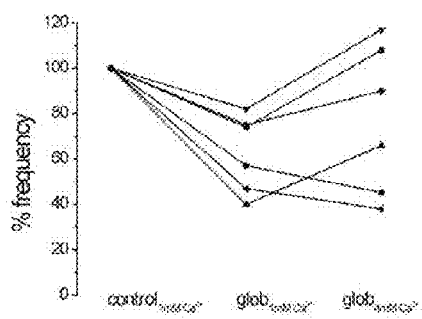
Figure 26:
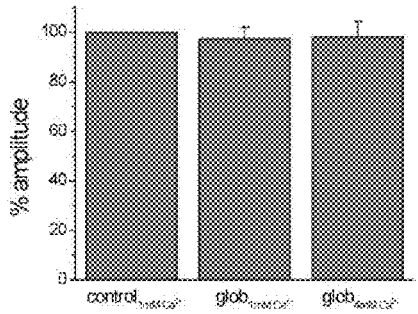
Figure 26:
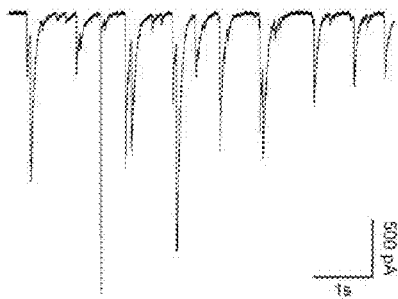

FIG. 26 Effect of extracellular $Ca^{2+}$ on sPSC frequency after treatment with Aβ(1-42) globulomer: Original recording of sPSCs before (control in 1 mM $Ca^{2+}$), after addition of Aβ(1-42) globulomer (glob in 1 mM $Ca^{2+}$) and after subsequent elevation of $Ca^{2+}$-concentration (glob in 4 mM $Ca^{2+}$). B: Reduction of event frequency after application of Aβ(1-42) globulomer ($p<0.05$; n=6) and partial recovery after elevation of $Ca^{2+}$ from 1 mM to 4 mM. Values are given as percentage of control currents. C: Event frequency of single cells (n=6) after application of Aβ(1-42) globulomer and after subsequent elevation of $Ca^{2+}$ from 1 mM to 4 mM. Values are given as percentage of control currents. D: No difference in median amplitude after application of Aβ(1-42) globulomer (n=6) and after subsequent elevation of $Ca^{2+}$. Values are given as percentage of control currents. E: Original recordings of massive discharges directly after $Ca^{2+}$ elevation for the cell shown in A. These currents were rejected from analysis.

Figure 27:
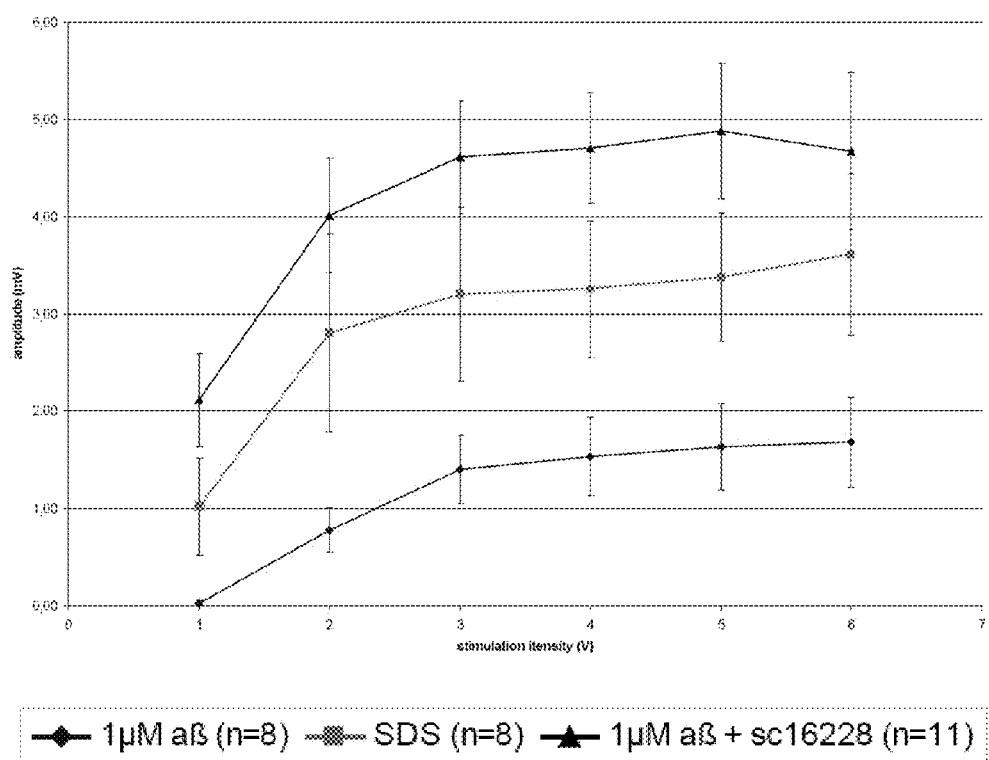

FIG. 27 Inhibiting the interaction of Aβ(1-42) globulomer with the P/Q calcium channels by anti-P/Q type voltage-gated presynaptic calcium channel antibody prevents chronic Aβ globulomer-induced deficits on evoked synaptic transmission in hippocampal tissue. Recordings were performed after incubation with Aβ(1-42) globulomer (at a concentration corresponding to approximately 1 μM of Aβ monomer), Aβ(1-42) globulomer (at a concentration corresponding to approximately 1 μM of Aβ monomer)+0.3 μg/ml (=approximately 2 nM) anti-P/Q antibody, or control (SDS).

Figure 28:
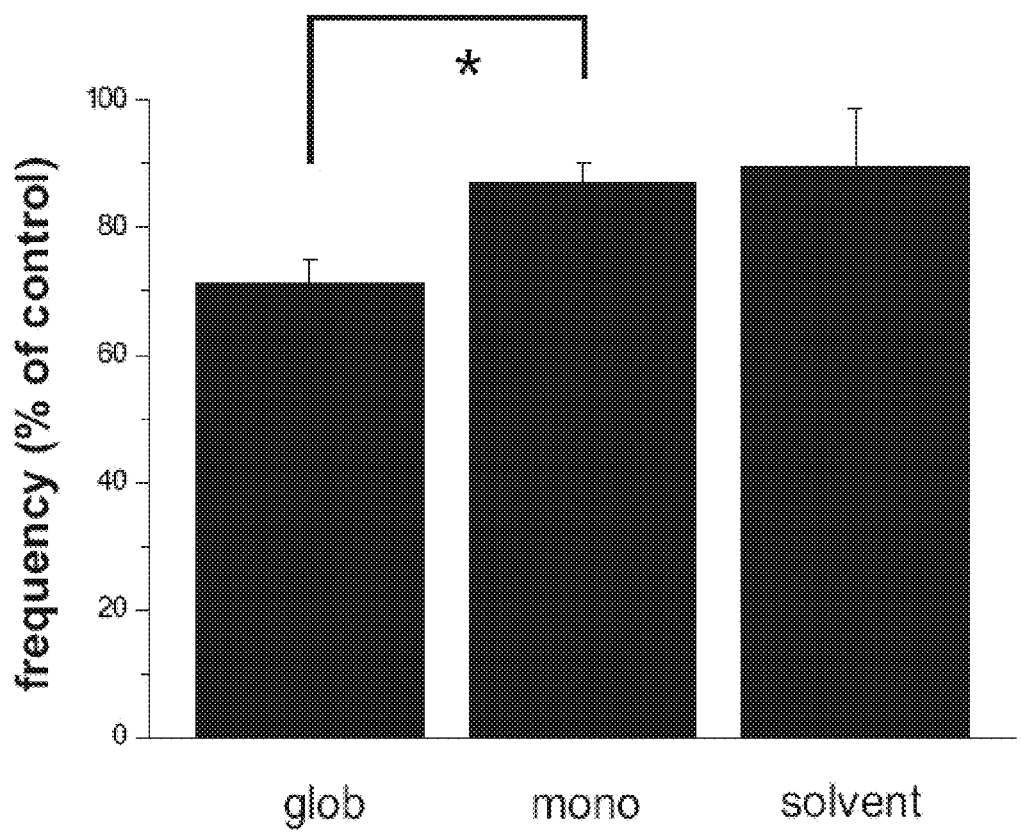

FIG. 28 Bar diagram showing no effect of the monomer on mPSC frequency compared with the significant reduction in frequency induced by the globulomer. The right bar shows that the solvent alone (0.0001% NaOH) does not affect the frequency.

FIRST SERIES OF EXPERIMENTS

Reference Example 1

Determination of Synaptic Potentials

Neuronal cells from the rat hippocampus were obtained and cultured in accordance with methods known per se in the art (Banker G A, Cowan W M, Brain Res. 1977 May 13; 126(3):397-42). Cultured neurons show spontaneous postsynaptic currents (PSCs), i. e. spontaneous PSCs and, in the presence of the sodium channel blocker tetrodotoxin miniature PSCs. As mentioned above, the influx of $Ca^{++}$ through presynaptic ion channels such as the N, P/Q and R type voltage-gated presynaptic calcium channels is what causes the release of neurotransmitter from preformed vesicles in presynaptic terminals. The measured signal reflects the current response of the postsynaptic cell to the release of such transmitters, e.g. gamma-aminobutyric acid or glutamate.

For measurements, primary cell cultures were transferred to a recording chamber mounted on a microscope (Olympus CKX1) and were immersed at room temperature into a buffered solution consisting of 156 mM NaCl, 2 mM KCl, 2 mM $CaCl_2$, 1 mM $MgCl_2$, 16.5 mM glucose and 10 mM HEPES at a pH of 7.3. The osmolarity of the solution was 330 mosmol.

Electrodes were produced by pulling from borosilicate capillaries (available from Science Products) with a horizontal pipette pulling device (P-97 from Sutter Instruments).

After filling with the intracellular solution, the final resistance of the electrodes was from 2 to 5 MΩ. The intracellular solution consisted of either (for recordings of miniature PSCs) 100 mM KCl, 10 mM NaCl, 0.25 mM $CaCl_2$, 5 mM EGTA, 40 mM glucose, 4 mM MgATP and 0.1 mM NaGTP at a pH of 7.3, or (for recording of calcium currents) 110 mM CsCl, 10 mM EGTA, 25 mM HEPES, 10 mM tris-phosphocreatine, 20 U/ml creatine phosphokinase, 4 mM MgATP and 0.3 mM NaGTP.

All test compounds were applied either by bath perfusion or by addition to the bath by means of a micropump connected to a manually guided pipette.

All recordings of miniature PSCs were made in the presence of 0.5 μM tetrodotoxin (TTX; available from Tocris Bioscience) to block the $Na^+$ and $K^+$ channels in the neuronal cell membrane which would otherwise also influence the electrical status of the membrane. For calcium current recordings the extracellular solution contained 140 mM TEA-Cl (to block $K^+$-channels) 10 mM $BaCl_2$, 0.5 μM TTX, 10 mM HEPES and 20 mM glucose at a pH 7.3. When required, w-conotoxin MVIIA (available from Alomone Labs, Jerusalem, Israel) was added to a final concentration of 0.5 μM to block N type voltage-gated presynaptic $Ca^{++}$ channels, thereby "pharmacologically isolating" the ion fluxes through the P/Q type voltage-gated presynaptic calcium channel. If necessary, L-type voltage-gated calcium channels were blocked by addition of 10 μM nifedipine.

To mimic the effect of Aβ globulomer as P/Q type blocker, ω-agatoxin IVA (available from Alomone Labs, Jerusalem, Israel) was added to a final concentration of 0.5 μM to specifically block the P/Q type voltage-gated presynaptic $Ca^{++}$ channels of the sample cell.

All substances were stored as lyophilized powders at −20° C. Stock solutions were prepared with vehicles appropriate for the solubility (i.e. immersion solution). Vehicle was distilled water or standard extracellular solution for all drugs except nifedipine, which was dissolved in ethanol, and roscovitine, which was dissolved in dimethyl sulfoxide (DMSO). The final concentration of the solvents in the Aβ-globulomer solvent buffer which was applied to neurons was <1% and the final concentration of DMSO was <1.5%.

Whole-cell patch-clamp recordings (sPSCs and mPSCs) were conducted in a manner essentially known per se (see, e.g., Sakmann B and Neher E. *Single-Channel Recording*. Springer US, 97 A.D.) at a holding potential of −70 mV using an EPC7 amplifier (available from HEKA Electronics). Signals were filtered at 3 kHz and sampled at 20 kHz.

After formation of a seal, rupture of the membrane by the electrode and establishment of the whole-cell configuration, the perfusion of the bath was stopped, and the substances to be tested were injected into the bath using a custom-made syringe pump.

The sPSCs or mPSCs were then recorded for 10 minutes giving the control values before any toxins were added.

For the selective determination of P/Q type voltage-gated presynaptic calcium channel currents, the cells were activated in a manner known per se (see Yan et al., 2002, supra) by a voltage protocol, where the cells were excited by depolarization to −10 mV for 50 ms every 20 sec. After the formation of the whole-cell configuration, currents increased steadily until they had reached a stable amplitude level. After this stable amplitude level had been established, the effects of different test compounds on the rate of ion flux were observed and expressed in terms of the normalized mean P/Q amplitude and standard error of the mean SEM. Frequency and amplitude of synaptic currents were calculated offline using a template-based algorithm (custom made routine within the Signal and Spike software, purchased from CED Inc., Cambridge, UK).

When desired, the measurement was evaluated at several timepoints and optionally after a washout. Student's t-test was applied to determine significance, $p<0.05$ being considered as indicative of significant differences.

Reference Example 2

Generation of Aβ Globulomer

An Aβ(1-42) globulomer preparation with an apparent molecular weight of 38/48 kDa as determined by SDS-PAGE was obtained as described in Example 6b of WO2004/067561. Essentially, Aβ monomer was pretreated with HFIP for dissolving hydrogen bonds, then diluted and further incubated in the presence of 0.2% SDS, followed by isolation of the thus formed globulomer.

In brief, lyophilized Aβ(1-42) synthetic peptide was disaggregated by using 100% 1,1,1,3,3,3 hexafluoro-2-propanol. After evaporation, Aβ(1-42) was resuspended at a concentration of 5 mM in dimethylsulfoxide, diluted to a final concentration of 400 μM in PBS containing 0.2% SDS. After 6 h incubation at 37° C., the sample was diluted with three volumes of $H_2O$ and incubated for another 18 h at 37° C. The sample was concentrated by ultrafiltration (30 kDa cutoff), dialyzed against 5 mM $NaH_2PO_4$ 35 mM NaCl, pH 7.4, centrifuged at 10,000×g for 10 min, and the supernatant containing the 48 kDa Aβ(1-42) globulomer withdrawn. Aβ(1-42) globulomer was diluted in extracellular solution at the concentration indicated immediately before experiments. Currents were measured before and immediately after addition of Aβ(1-42) globulomer to the bath solution.

For control experiments, synthetic monomeric Aβ(1-42) peptide (H-1368; Bachem, Bubendorf, Switzerland) was dissolved in 0.1% NaOH, yielding a 1 mM stock solution, which was frozen at −80° C. Immediately before the experiment, this solution was dissolved at 1:500 in bath solution, which was added to the bath by means of a micropump, resulting in a final concentration of 1 μM.

Example 3

Inhibitory Effect of Aβ Globulomer on Spontaneous Synaptic Activity

Using acute application of the P/Q channel blocker ω-agatoxin as a negative control and cells untreated with regard to the P/Q type voltage-gated presynaptic calcium channel as a positive control, the effects of Aβ(1-42) globulomer on the frequency of spontaneous synaptic events in cultured hippocampal neurons treated with ω-conotoxin to achieve synaptic dominance of the P/Q type channel, as described in Reference Example 1, were observed.

Aβ globulomer, obtained as described in Reference Example 2, was tested according to the procedure described in Reference Example 1 for channel function inhibitors such as w-agatoxin. In the presence of ω-agatoxin, Aβ globulomer had no further effect on synaptic activity, indicating that the effects of both agents involved a common mechanism. A total of 200 μl Aβ-globulomer solvent buffer comprising a Aβ(1-42) globulomer concentration corresponding to approximately 2 μM of Aβ monomer was added to the bath (previous volume 200 μl), resulting in a final Aβ(1-42) globulomer concentration corresponding to approximately 1 μM of Aβ monomer. Based on the assumption that the Aβ(1-42) globulomer consists of 12 Aβ(1-42) monomers a final Aβ(1-42)

globulomer concentration of approximately 83 nM can be calculated. Measurements of synaptic activity were then taken.

Results are shown in FIGS. 1-7, demonstrating that the Aβ globulomer inhibits the frequency of spontaneous synaptic events with an efficiency approaching that of the strong P/Q inhibitor ω-agatoxin but has no or little effect on the amplitude of the synaptic events. Thus, Aβ(1-42) globulomer reduces synaptic activity, most likely by a presynaptic mechanism, which shares crucial elements with the effect of ω-agatoxin.

These results were verified by subjecting the Aβ(1-42) globulomer containing Aβ-globulomer solvent buffer to ultrafiltration with a filter having a molecular cutoff size of 5 kDa for globular proteins. The resulting solvent buffer contained no detectable amounts of Aβ globulomer protein prior to bringing it into contact with the cells. The ultrafiltrate had no effect on the synaptic events (see FIG. 2), indicating that the agent responsible for reducing the frequency of spontaneous synaptic events was unable to pass ultrafilters.

Figure 1A:
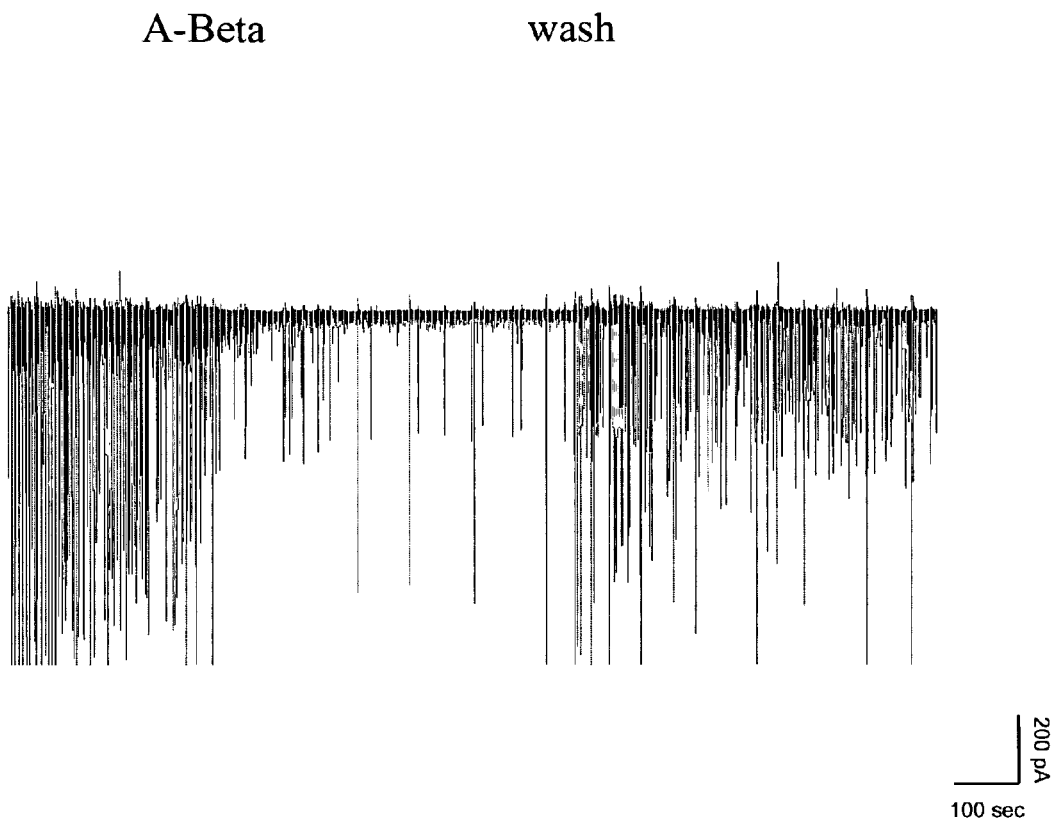
FIG. 1: Effect of Aβ(1-42) globulomer on spontaneous synaptic activity as recorded from rat primary cultured hippocampal neurons by voltage clamp: (A) and (C) are recordings of spontaneously occurring synaptic currents in a cultured hippocampal neuron (downward deflections indicate the postsynaptic currents which are elicited by neurotransmitter release from one or more presynaptic neurons; application of the globulomer and washout (top trace) are indicated); (B) and (D) are the cumulative probability functions.
Figure 1B:
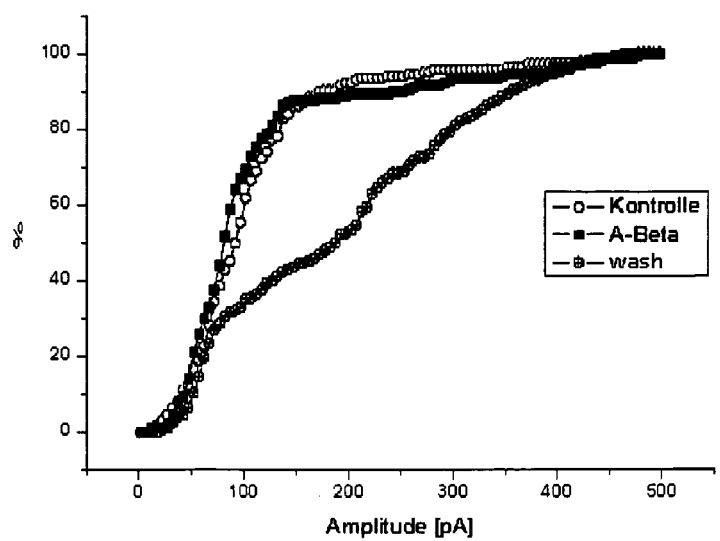
Figure 1C:
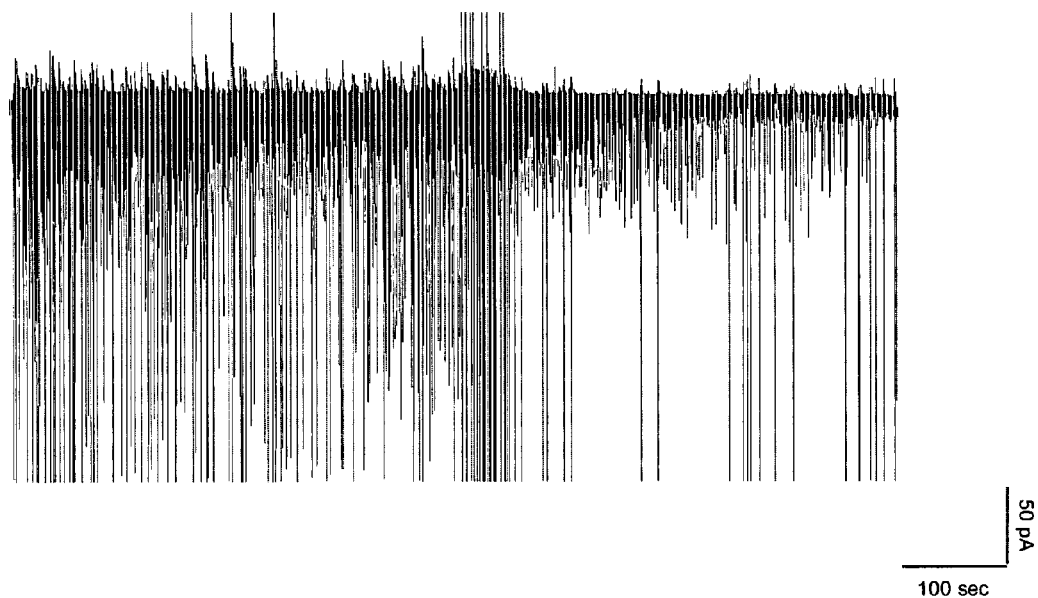
Figure 1D:
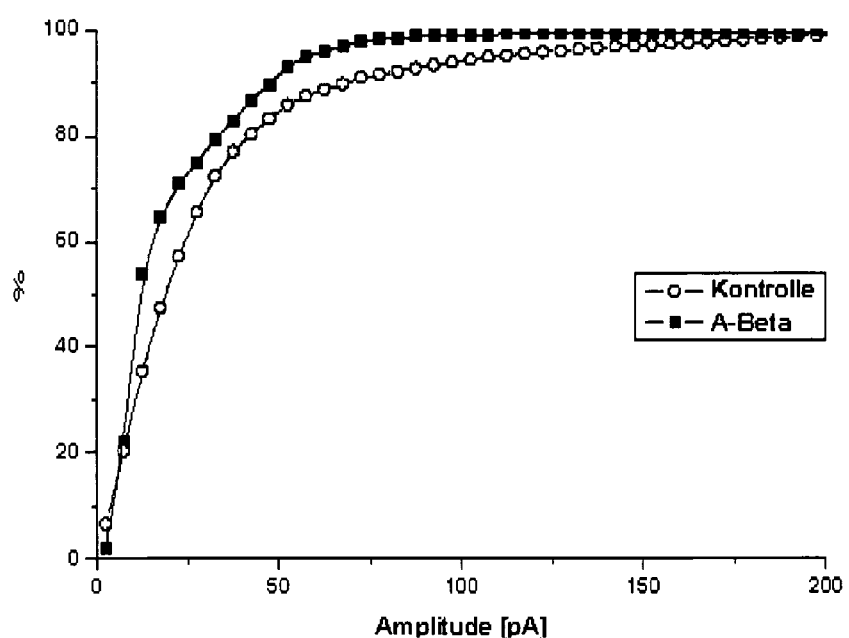
Figure 2:
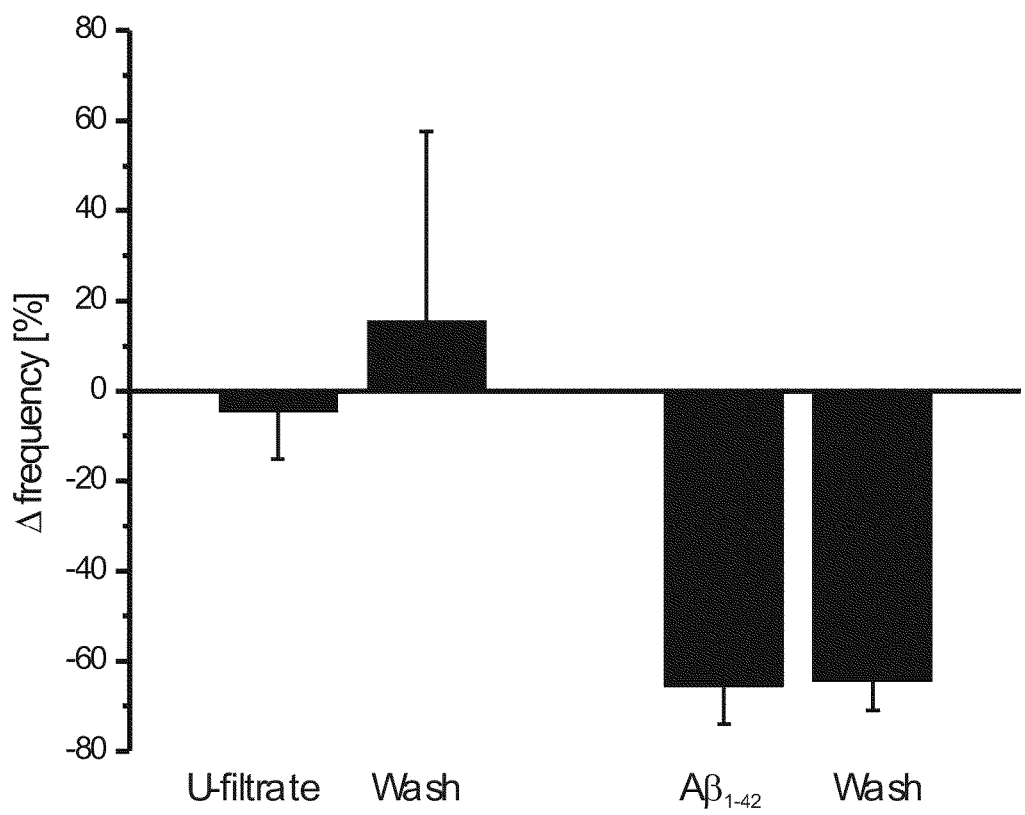
FIG. 2: Effect of Aβ(1-42) globulomer on the frequency of synaptic currents.
Figure 3:
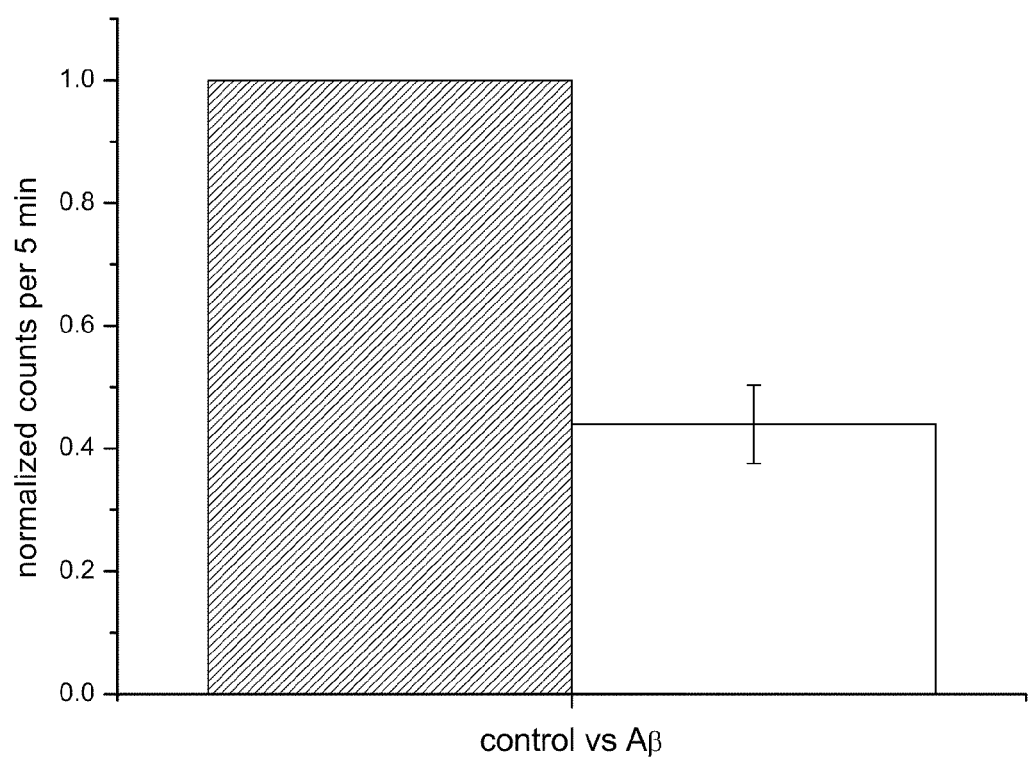
FIG. 3: Effect of Aβ(1-42) globulomer on the frequency of mIPSCs in of cells cultivated with 0.5 μM ω-conotoxin MVIIA to achieve synaptic P/Q predominance (n=6): Number of synaptic events during 5 min relative to non-Aβ globulomer treated cells. Left to right: (1) non-Aβ globulomer treated P/Q-dominated cells=reference, (2) P/Q-dominated cells treated with Aβ globulomer (at a concentration corresponding to approximately 1 μM of Aβ monomer).
Figure 4:
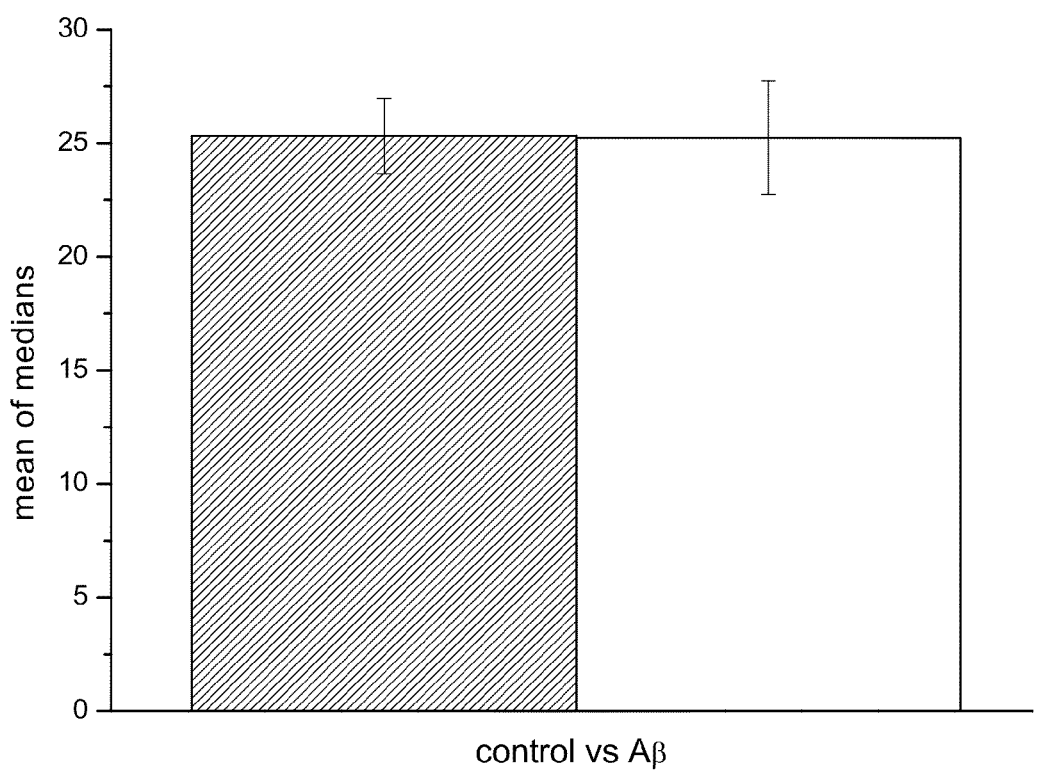
FIG. 4: Aβ(1-42) globulomer has no effect on the amplitude of mIPSCs of cells cultivated with ω-conotoxin MVIIA to achieve synaptic P/Q predominance: Average amplitude of synaptic events relative to non-Aβ globulomer treated cells. Left to right: (1) non-Aβ globulomer treated P/Q-dominated cells=reference, (2) P/Q-dominated cells treated with Aβ globulomer (at a concentration corresponding to approximately 1 μM of Aβ monomer).
Figure 5:
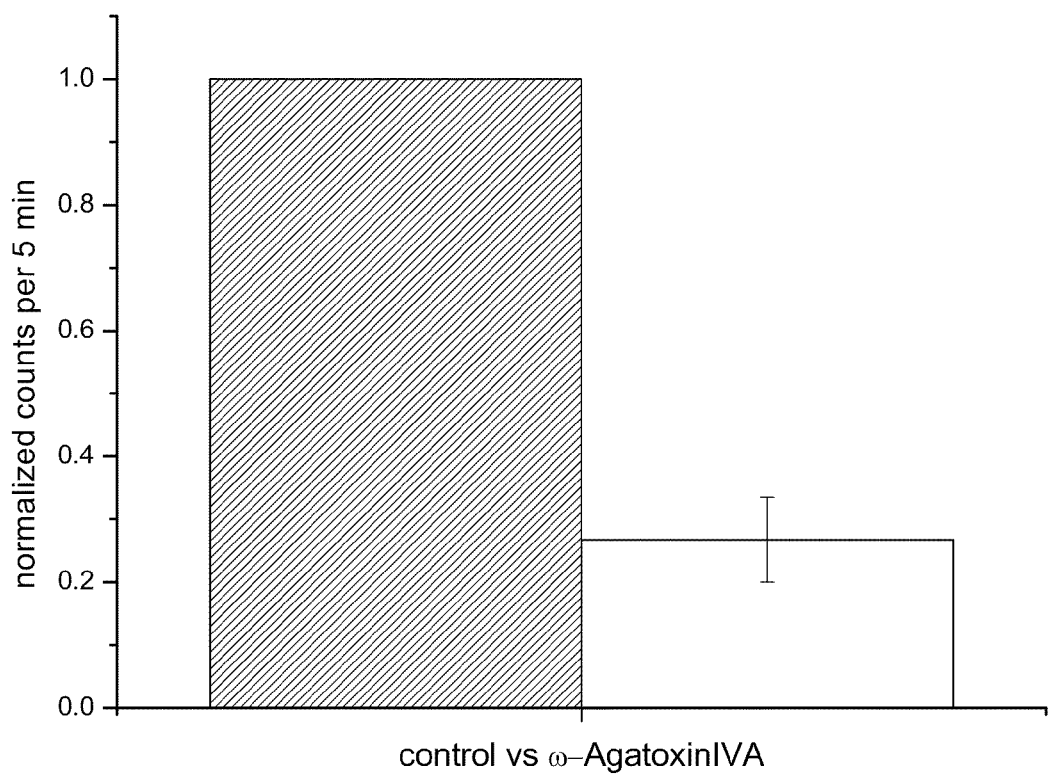
FIG. 5: Effect of ω-agatoxin on the frequency of mIPSCs in of cells cultivated with 0.5 μM ω-conotoxin MVIIA to achieve synaptic P/Q predominance (n=3): Number of synaptic events during 5 min relative to non-ω-agatoxin treated cells. Left to right: (1) non-ω-agatoxin treated P/Q-dominated cells=reference, (2) P/Q-dominated cells treated with 0.5 μM ω-agatoxin.
Figure 6:
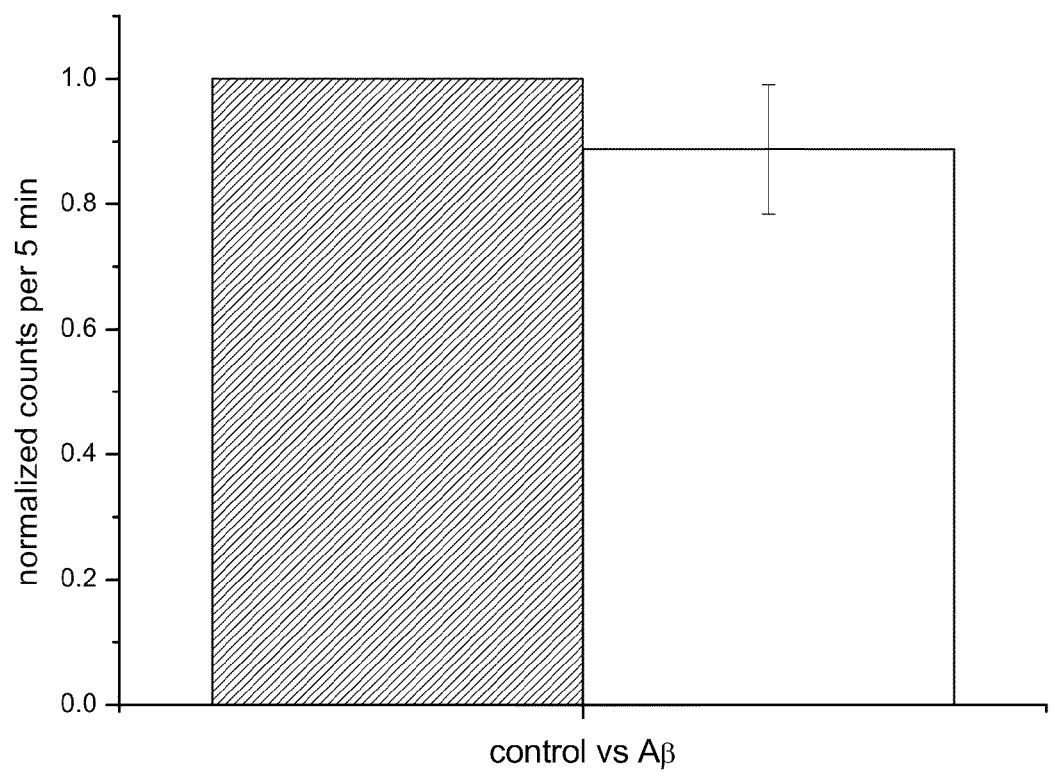
FIG. 6: No additive effect on the frequency of mIPSCs in of cells cultivated with 0.5 μM ω-conotoxin MVIIA to achieve synaptic P/Q predominance after blockade of P/Q-channels by ω-agatoxin (n=6): Number of synaptic events during 5 min relative to non-Aβ globulomer treated cells. Left to right: (1) non-Aβ globulomer treated P/Q-dominated cells (ω-agatoxin only)=reference, (2) P/Q-dominated cells treated with Aβ globulomer (at a concentration corresponding to approximately 1 μM of Aβ monomer) after pre-treatment with 0.5 μM ω-agatoxin.
Figure 7:
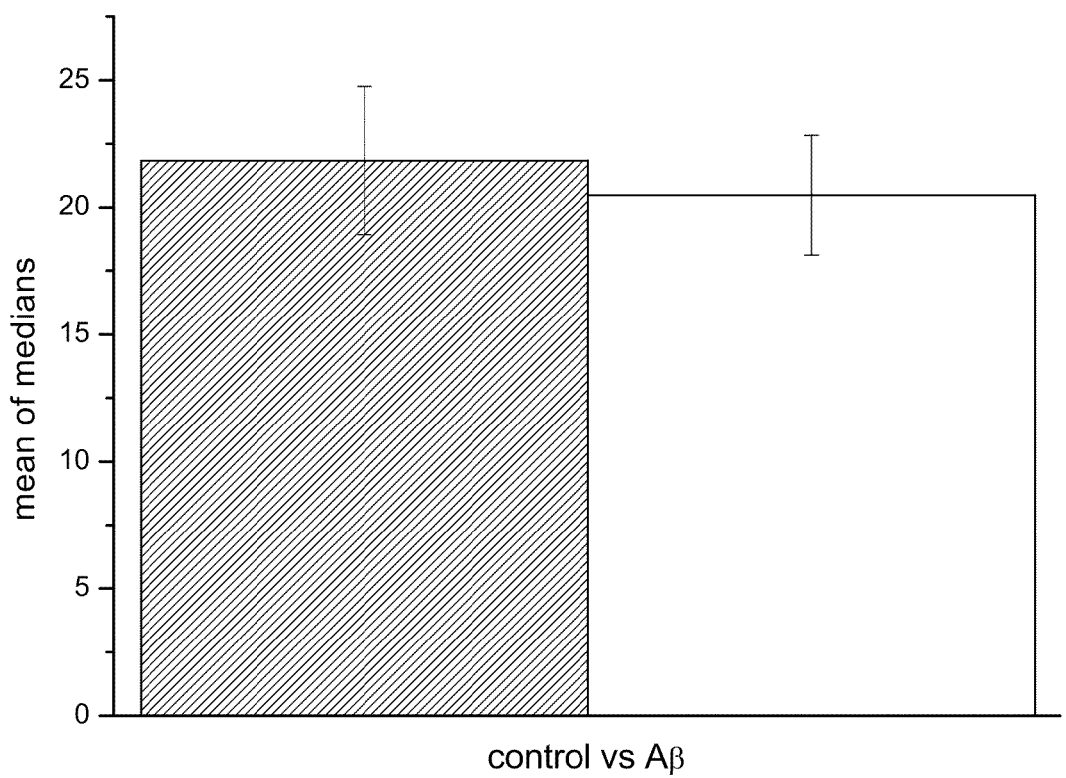
FIG. 7: No effect of globulomer on the amplitude of mIPSCs when P/Q channels of P/Q-dominated cells are already blocked by 0.5 μM ω-agatoxin IVA (n=6): Number of synaptic events during 5 min relative to non-Aβ globulomer treated cells. Left to right: (1) non-Aβ globulomer treated P/Q-dominated cells (ω-agatoxin only)=reference, (2) P/Q-dominated cells treated with Aβ globulomer (at a concentration corresponding to approximately 1 μM of Aβ monomer) after pre-treatment with 0.5 μM ω-agatoxin.
Figure 8:
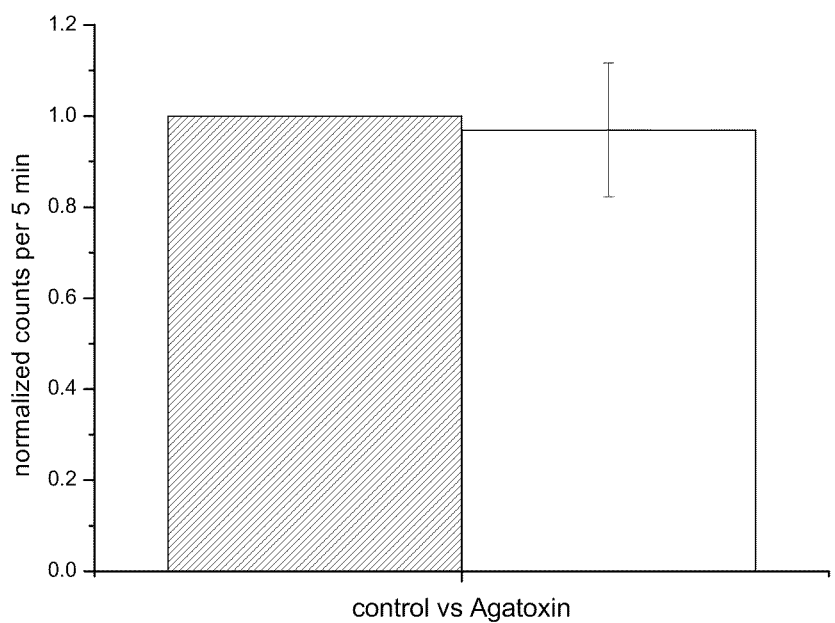
FIG. 8: Agatoxin does not impair spontaneous synaptic activity in cultures that lack functional P/Q-type $Ca^{++}$ channels: Number of synaptic events during 5 min was set to 100% for each cell analysed. The right bar indicates the relative number of synaptic events in each cell after application of 0.5 μM ω-agatoxin.
Figure 9:
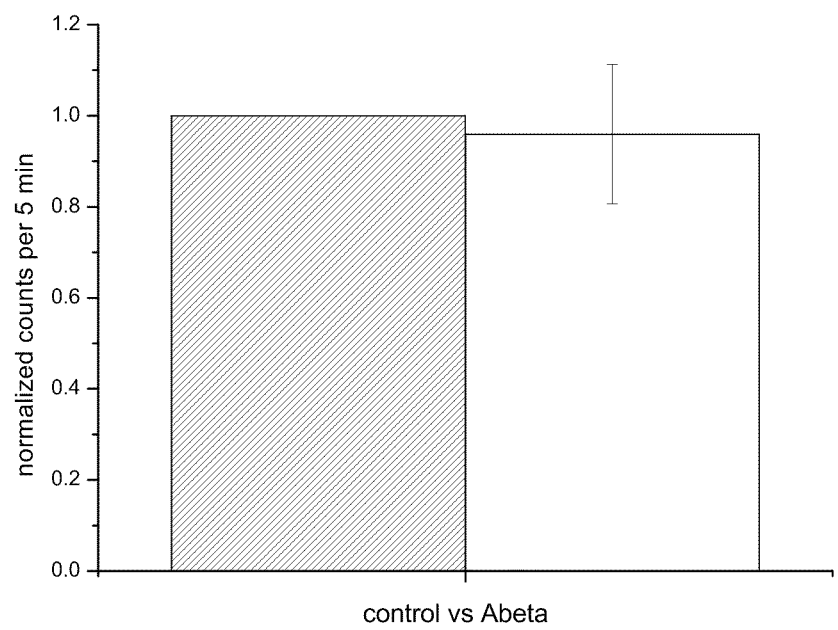
FIG. 9: Globulomer does not impair spontaneous synaptic activity in cultures that lack functional P/Q-type $Ca^{++}$ channels: Number of synaptic events during 5 min relative to non-Aβ globulomer treated cells was set to 100% for each cell analysed. The right bar indicates the relative number of synaptic events in each cell after application of Aβ globulomer (at a concentration corresponding to approximately 1 μM of Aβ monomer).

Furthermore, the effect of Aβ(1-42) globulomer is absent in cells predominantly expressing presynaptic N-type calcium channels. Results are shown in FIGS. 8 and 9, demonstrating that in the N-dominated cells no reduction of the frequency nor any reduction in amplitude is achieved by either ω-agatoxin or Aβ globulomer, i. e. that both w-agatoxin and Aβ globulomer target the P/Q type voltage-gated presynaptic calcium channel.

Example 4

Rescue of Spontaneous Synaptic Activity by Roscovitine

Using the Aβ(1-42) globulomer of Reference Example 2 as a negative control and cells untreated with regard to the P/Q type voltage-gated presynaptic calcium channel as a positive control, the effects of the P/Q type voltage-gated presynaptic calcium channel activator roscovitine on the Aβ globulomer-induced reduction of the frequency of spontaneous synaptic events in cultured hippocampal neurons treated with ω-conotoxin, as described in Reference Example 1, were observed.

Roscovitine was used at a final concentration of 20 μM, by adding it simultaneously with Aβ(1-42) globulomer (final concentration of Aβ globulomer corresponding to approximately 1 μM of Aβ monomer). Roscovitine is known (Zhen Yan et al., J. Physiol. 540: 761-770 (2002)) to slow down the inactivation of the P/Q type voltage-gated presynaptic calcium channel, i. e. to extend the time for which a channel, once opened, remains in the open state, thereby increasing the calcium ion flow through the P/Q type voltage-gated presynaptic calcium channel.

Figure 10:
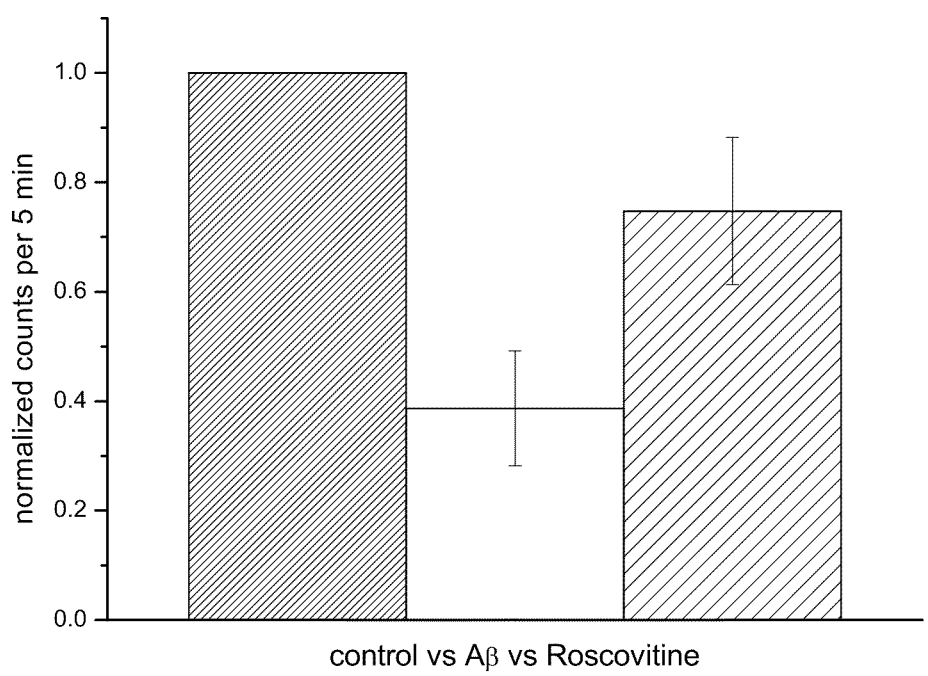
FIG. 10: Suppression of spontaneous synaptic currents by Aβ(1-42) globulomer and its reversal by the P/Q channel agonist roscovitine: Number of synaptic events during 5 min relative to non-Aβ globulomer treated P/Q-dominated cells. Left to right: (1) non-Aβ globulomer treated P/Q-dominated same cells=reference, (2) P/Q-dominated same cells treated with Aβ globulomer (at a concentration corresponding to approximately 1 μM of Aβ monomer), (3) P/Q-dominated same cells treated simultaneously with Aβ globulomer (at a concentration corresponding to approximately 1 μM of Aβ monomer) and 20 μM roscovitine.
Figure 11:
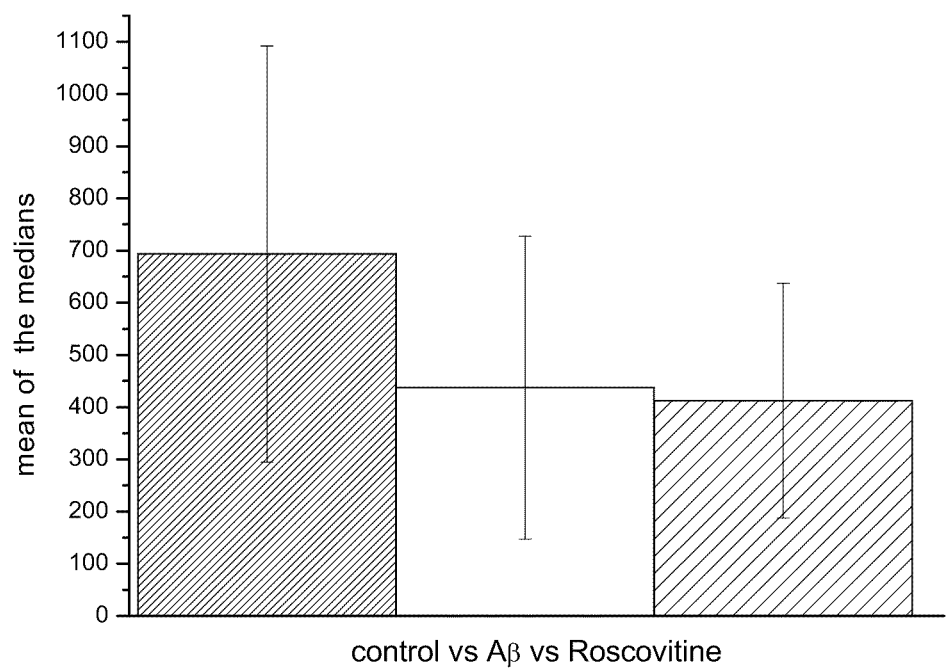
FIG. 11: No effect on the amplitude of spontaneous synaptic currents of the P/Q channel agonist roscovitine: Average amplitude of synaptic events relative to non-Aβ globulomer treated P/Q-dominated cells. Left to right: (1) non-Aβ globulomer treated P/Q-dominated same cells=reference, (2) P/Q-dominated same cells treated with Aβ globulomer (at a concentration corresponding to approximately 1 μM of Aβ monomer), (3) P/Q-dominated same cells treated simultaneously with Aβ globulomer (at a concentration corresponding to approximately 1 μM of Aβ monomer) and 20 μM roscovitine.
Figure 12:
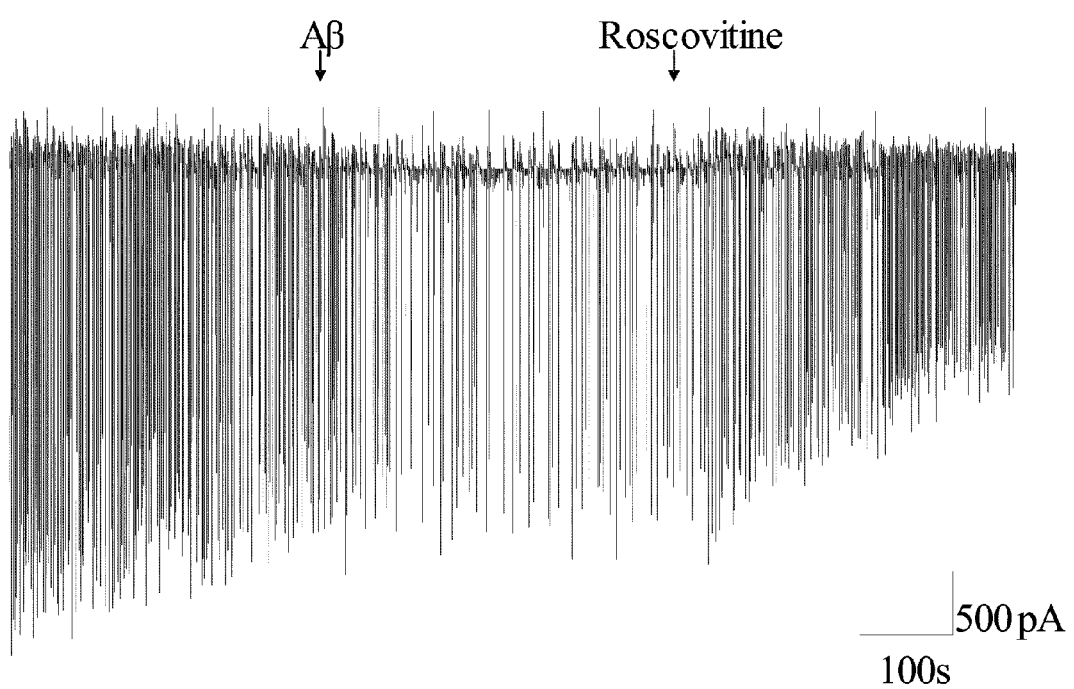
FIG. 12: The effect of Aβ(1-42) globulomer on spontaneous synaptic activity of P/Q-dominated cells can be reversed by the P/Q channel agonist roscovitine: Synaptic potentials over time. Arrows indicate the time points when Aβ globulomer (at a concentration corresponding to approximately 1 μM of Aβ monomer) and 20 μM roscovitine, respectively, were added.
Figure 13:
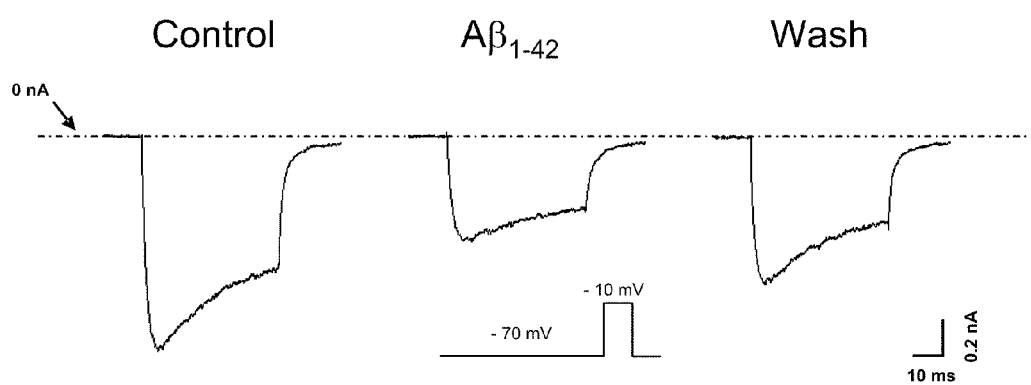
FIG. 13: Reducing effect of Aβ globulomer on the amplitude of pharmacologically isolated P/Q-type calcium channels: Traces represent membrane currents after activation of P/Q-type channels by a depolarizing voltage step. Left to right: (1) P/Q-current under control conditions, (2) P/Q-current of the same cell after application of Aβ globulomer (at a concentration corresponding to approximately 1 μM of Aβ monomer), (3) P/Q-current of the same cell after washout of Aβ globulomer.
Figure 14:
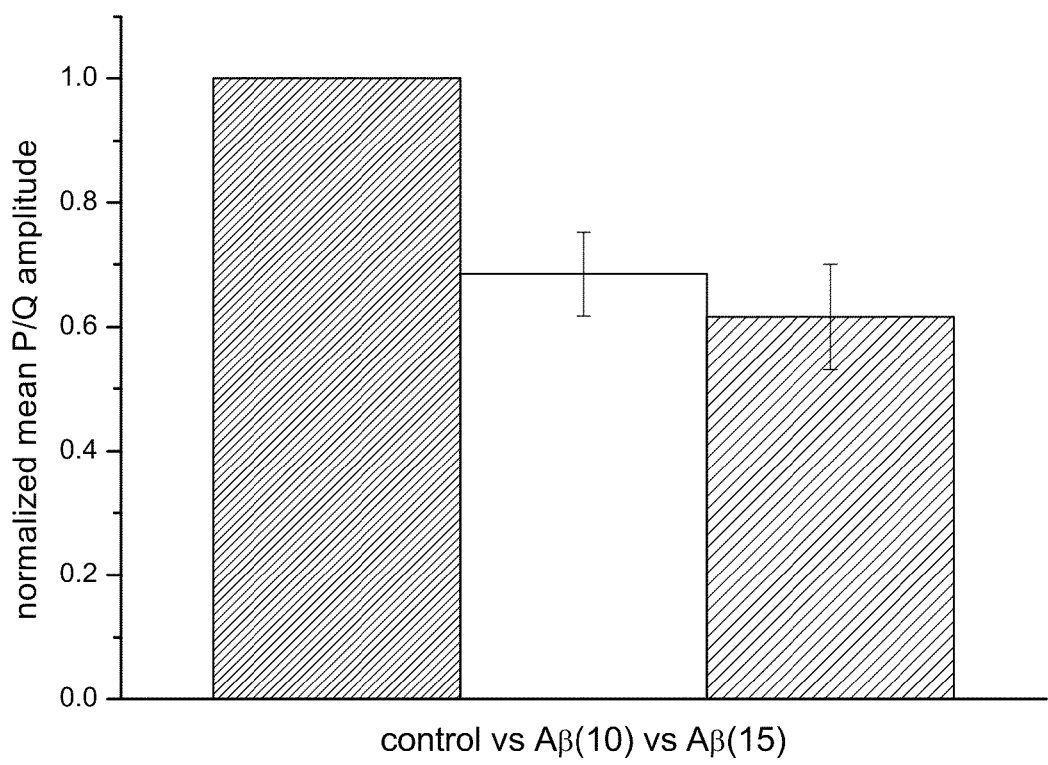
FIG. 14: Effect of Aβ(1-42) globulomer on the pharmacologically isolated P/Q current at different time points: Average amplitude of P/Q-mediated current amplitude relative to non-Aβ globulomer treated P/Q-dominated cells. Left to right: (1) non-Aβ globulomer treated same cells=reference, (2) same cells 10 min after treatment with Aβ globulomer (at a concentration corresponding to approximately 1 μM of Aβ monomer), (3) same cells 15 min after treatment with Aβ globulomer (at a concentration corresponding to approximately 1 μM of Aβ monomer).
Figure 15:
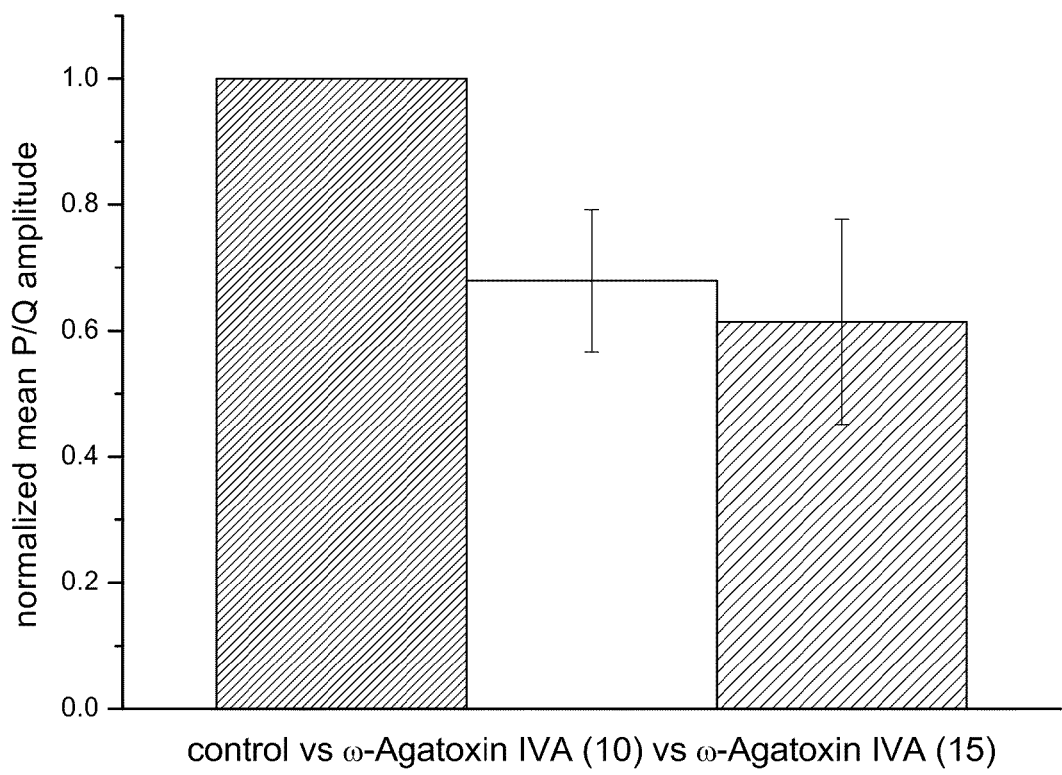
FIG. 15: Effect of 0.5 μM ω-agatoxin IVA on the pharmacologically isolated P/Q current at different time points: Average amplitude of P/Q currents relative to non-ω-agatoxin treated P/Q-dominated same cells. Left to right: (1) non-ω-agatoxin treated P/Q-dominated same cells=reference, (2) P/Q-dominated cells 10 min after treatment with 0.5 μM ω-agatoxin, (3) P/Q-dominated cells 15 min after treatment with 0.5 μM ω-agatoxin.
Figure 16:
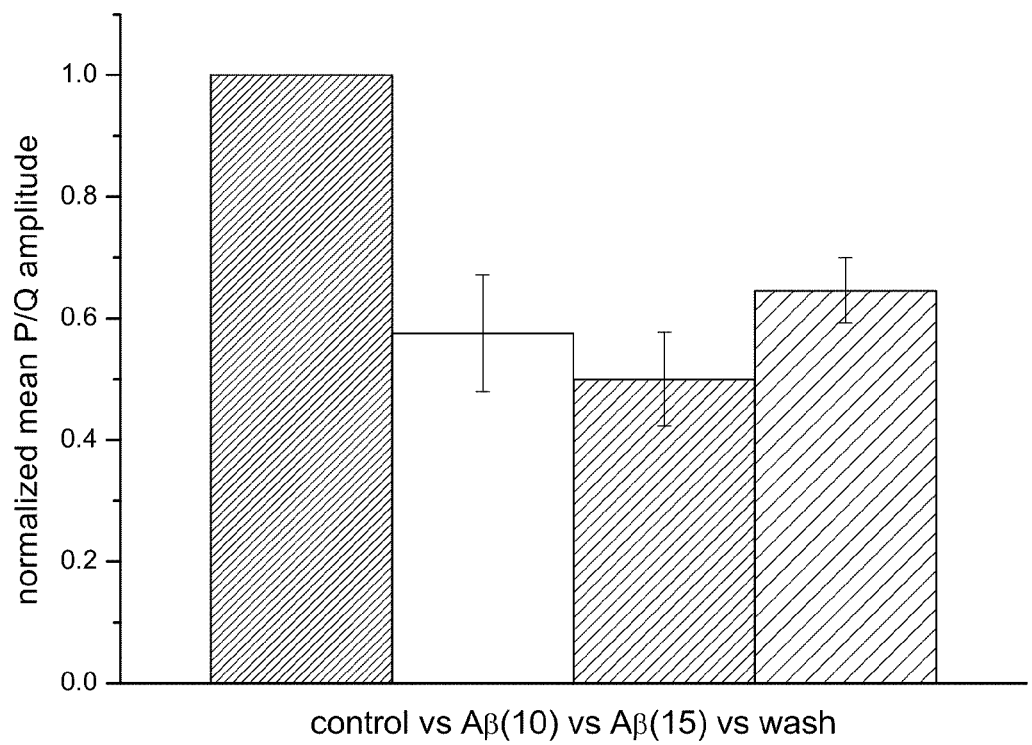
FIG. 16: Effect of Aβ on the pharmacologically isolated P/Q current at different time points, revealing the effect of washing out the Aβ globulomer: Average amplitude of P/Q-mediated current relative to non-Aβ globulomer treated P/Q-dominated cells. Left to right: (1) non-Aβ globulomer treated P/Q-dominated cells=reference, (2) P/Q-dominated cells 10 min after treatment with 83 nM Aβ globulomer (at a concentration corresponding to approximately 1 μM of Aβ monomer), (3) P/Q-dominated cells 15 min after treatment with Aβ globulomer (at a concentration corresponding to approximately 1 μM of Aβ monomer), (4) P/Q-dominated cells treated with Aβ globulomer (at a concentration corresponding to approximately 1 μM of Aβ monomer) after washing out the Aβ globulomer.

Results are shown in FIGS. 10 and 11, demonstrating that a P/Q type voltage-gated presynaptic calcium channel activator is capable of restoring the frequency of spontaneous synaptic events under the influence of Aβ globulomer to almost that of untreated cells, i. e., that a P/Q activator may be used to reverse the detrimental effects of Aβ globulomer.

Reference Example 5

Direct Determination of the Activity of the P/Q Type Voltage-Gated Presynaptic Calcium Channel, and of Inhibitory and Activating Influences, by the Voltage-Clamp Method Cells were prepared and subjected to measurement of membrane currents by the voltage-clamp method basically as described in Reference Example 1, the difference being essentially that all irrelevant (non-P/Q type) ion channels of the cells were blocked chemically, thereby allowing for direct determination of the ion fluxes rather than of the resulting IPSCs. Blocking of the irrelevant channels was achieved using the following additions to the bath or electrode solution:

| Compound | Concentration | Channel blocked |
| --- | --- | --- |
| TEA-Cl | 140 mM | I[K$^+$] |
| BaCl$_2$ | 10 mM | |
| CsCl (in the pipette) | 110 mM | |
| Nifedipine | 10 mM | L-type Ca$^{++}$ channel |
| ω-conotoxin MVIIA | 0.5 mM | N-type Ca$^{++}$ channel |
| Tetrodotoxin | 0.5 | Na$^+$ channels |

The Ba$^{++}$ also served as the charge carrier (i. e. substrate replacement) for the P/Q type voltage-gated presynaptic Ca$^{++}$ channel, with the additional advantage that conductance through this channel and hence the sensitivity of the assay were thereby increased to approximately tenfold. This made it possible to directly detect ion fluxes through P/Q-channels in somatic recordings.

In order to prevent the "run down" of Ca$^{++}$ currents in the samples, the electrode solution also comprised, in addition to the substances listed above, 10 mM tris-phospho-creatinine and 20 U/ml creatine phosphokinase, which together served as an ATP regenerating system preventing "run-down", i.e. decline due to a gradual loss of channel conductance, of the observed currents. ATP is needed to maintain the conductance of the calcium channels over time intervals longer than several minutes, allowing to conduct the described pharmacological experiments with sufficiently stable calcium currents.

Example 6

Direct Effect of Aβ Globulomer on the P/Q Type Voltage-Gated Presynaptic Calcium Channel in Cultured Cells Using ω-agatoxin as a negative control and cells untreated with regard to the P/Q type voltage-gated presynaptic calcium channel as a positive control, the effects of approximately Aβ(1-42) globulomer of Reference Example 2 (at a concentration corresponding to approximately 1 μM of Aβ(1-42) monomers) on calcium flux in hippocampal neurons treated with w-conotoxin were directly observed as described in Reference Example 5.

Recordings were taken at 10 min and 15 min and optionally after a washout. Typical results are shown in FIGS. 13-16. These findings demonstrate that Aβ globulomer directly inhibits the activity of the P/Q type voltage-gated presynaptic calcium channel and cannot be readily washed out after binding to the P/Q type voltage-gated presynaptic calcium channel. They further demonstrate that Aβ globulomer impedes, by decreasing the amplitude of the calcium flux, the initiation of synaptic currents.

Example 7

Direct Effect of Aβ Globulomer on the P/Q Type Voltage-Gated Presynaptic Calcium Channel in situ To verify whether the effect of the globulomer on neurons in cell cultures also takes place in the more organotypic slice-preparation of the hippocampus, synaptic currents were determined in this tissue.

400 μm thick slices were prepared from freshly dissected hippocampi of the mouse using a method known per se (Dingledine R. *Brain Slices*. New York: Plenum Press, 1983). CA1 pyramidal cells were patched and spontaneous synaptical currents were recorded prior and after application of Aβ(1-42) globulomer via an Eppendorff pipette.

Figure 17:
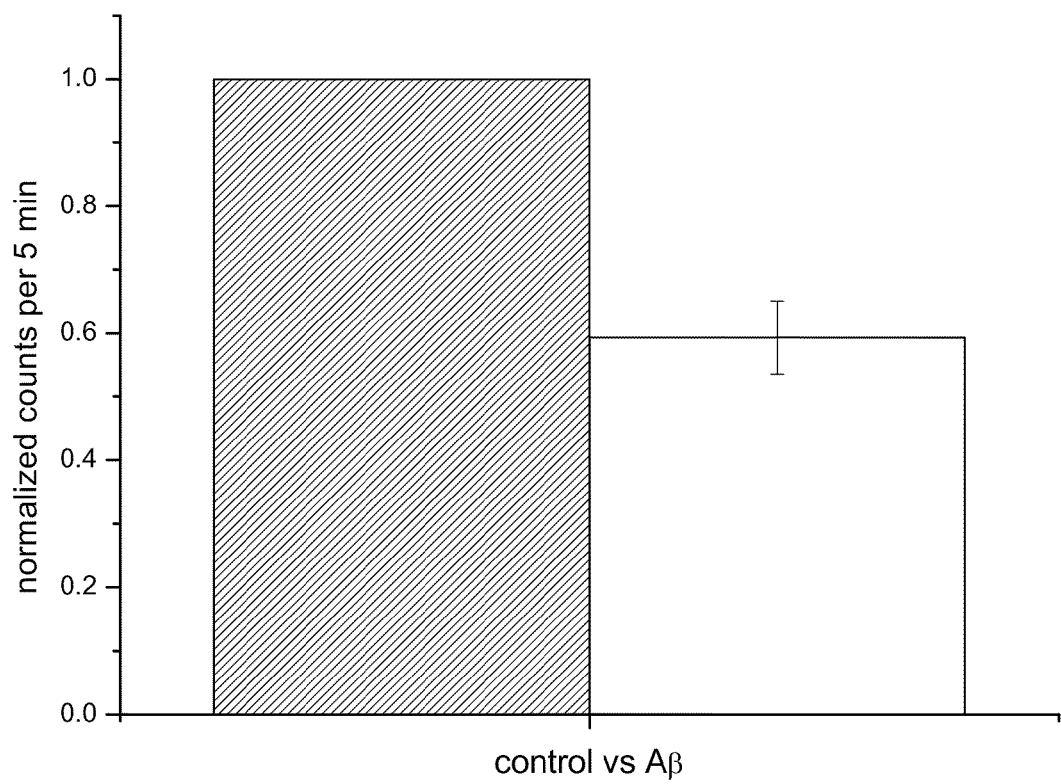
FIG. 17: Effect of Aβ on spontaneous synaptic activity in the hippocampal slice: Number of synaptic events during 5 min relative to non-Aβ globulomer treated tissue. Left to right: (1) non-Aβ globulomer treated same slice=reference, (2) same slice treated with Aβ globulomer (at a concentration corresponding to approximately 1 μM of Aβ monomer).

Typical results are shown in FIG. 17. These findings demonstrate that the mechanism for Aβ globulomer mediated inhibition disclosed herein is also valid in situ.

Example 8

Physical Binding of Aβ Globulomer to the P/Q Type Voltage-Gated Presynaptic Calcium Channel The Aβ(1-42) globulomers of Reference Example 2 were used as a ligand in an affinity chromatographic approach to identify amyloid-binding proteins isolated from rat brain homogenates. The Aβ(1-42) globulomers were covalently coupled to a suitable matrix, and affinity purified proteins were eluted sequentially and analyzed by mass spectrometry. This affinity purification resulted in biochemical identification of the Calcium Channel B1, which has 94% identity with the human α1 subunit of the P/Q channel.

a) Immobilization of Aβ(1-42) Globulomers 0.5 ml of commercially available NHS-Sepharose (Pharmacia™, ≈16-23 μmol/ml) was washed twice with 25 ml of 30% isopropanol in 1 mM HCl and five times with 10 ml of 1 mM HCl. Then the sepharose was washed five times with NHS coupling buffer. All washing steps were performed on ice. Then 650 μl of Aβ(1-42) globulomers of Reference Example 2 and 650 μl of NHS coupling buffer were added to the gel material. Upon incubation at room temperature for 2 h, the suspension was pelleted at 2000 g for 5 min. Free $NH_2$ groups were blocked with 5 ml NHS blocking buffer for 2 h at room temperature. The Aβ-sepharose was washed with NHS storage buffer and centrifuged. Then 500 μl NHS-storage buffer and 0.02% sodium azide to prevent microbiological growth were added. The suspension was stored at +4° C. until further use.

TABLE 1

Buffers for immobilization.

| NHS-coupling buffer | NHS-blocking buffer | NHS-storage buffer |
|---|---|---|
| 50 mM NaHCO₃ pH 7.5 | 50 mM NaHCO₃ pH 7.5 | 50 mM NaHCO₃ pH 7.5 |
| | 250 mM ethanolamine | 0.025% SDS |
| | 0.025% SDS | | b) Membrane Purification of 50 g Rat Homogenates

Brains were isolated from rats, and 50 g rat brain were added to 450 ml Homogenization Buffer and homogenized with an Ultra Turrax for 20 min at rising speed. The homogenate was centrifuged for 20 min at 2500 rpm (about 1000 g) to remove cell debris. The supernatant was spun down for 25 min at 16000 rpm (about 20000 g) and the pellet was discarded. Next, the 20000 g supernatant was centrifuged for 1 h at 32000 rpm (about 80000 g). The resulting pellets were resupendend with 1 ml PBS each to a final volume of 12.5 ml and pottered with three strokes. The 80000 g supernatant was centrifuged for 1 hour at 43000 rpm (about 150000 g). The 150000 g pellets were resuspended in 500 μl PBS and homogenized by the Ultra Turrax. The 150000 g supernatant was discarded. Subsequently, total protein amount was measured and 11.58 mg/ml protein for the 80000 g fraction and 10.02 mg/ml for the 150000 g fraction were obtained. The proteins of the 80000 g and 150000 g homogenates were solubilized with 2% CHAPS/PBS (20% CHAPS/PBS stock solution) for 16 h at 4° C. The next day the solubilisates were spun at 43000 rpm (about 150000 g) in a TFT 65.13 rotor (Beckman™). The resulting pellet was discarded. The CHAPS solubilisates were resuspended and diluted 5 fold in PBS to destroy CHAPS micelles. Solubilized proteins were measured to be 0.8 mg/ml for the 80,000 g fraction and 0.57 mg/ml for the 150,000 g fraction. The solutions were stored until further use at −20° C.

TABLE 2

Buffers for membrane homogenates.

| Homogenization Buffer with protease inhibitor | Protease inhibitors, stock solutions |
|---|---|
| 300 mM Sucrose | 5M diisopropylfluorphosphate (DIFP) |
| 10 mM Tris ph 7.4 | 100 mM N-methylmaleinimid (NEM) |
| 1 mM DIFP | 100 mM EDTA |
| 1 mM EDTA | |
| 1 mM NEM | |
| 10 mg Trypsin Inhibitor from soybeans (Sigma ™) | | c) Affinity Purification with Immobilized Aβ(1-42) Globulomers

Immobilized Aβ(1-42) globulomers were resuspended and centrifuged at 12,500 rpm for 5 min. The supernatant was discarded and the immobilized globulomers were washed four times with 1 ml PBS. In between, each washing step the suspension was centrifuged for 5 min at 12,500 rpm and the respective supernatant discarded. After that, the globulomers were resuspended in 1×PBS and incubated for 16 h with the CHAPS solubilisates of the 80000 g and 150000 g membrane fraction of rat brain homogenates. Immobilized globulomers were recovered in a Pasteur pipette. Therefore, glass wool was crammed in a Pasteur pipette and rinsed with distilled water. Next, the CHAPS solubilisates containing the immobilized globulomers were poured into the pipette. The immobilisates settled on top of the glasswool while the liquid ran through and was collected in 50 ml Falcon tubes. The Pasteur pipette was washed with 3×0.5 ml PBS/0.4% CHAPS. In order to regain the immobilized globulomers the Pasteur pipette was broken at a height of about 2 cm. The immobilized globulomers were resuspended in PBS and pipetted quantitatively into an expender tube. PBS was removed by centrifugation at 12,500 rpm for 5 min. Elution and washing steps were performed sequentially as indicated in table 1. After each step, the immobilized globulomers were spun down at 12,500 g for 5 min and the supernatant was stored.

TABLE 3

Conditions to elute Aβ(1-42) globulomer-binding proteins.

| Name | Conditions | Volume | Time |
|---|---|---|---|
| Elution 1 | ¼ × PBS 0.05% SDS | 100 μl | 30 min |
| Elution 2 | 38/48 kDa globulomers in ¼ × PBS 0.05% SDS | 2 × 100 μl | 2 × 30 min |

TABLE 3-continued

Conditions to elute Aβ(1-42) globulomer-binding proteins.

| Name | Conditions | Volume | Time |
|---|---|---|---|
| Wash 1 | 1x PBS | 2 × 225 µl | 5 min |
| Elution 3 | PBS 0.5% SDS | 2 × 100 µl | 30 min |
| Elution 4 | SDS sample buffer + DTT | 2 × 100 µl | 30 min |
| Elution 5 | SDS sample buffer + DTT, 95° C. | 200 µl | 5 min | d) SDS-PAGE and Identification of Eluted Proteins by Mass Spectrometry

Figure 18:
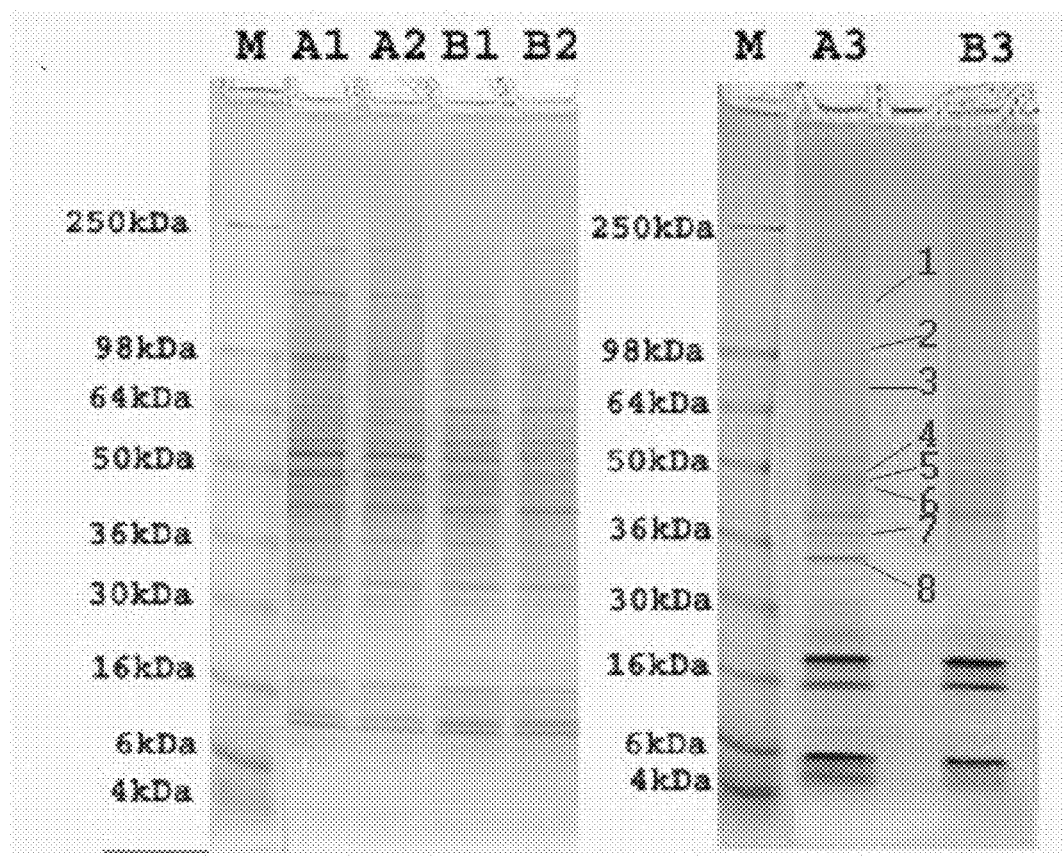
FIG. 18: Results of affinity approach with immobilized Aβ(1-42) globulomers

Immobilized Aβ(1-42) globulomers were used as an affinity bait to bind selectively Aβ(1-42) globulomer binding proteins. After distinct washing steps, proteins were eluted with increased stringency. The PBS/0.5% SDS elutions resulted in low protein amounts. In order to obtain significant protein quantities these SDS elutions were concentrated tenfold in centricon tubes. The resulting protein pattern was compared to SDS-patterns and Western Blots of earlier experiments. Special attention was focused on membrane proteins present in the eluates from the 80,000×g fraction. Interesting unknown proteins were selected for further identification by mass spectrometry. FIG. 18 shows the results of the elutions and the selected proteins.

The 4 most abundant bands at 20, 16, 6 and 4.5 kDa were expected to be non-globular Aβ oligomeric forms and were not regarded for analysis. The remaining eight abundant proteins were selected in the 80,000 g fraction for identification by mass spectrometry. After excision, relevant proteins were digested by trypsine. Peptide mass fingerprints were measured by MALDI-TOF-MS. Sequence alignment and database search was performed automatically according to standard procedures (e.g., Martin H Maurer et al. Proteome Science 2003 1, 4). In the following table 4 the identified proteins are listed.

TABLE 4

Amyloid-binding proteins determined by 38/48 kDa Aβ$_{1-42}$ globulomers affinity chromatography

| Band | Observed Molecular Weight (Da) | Theroretical. Molecular Weight (Da) | NIH accession number | Protein Name |
|---|---|---|---|---|
| 1 | 165500 | 188658 | gi201138801 | Intersectin 2 (SH3 domain-containing protein 1B) (EH and SH3 domains protein 2) EH domain and SH3 [*Mus musculus*] |
|   |   | 167378 | gi16924000 | densin-180 [*Rattus norvegicus*] |
|   |   | 175804 | gi16758820 | RIM2 protein [*Rattus norvegicus*] |
| 2 | 95000 | 94325 | gi1352648 | Osmotic stress protein 94 (Heat shock 70-related protein APG-1) [*Mus musculus*] |
|   |   | 122522 | gi17656906 | activin receptor interacting protein |
| 3 | 83000 | 84891 | gi13878219 | ribonuclease/agiogenin inhibitor 2 [*Mus musculus*] |
| 4 | 49000 | 51506 | gi6651165 | syndapin IIab [*Rattus norvegicus*] |
|   |   | 48496 | gi17477318 | similar to K-depended Na/Ca exchanger NCKX4 [*Homo sapiens*] |
|   |   | 4511 | gi423742 | beta-amyloid [guinea pig] (fragment 1-42) |
| 5 | 48000 | 41724 | gi71620 | actin beta [*Rattus norvegicus*] |
|   |   | 257186 | Gi2136947 | calcium channel BI1 [Rabbit] |
|   |   | 4511 | gi423742 | beta-amyloid protein [guinea pig] (fragment 1-42) |
| 6 |   |   |   | Not determined |
| 7 | 38000 | 4511 | gi423742 | beta-amyloid protein [guinea pig] (fragment 1-42) |
| 8 |   |   |   | Not determined |

Ten different proteins were detected in the analyzed positions. Band 6 and band 8 could not be matched to a protein in the database. In band 5 the calcium Channel BI1 was detected at an apparent molecular mass in SDS-PAGE of 48 kDa. Given the theoretical molecular weight of 257 kDa and the NIH accession number gi2136947 (equals P27884 in Swiss Prot data base) this is a fragment of the Voltage-dependent P/Q-type calcium channel subunit alpha-1A. Synonyms are:

Voltage-gated calcium channel subunit alpha Cav2.1
Calcium channel, L type, alpha-1 polypeptide isoform 4
Brain calcium channel I
BI Due to high sequence homology between rabbit and rat species the computer search lead to the rabbit protein although the experiment was performed with rat brain homogenate. Thus, it was demonstrated that Aβ(1-42) globulomer is capable of physically binding to the P/Q type voltage-gated presynaptic calcium channel.

SECOND SERIES OF EXPERIMENTS

Reference Example 9

Cell Culture

Primary hippocampal cell cultures were prepared from Wistar rat embryos at the embryonic age E19 in accordance with the protocol described earlier by Banker and Cowan (1977). Briefly, pregnant rats were deeply anesthetized by ether narcosis and decapitated. Embryos were rapidly removed and brains were dissected under constant cooling with chilled (~4° C.) phosphate buffered saline (PBS). Then both hippocampi were taken out and washed twice with ice-cold PBS followed by a wash with PBS at room temperature. Hippocampi were triturated using three siliconized pipettes with decreasing tip diameters. Cells were then plated on coverslips (density 60000 cells/coverslip) coated with 0.01% poly-L-lysine solution and stored at 37° C. in an incubator gassed with 5% $CO_2$ in normal air. The culture medium contained 0.25% penicil-line/streptomycine, 2% B27, 0.25% L-glutamine (Gibco, Karlsruhe, Germany).

Throughout culturing, we added 0.5 µM/L ω-conotoxin MVIIA to the culture medium to block N-type calcium channels and to stabilize the expression of P/Q-type currents. Cells were cultured for 14 to 28 days until used for experiments.

Reference Example 10

Current Recording

Currents were measured under whole-cell voltage-clamp conditions at room temperature using borosilicate pipettes of 2-4 MΩ resistance. Electrode solution contained (in mM/l): NaCl 10, KCl 100, $CaCl_2$ 0.25, EGTA 5, HEPES 10, glucose 40 (pH set at 7.3) when used for recordings of synaptic events. A low-chloride solution was used for experiments in which GABA induced currents were elicited, which consists of (mM): Cs-gluconate 130, CsCl 10, $CaCl_2$ 0.5, $MgCl_2$ 2, EGTA 10, HEPES 10, Mg-ATP 2 (pH: 7.3). Using this solution the calculated equilibrium potential for chloride-ions was −54 mV. During calcium current measurements the solution contained in (mM): CsCl 110, EGTA 10, HEPES 25, tris-phosphocreatine 10, Mg-ATP 4, Na-GTP 0.3 and 20 units/ml creatine-phosphokinase at pH 7.3. Osmolarity was adjusted to 295 mosmol/l, when necessary, by adding glucose. Bath solutions contained (in mM): NaCl 156, KCl 2, $CaCl_2$ 2, $MgCl_2$, Glucose 16.5, HEPES 10 (pH set to 7.3) for recordings of synaptic events and TEA-Cl 140, $BaCl_2$, 10, HEPES 10, and Glucose 20 at a pH: 7.3 for calcium currents, respectively. The bath perfusion was stopped for 10 min prior to the application of the Aβ(1-42) globulomer and baseline activity was recorded. Subsequently, Aβ(1-42) globulomer (164 nM in respect to the 12mer complex) was added to the bath by means of a micro pump, yielding a final concentration of 82 nM. TTX, ω-agatoxin IVA, ω-conotoxin MVIIA, roscovitine (Alomone Labs, Jerusalem, Israel), and nifedipine (Sigma, Deisenhofen, Germany) were added directly to the bath solution at the concentrations indicated.

Currents were measured with an Axopatch 200B (Axon Instruments, Union City, US) or an EPC-7 amplifier (HEKA, Lambrecht, Germany), digitized by a CED 1401 micro analog/digital converter (CED, Cambridge, UK) and stored on a PC (sample frequency 20 kHz). All recorded currents were low-pass filtered with a cut-off frequency of 3 kHz. Capacitive transients and series resistances were compensated on-line (~50-60% compensation) during the calcium current measurements. No compensation was performed during recordings of synaptic events. Data were evaluated off-line using Spike5 and Signal3 software (CED, Cambridge, UK). All calcium current traces were corrected for a specific linear leak (reversal potential 0 mV) determined at holding potential using ±5 mV potential steps.

Reference Example 11

Current Analysis

All cells were voltage clamped at a holding potential of −80 mV, and calcium ions were substituted by Barium ions to increase the amplitude of the current flow through the calcium channels. Peak amplitudes of the currents (I) evoked with the activation protocol were plotted as a function of membrane potential (V). The resulting IV-relations were fitted with a combination of a first order Boltzmann activation function and the Goldman-Hodgkin-Katz (GHK) current-voltage relation (Kortekaas and Wadman, 1997):

$$I(V) = V \frac{g_{max}}{1+\exp\left(\frac{V_h - V}{V_c}\right)} \frac{[Ba^+]_{in}/[Ba^+]_{out} - \exp(-\alpha V)}{1 - \exp(-\alpha V)} \quad [1]$$

with $$\alpha = F/RT$$

and $$g_{max} = \alpha F P_0 [Ba^+]_{out},$$

where $g_{max}$ is the maximal membrane conductance (which is proportional to the maximal permeability and the extracellular concentration of barium), $V_h$ is the potential of half maximal activation and $V_c$ is proportional to the slope of the curve at $V_h$. F represents the Faraday constant, R the gas constant, $P_0$ is the maximal permeability, and T the absolute temperature. The intracellular concentration of $Ba^{2+}$ was assumed to be 0.01 µM. Assuming higher values of up to 0.1 mM did not significantly change the resulting values of the parameters.

The voltage dependence of steady state inactivation of the barium current was estimated from the relation of peak current amplitude versus the pre-potential. This relation was well described by a Boltzmann function, which normalized the current:

$$N(V) = \frac{I(V)}{I_{max}} \quad [2]$$

where $$I(V) = \frac{I_{max}}{1 + \exp\left(\frac{V_h - V}{V_c}\right)}$$

where N(V) is the level of steady state inactivation determined from the current amplitude I(V) normalized to $I_{max}$, V is the pre-pulse potential, $V_h$ is the potential of half maximal inactivation and $V_c$ is a factor proportional to the slope of the curve at $V_h$.

Reference Example 12

Synaptic Events

For these recordings, all cells were voltage clamped at a holding potential of −70 mV. Synaptic events triggered by the release of GABA were inwardly directed ($E_{Cl^-}$~−10 mV) due to the use of high chloride concentrations in the pipette and the bath. Routinely, 10 min of baseline activity was acquired, serving as control data, before any drug application was started. Synaptic events were then analyzed off-line for frequency and amplitude, using a custom-made, template based algorithm.

Reference Example 13

Statistics

Values are presented as the mean±standard error of the mean (SEM). Statistical comparisons were made with Student's t-test. A p-value <0.05 was used to indicate significant differences.

Example 14

Figure 19:
Figure 19:
Figure 19:

Aβ(1-42) Globulomer Reduces Spontaneous Synaptic Activity in Hippocampal Cell Cultures Spontaneous synaptic was measured activity in cultured hippocampal neurons using whole-cell voltage clamp techniques ($V_{hold}$=−70 mV). Under our ionic conditions, all synaptic events appeared as inward currents (spontaneous postsynaptic currents;

sPSCs) with a mean frequency of 189±63/min (n=13). Bath-application of 82 nM Aβ(1-42) globulomer (globulomer molarities calculated with respect to the 12 mer complex) rapidly reduced the frequency of sPSCs to 38±5% of control (p<0.05; n=13; FIG. 19). This effect was partially reversible upon washout in 2 of 3 cells tested (61±16%) The median amplitude of events was 310±168 pA and was reduced to 84±10% under Aβ(1-42) globulomer (p<0.05; n=14; FIG. 20). Similar—but slightly weaker—effects were seen after application of 8.2 nM Aβ(1-42) globulomer (frequency reduced to 63±9%; p<0.05; median amplitude 94±5% of control, n=8, n.s.). Thus, the suppression of spontaneous synaptic activity by Aβ(1-42) globulomer is dose-dependent and starts at low nanomolar concentrations. Input resistance was not affected by Aβ(1-42) globulomer (control: 120.9±13.6 MΩ; Aβ(1-42): 131.6±13.7 MΩ).

Suppression of synaptic currents by an agent may be caused by changes in neuronal activity or, alternatively, by specific synaptic interactions. It was therefore tested for effects of Aβ(1-42) globulomer on active discharge properties by recording action potentials in current clamp mode. Action potentials elicited by current injection showed no difference in amplitude, shape or kinetics when compared before and after Aβ(1-42) globulomer application. In detail, the threshold for firing was −22.5±8.2 mV vs. −24.2±9.8 mV, and the amplitude of the AP (baseline to peak) amounted to 119.9±11.2 vs. 110.9±16.7 mV. Likewise, kinetic parameters did not differ: values for the half-width time were 3.5±1.6 ms vs. 4.0±2.9 ms, maximal rate of rise 100.5±46.4 V/s vs. 84.2±50.0 V/s and maximal rate of repolarization 46.0±18.6 V/s vs. 47.4±19.3 V/s (n=16 action potentials from 4 cells before and after Aβ(1-42) globulomer respectively. It thus appears that the alteration of synaptic activity by Aβ(1-42) globulomer may be caused by a direct interaction with pre- or postsynaptic proteins, rather than by an unspecific alteration of cellular excitability.

This hypothesis was corroborated by recordings of spontaneously occurring miniature postsynaptic currents (mPSCs) in the presence of TTX. Similar to spontaneous "macroscopic" PSCs, these currents were reduced in frequency by 82 nM Aβ(1-42) globulomer (yielding 56±9% of control; p<0.05; FIG. 20). However, the amplitude of mPSCs was unaltered (median amplitude 31.1±4.0 pA under control conditions vs. 30.2±5.2 pA in the presence of Aβ(1-42) globulomer, n=6). Upon washout for 10 minutes, the effect on event frequency recovered partially to 77±7.6% of control, n=6, wash: 4/6). Together, these data suggest that Aβ(1-42) globulomer interferes with the presynaptic machinery of transmitter release.

Example 15

Effects on Spontaneous and Miniature Inhibitory Postsynaptic Currents

Pharmacologically naive synaptic currents reflect a mixture of glutamatergic (excitatory) and GABAergic (inhibitory) events. In order to differentiate between these components, inhibitory postsynaptic currents were isolated by adding CNQX (20 μM) and DL-APV (30 μM) to the bath solution. The frequency of spontaneously occurring IPSCs was suppressed by Aβ(1-42) globulomer (yielding 64±5% of control; p<0.05; n=12) and the median amplitude was reduced to 82±2% of control (p<0.05). These reductions could be reversed to some degree following withdrawal of the globulomer (frequency: 90±12%; amplitude: 94±2%). Miniature inhibitory postsynaptic currents (mIPSCs, recorded in 0.5 μM TTX) did also show a similar reduction of frequency after application of Aβ(1-42) globulomer (52±10% of control; p<0.05; n=6). This effect was partially reversible upon washout, yielding 68±12% of control (FIG. 20). In addition, a reduction of mIPSC amplitude was observed (81±6% of control; p<0.05; no washout in 3/3 cells (85±6%)).

Example 16

Effects on Postsynaptic $GABA_A$ Receptors

In order to test for potential effects of Aβ(1-42) globulomer on postsynaptic $GABA_A$ receptors, a high (100 μM) concentration of GABA was applied by brief pressure-pulses directly onto the cell. Repetitive application of GABA to cultured cells elicited large (>1 nA) inward currents which showed only minor rundown with time. This behaviour was unaltered after application of Aβ(1-42) globulomer for 5 min, indicating that $GABA_A$ receptors are not affected by the agent (FIG. 21).

Example 17

Effects on Spontaneous and Miniature Excitatory Postsynaptic Currents

Finally, excitatory synaptic currents (EPSCs) were isolated in the presence of 5 μM gabazine (a $GABA_A$ receptor antagonist). Basal frequency of these events was 386±124/min. Their frequency was reduced by Aβ(1-42) globulomer to 14±4% of control (p<0.05; n=6; FIG. 20). Likewise, the amplitude was reduced to 79±4% of control (n=6; p<0.05; FIG. 20). The effect was partially reversible during washout (frequency increasing to 52±19% of control, amplitude to 96±6%; n=6). The frequency of miniature EPSCs was likewise suppressed to 57±9% of control (n=6; p<0.05), while the amplitude of mEPSCs remained stable (96±3% of control). The frequency suppression did not recover upon wash-out (54±8%; n=6).

Together, these data indicate that Aβ(1-42) globulomer depresses vesicular release at GABAergic and glutamatergic synapses, most likely by decreasing the probability of vesicle exocytosis from presynaptic terminals.

Example 18

Effects on Voltage-Activated Calcium Currents

Presynaptic vesicle release is triggered by an influx of calcium into the presynaptic terminal. Therefore, Aβ(1-42) globulomer might act on presynaptic calcium signalling. A common pathway for release of both, glutamatergic and GABAergic vesicles is presynaptic calcium influx via N-type or P/Q-type calcium channels. Therefore, the effects of Aβ(1-42) on whole-cell calcium currents in cultured hippocampal neurons were analyzed. Typical P/Q channel-mediated currents could be reliably elicited in somatic whole-cell recordings under our culture conditions. In these experiments, 10 mM $Ba^{2+}$ was used as charge carrier in the extracellular solution (see methods). Measurements were performed in the presence of 10 μM nifedipine (a L-type calcium channel blocker), ω-conotoxin MVIIA (a N-type calcium channel blocker) and blockers of other voltage-gated ion channels (TTX 0.5 μM, TEA 140 mM, $Cs^+$-based intracellular solution). Rundown of these currents was avoided by adding 20 U/ml phosphocreatine kinase and 10 mM tris-phosphocreatine to the pipette solution. Under these conditions, P/Q-type currents were evoked by a depolarizing voltage step to −10 mV (mean amplitude 1015±145 pA; FIG. 22). Aβ(1-42) globulomer reduced the amplitude of these currents to 62±7% of control (n=10). This effect was partially reversible in 3/3 cells.

If the effect of Aβ(1-42) globulomer on synaptic currents is mediated by block of P/Q-type calcium channels, it should be mimicked and occluded by the selective P/Q-type calcium channel blocker ω-Agatoxin IVA. Indeed, this toxin (0.5 μM) reduced the frequency of miniature PSCs to 27±7% (n=3; amplitude 90±7%), similar to the effect of Aβ(1-42) globulomer. Following pre-incubation with ω-Agatoxin IVA, Aβ(1-42) globulomer had no additional effect on the synaptic currents (n=6, frequency 108±15%; amplitude 102±7% of currents after w-Agatoxin IVA control; FIG. 24). These data suggest that ω-Agatoxin IVA and Aβ(1-42) globulomer share the same molecular mechanism.

The effect of Aβ(1-42) globulomer on P/Q-type calcium currents was further characterized by steady-state activation and -inactivation protocols (see methods). Maximal conductance ($g_{max}$) was 61.7±2.4 nS (control) versus 27.2±3.2 nS (Aβ(1-42) globulomer; p<0.05; n=6; FIG. 23). Thus, Aβ(1-42) globulomer reduces the current amplitude without affecting its voltage-dependent activation. In contrast to this marked reduction in conductance (and current amplitude), other kinetic parameters were not affected by Aβ(1-42) globulomer. Steady-state activation was characterized by $V_h$=−15.4±1.1 mV which was not changed after application of Aβ(1-42) globulomer ($V_h$=−17.3±1.3 mV; n=6). The slope of the fitted first-order Boltzmann-equation $V_c$ was −7.8±0.3 mV in control solution and −10.8±0.5 mV in Aβ(1-42) globulomer (not different, n=6). Likewise, steady-state inactivation was not affected by Aβ(1-42) globulomer, as indicated by stable values for the voltage at half-maximal inactivation (29.2±0.6 mV in control; 32.4±1.2 mV in Aβ(1-42) globulomer; n=4) and for the slope $V_c$ (−11.0±0.9 mV versus −12.6±1.1 mV; FIG. 23).). Thus, Aβ(1-42) globulomer reduces the current amplitude without affecting its voltage-dependent activation or inactivation.

In addition the effects of Aβ(1-42) globulomer on N- and L-type calcium currents were analyzed. Besides blockers for $Na^+$- and $K^+$-channels (see above) 0.5 μM ω-agatoxin IVA were added to block P/Q-channels. L-type calcium currents were isolated by addition of 0.5 μM ω-conotoxin MVIIA. Voltage pulses from −80 mV to −10 mV elicited inward currents of 597.7±230.9 pA amplitude which remained stable after addition of Aβ(1-42) globulomer (573.0±225.6 pA; n=3). When N-type currents were isolated by adding nifedipine (10 μM) instead of ω-conotoxin, the same voltage clamp protocol elicited inward currents which were, again, insensitive to Aβ(1-42) globulomer (amplitude in control solution 1368.9±332.8; amplitude in Aβ(1-42) globulomer 1399.8±376.4 pA; n=3). When all blockers were added together, the remaining calcium current (possibly R-type) was too small for a detailed analysis (<100 pA), indicating that this component was only marginally expressed in the cultured hippocampal neurons.

Example 19

Rescue by Roscovitine

Application of roscovitine in the presence of Aβ(1-42) globulomer did indeed partially recover the frequency of synaptic currents. While in these experiments Aβ(1-42) globulomer reduced the frequency of spontaneous PSCs to 38±10% of control, application of roscovitine (20 μM) brought this parameter back to 75±13% (n=5; FIG. 24).

Together, these data indicate that Aβ(1-42) globulomer reduces the frequency of spontaneous and miniature synaptic currents by suppression of presynaptic calcium influx via P/Q-type calcium channels.

THIRD SERIES OF EXPERIMENTS

Example 20

Enhancing P/Q Calcium Currents by Roscovitine Prevents/Reverses Chronic Aβ Globulomer-Induced Deficits on Evoked Synaptic Transmission in Hippocampal Tissue Rat hippocampal slice cultures (9 days old Wistar rats; 15-17 DIV) were incubated over night with either Aβ(1-42) globulomer (at a concentration corresponding to approximately 1 μM of Aβ monomer), Aβ(1-42) globulomer (at a concentration corresponding to approximately 1 μM of Aβ monomer)+20 μM roscovitine, or control (SDS). Recordings were performed (in artificial cerebrospinal fluid) from CA1 stratum radiatum after stimulation of the Schaffer collateral at different intensities.

Results are shown in FIG. 25, demonstrating that the application of globulomer strongly suppresses synaptic transmission. Co-application of 20 μM roscivitine completely prevents/reverses the globulomer-induced deficit.

Example 21

Effect of Extracellular $Ca^{2+}$ on sPSC Frequency after Treatment with Aβ(1-42) Globulomer Spontaneous synaptic activity was measured in cultured hippocampal neurons using whole-cell voltage clamp techniques ($V_{hold}$=−70 mV). Under the ionic conditions used ($E_{Cl}$~−10 mV) all synaptic events appeared as inward currents.

The effects of Aβ(1-42) globulomer (at a concentration corresponding to approximately 1 µM of Aβ monomer) were assessed by comparing spontaneously occurring postsynaptic currents (sPSCs) in single cells in 5 min intervals in the presence or absence of globulomer in bath solution containing 1 mM $Ca^{2+}$. Currents recorded prior to the addition of the globulomer served as control describing basal synaptic transmission. Currents recorded in the interval immediately after application were analysed with respect to the control data. Afterwards, extracellular $Ca^{2+}$ was elevated from 1 mM to 4 mM (leaving the concentration of globulomer unchanged). Currents in the following 5 min recording interval were again analysed with respect to control data.

Basal frequency of sPSCs in 1 mM $Ca^{2+}$ was 4.2±1.2 Hz. Bath-application of Aβ(1-42) globulomer rapidly reduced the sPSC frequency to 63±7% of control (p<0.05; n=6; FIG. 26 A+B). After elevation of extracellular $Ca^{2+}$ to 4 mM, sPSC frequency partially recovered to 77±13% of control (FIG. 26 B). In 4 of 6 cells tested, sPSC frequency increased, whereas it remained unaltered in the other 2 cells (FIG. 26 C).

Median amplitude of sPSCs under control conditions was 27.7±2.2 pA and remained unaltered after addition of Aβ(1-42) globulomer (97±5%; FIG. 26 D) or subsequent elevation of extracellular $Ca^{2+}$ (98±6%).

In most cases, prominent currents with amplitudes up to 2000 pA occurred directly after elevation of extracellular $Ca^{2+}$-concentration. These currents with multiple peaks (see FIG. 26 E) were rejected from analysis.

This clearly demonstrates that the principle of activating the P/Q type presynaptic calcium channel is effective in compensating the detrimental effects exerted by Aβ globulomer.

Example 22

Blocking P/Q Voltage-Gated Presynaptic Calcium Channels with Anti-P/Q Type Antibody Prevents Chronic Aβ Globulomer-Induced Deficits on Evoked Synaptic Transmission in Hippocampal Tissue Rat hippocampal slice cultures (9 day old Wistar rats; 15-17 DIV) were incubated over night with either Aβ(1-42) globulomer (at a concentration corresponding to approximately 1 µM of Aβ monomer), Aβ(1-42) globulomer (at a concentration corresponding to approximately 1 µM of Aβ monomer)+polyclonal antibody serum against the P/Q type voltage-gated presynaptic calcium channel antibody (sc-16228; 0.3 µg/ml=approximately 2 nM), or control (SDS). The antibody is an affinity purified goat polyclonal antibody raised against a peptide mapping near the C-terminus of the α1A subunit of the P/Q type voltage-gated presynaptic calcium channel of human origin. It is commercially available from Santa Cruz Biotechnology, Inc. Recordings were performed (in artificial cerebrospinal fluid) from CA1 stratum radiatum after stimulation of the Schaffer collateral at different intensities.

Results are shown in FIG. 27, demonstrating that the application of globulomer strongly suppresses synaptic transmission. Co-application of the antibody completely prevents the globulomer-induced deficit.

Example 23

Lack of Effect of Monomeric Aβ(1-42) Peptide on mPSCs

To test for the specificity of the Aβ(1-42) globulomer effect, a preparation of synthetic monomeric Aβ(1-42) peptide was applied while recording mPSCs in the presence of TTX. A temporarily stable monomer solution was prepared by dissolving synthetic Aβ(1-42) in 0.1% NaOH (see reference example 2). A Coomassie-stained SDS-PAGE confirmed the presence of Aβ(1-42) monomer and the Aβ(1-42) globulomer at the expected molecular weights in the respective preparations. The monomeric preparation was bath-applied at an initial concentration of 1 µM Aβ(1-42) monomer, which equals the amount of monomer contained in the globulomer preparation. Frequency of mPSCs was 87±3% of control in the presence of monomeric Aβ(1-42) (n=7; n.s.) (FIG. 28), which was similar to the frequency observed by application of the solvent alone (0.1% NaOH diluted 1:1000 in bath solution; 89±9% of control; n=7) (FIG. 28). The amplitude of mPSCs was unaltered after application of the monomer preparation (median amplitude, 34.2±3.0 pA under control conditions vs 33.7±3.0 pA in the presence of Aβ(1-42) monomer) or its respective solvent (median amplitude, 32.4±1.5 pA under control conditions vs 32.3±1.1 pA in the presence of the solvent).

Note that, in general, Aβ(1-42) peptide can hardly be maintained in its monomeric state in physiological buffers, because it aggregates within minutes to protofibrils and fibrils. 0.1% NaOH was used as the initial solubilization buffer for the synthetic Aβ(1-42) peptide, which is the most suitable buffer for solubilising and maintaining Aβ(1-42) peptide in a monomeric state under the experimental conditions. Although great care was taken to minimize Aβ(1-42) peptide aggregation, aggregation was observed at the final dilution of 0.0001% NaOH in the bath solution when samples were retrieved after the actual experiments. Therefore, the applied monomeric Aβ(1-42) peptide is likely a mixture of Aβ(1-42) aggregation states (i.e., Aβ(1-42) monomer, Aβ(1-42) protofibrils, and Aβ(1-42) fibrils). Furthermore, aggregated Aβ(1-42) peptide within the monomeric Aβ(1-42) preparation can also be seen in the SDS-PAGE gel loading pocket. Preparations of Aβ(1-42) tend to adhere to surfaces and therefore may reach lower final effective concentrations at the target cells. Therefore, the Aβ(1-42) content was representatively determined after the experiment and it was found that in both Aβ(1-42) monomer and globulomer preparations, >50% of the initial Aβ(1-42) peptide were present during the electrophysiological recordings.

The invention claimed is:

1. A method for the treatment of an amyloidosis disease comprising administering to a subject in need thereof an agent that inhibits the interaction between Aβ globulomer and P/Q type voltage-gated presynaptic calcium channel, wherein the agent is an antibody that binds to the P/Q type voltage-gated presynaptic calcium channel, wherein the amyloidosis disease is selected from the group consisting of Alzheimer's disease and Down's syndrome, wherein the antibody is raised against a peptide mapping near the C-terminus of the α1A subunit of the P/Q type voltage-gated presynaptic calcium channel, and wherein the antibody is sc-16228.

2. The method of claim 1, wherein the treatment is for the restoration of memory function.

3. The method of claim 1, wherein the treatment is for the restoration of performance of activities of daily living (ADL) capacity.

* * * * *